United States Patent
Raz et al.

(10) Patent No.: US 6,589,940 B1
(45) Date of Patent: Jul. 8, 2003

(54) IMMUNOSTIMULATORY OLIGONUCLEOTIDES, COMPOSITIONS THEREOF AND METHODS OF USE THEREOF

(75) Inventors: Eyal Raz, Del Mar, CA (US); Mark Roman, Encinitas, CA (US); Dino Dina, Oakland, CA (US)

(73) Assignee: Dynavax Technologies Corporation, Berkeley, CA (US)

( * ) Notice: Subject to any disclaimer, the term of this patent is extended or adjusted under 35 U.S.C. 154(b) by 0 days.

(21) Appl. No.: 09/296,477

(22) Filed: Apr. 22, 1999

Related U.S. Application Data

(63) Continuation-in-part of application No. 09/092,329, filed on Jun. 5, 1998, now abandoned.
(60) Provisional application No. 60/048,793, filed on Jun. 6, 1997.

(51) Int. Cl.[7] .......................... A01N 43/04; C12Q 1/68; C12N 15/88; C07H 21/02; A61K 38/00
(52) U.S. Cl. ......................... 514/44; 435/6; 435/91.1; 435/455; 435/458; 514/2; 530/300; 536/23.1
(58) Field of Search ............................ 435/6, 458, 455, 435/91.7; 530/300; 536/23.1; 514/2, 44

(56) References Cited

U.S. PATENT DOCUMENTS

| | | | |
|---|---|---|---|
| 4,458,066 A | 7/1984 | Caruthers et al. | |
| 4,650,675 A | 3/1987 | Borel et al. | |
| 4,849,513 A | 7/1989 | Smith et al. | |
| 4,910,300 A | 3/1990 | Urdea et al. | |
| 4,948,882 A | 8/1990 | Ruth | |
| 5,015,733 A | 5/1991 | Smith et al. | |
| 5,093,232 A | 3/1992 | Urdea et al. | |
| 5,118,800 A | 6/1992 | Smith et al. | |
| 5,118,802 A | 6/1992 | Smith et al. | |
| 5,124,246 A | 6/1992 | Urdea et al. | |
| 5,218,103 A | 6/1993 | Caruthers et al. | |
| 5,391,723 A | 2/1995 | Priest | |
| 5,453,496 A | 9/1995 | Caruthers et al. | |
| 5,460,831 A | 10/1995 | Kossovsky et al. | |
| 5,552,391 A | 9/1996 | Coutts et al. | |
| 5,574,142 A | * 11/1996 | Meyer, Jr. et al. | ......... 536/23.1 |
| 5,780,448 A | * 7/1998 | Davis | .......................... 514/44 |
| 5,831,016 A | 11/1998 | Wang et al. | |
| 5,849,719 A | 12/1998 | Carson et al. | |
| 6,090,791 A | 7/2000 | Sato et al. | |
| 6,194,388 B1 | 2/2001 | Krieg et al. | |
| 6,207,646 B1 | 3/2001 | Krieg et al. | |
| 6,214,806 B1 | 4/2001 | Krieg et al. | |
| 6,218,371 B1 | 4/2001 | Krieg et al. | |

FOREIGN PATENT DOCUMENTS

| | | |
|---|---|---|
| EP | 0 468520 A2 A3 | 1/1992 |
| WO | WO 95/26204 | 10/1995 |
| WO | WO 96/02555 | 2/1996 |
| WO | WO 97/28259 | 8/1997 |
| WO | WO 97/29195 A2 A3 | 8/1997 |
| WO | WO 98/16247 | 4/1998 |
| WO | WO 98/18810 | 5/1998 |
| WO | WO 98/32462 A1 | 7/1998 |
| WO | WO 98/37919 | 9/1998 |
| WO | WO 98/40100 | 9/1998 |
| WO | WO 98/52581 | 11/1998 |
| WO | WO 98/52962 A1 | 11/1998 |
| WO | WO 98/55495 | 12/1998 |
| WO | WO 98/55609 | 12/1998 |
| WO | WO 98/55495 A2 A3 | 12/1998 |
| WO | WO 99/11275 | 3/1999 |
| WO | WO 99/61056 A2 | 12/1999 |
| WO | WO 00/09159 A1 | 2/2000 |
| WO | WO 00/40269 A2 A3 | 7/2000 |
| WO | WO 00/50006 A2 A3 | 8/2000 |
| WO | WO 00/50075 A2 A3 | 8/2000 |
| WO | WO 00/54803 A2 A3 | 9/2000 |

OTHER PUBLICATIONS

Agrawal et al. Molecular Medicine Today, Feb. 2000, vol. 6, pp. 72–81.*
Krieg et al. Immunology Today. Oct. 2000, vol. 21, No. 10, pp. 521–527.*
McCluskie et al. Molecular Medicine, 1999, vol. 5, pp. 287–300.*
Weiner, G. J. Leukocyte Biol. Oct, 2000. vol. 68, pp. 455–4623.*
Robert Thornton Morrison et al., Organic Chemistry, pp. 35–36 (1992).*
Sanghvi, Y.S. Heterocyclic Base Modifications in nucleic acids and their applications in antisense oligonucleotides. pp. 273–288, 1993.*
Davis, H.L. (1997). "Plasmid DNA Expression Systems for the Purpose of Immunization," *Curr. Opin. Biotech.* 8:635–640.
Davis, H.L. et al. (1998) "CpG DNA is a Potent Enhancer of Specific Immunity in Mice Immunized with Recombinant Hepatitis B Surface Antigen," *J. Immunol.* 160:870–876.
Elkins, K.L. et al. (1999). "Bacterial DNA Containing CpG Motifs Stimulates Lymphocyte–Dependent Protection of Mice Against Lethal Infection with Intracellular Bacteria," *J. Immunol.* 162:2291–2298.
Gray, G.D. et al. (1997). "Immune Cell Involvement in Anti–c–myc DNA Prevention of Tumor Formation in a Mouse Model of Burkitt's Lymphoma," *Nucleosides & Nucleotides* 16(7–9):1727–1730
Krieg, A.M. (Feb. 1999). "CpG DNA: A Novel Immunomodulator," *Trends Microbiol.* 7(2):64–65.

(List continued on next page.)

Primary Examiner—Ram R. Shukla
Assistant Examiner—Jane Zara
(74) Attorney, Agent, or Firm—Morrison & Foerster LLP

(57) ABSTRACT

The invention relates to immunostimulatory oligonucleotide compositions. These oligonucleotides comprise an immunostimulatory octanucleotide sequence. These oligonucleotides can be administered in conjunction with an immunostimulatory peptide or antigen. Methods for modulating an immune response upon administration of the oligonucleotide are also disclosed. In addition, an in vitro screening method to identify oligonucleotides with immunostimulatory activity is provided.

50 Claims, 16 Drawing Sheets

OTHER PUBLICATIONS

Liew. (Oct. 1996). GB–EST9, Accession #AA094019.
Ramsey, A.J. et al. (1997). "DNA Immunization," *Immunol. & Cell Biol.* 75:360–363.
Zimmermann, S. et al. (1998). "Cutting Edge: CpG Oligonucleotides Trigger Protective and Curative Th1 Responses in Lethal Murine Leishmaniasis," *J. Immunol.* 160:3627–3630.
Agrawal et al., "Efficient methods for attaching non–radioactive labels to the 5' ends of synthetic oligodeoxyribonucleotides" (1986) *Nucleic Acids Res.* 14:6227–6245.
*Animal Cell Culture: A Practical Approach,* (1987) R.I. Freshney, ed., IRL Press, Oxford, (Table of Contents).
Aramaki et al., "Interferon–γ inductive effect of liposomes as an immunoadjuvant" (1995) *Vaccine* 13:1809–1814.
Atherton et al., "Synthesis of a 21–residue fragment of human proinsulin by the polyamide solid phase method" (1981) *Hoppe–Seylers Z. Physiol. Chem.* 362:833–839.
Ballas et al., "Induction of NK activity in murine and human cells by CpG motifs in oligodeoxynucleotides and bacterial DNA" (1996) *J.Immunol.* 157:1840–1845.
Benoit et al., "Peptides. Strategies for antibody production and radioimmunoassays" (1987) *Neuromethods* 6:43–72.
Bischoff et al., "Introduction of 5'–terminal functional groups into synthetic oligonucleotides for selective immobilization" (1987) *Analytical Biochemistry* 164:336–344.
Blanks et al., "An oligodeoxynucleotide affinity column for the isolation of sequence specific DNA binding proteins" (1988) *Nucleic Acids Res.* 16:10283–10299.
Bliss et al., "IL–12, as an adjuvant, promotes a T helper 1 cell, but does not suppress a T helper 2 cell recall response" (1996) *J. Immunol.* 156:887–894.
Borel et al., "A novel technique to link either proteins or peptides to gammaglobulin to construct tolerogens" (1990) *J. Immunol. Methods* 126:159–168.
Borel et al., "Food allergens transformed into tolerogens" (1995) *Int. Arch. Allergy Immunol.* 107:264–267.
Borel et al., "Parenteral and oral administration of tolerogens: Protein–IgG conjugates. Oral tolerance: Mechanisms and applications" (1996) *Ann. N.Y. Acad. Sci.,* 778:80–87.
Boujrad et al., "Inhibition of hormone–stimulated steroidogenesis in cultured Leydig tumor cells by a cholesterol–linked phosphorothioate oligondeoxynucleotide antisense to diazepam–binding inhibitor" (1993) *Proc. Natl. Acad. Sci. USA* 90:5728–5731.
Bousquet et al., "Molecular mechanisms of the adsorption of a model protein (human serum albumin) on poly(methylidene malonate 2.1.2) nanoparticles" (1999) *Pharm. Res.* 16:141–147.
Bradley et al., "Hepatitis A virus: Growth characteristics of in vivo and in vitro propagated wild and attenuated virus strains" (1984) *J. Med. Virol.* 14:373–386.
Branda et al., "Immune stimulation by an antisense oligomer complementary to the rev gene of HIV–1" (1993) *Biochem. Pharmacol.* 45:2037–2043.
Branda et al., "Amplification of antibody production by phosphorothioate oligodeoxynucleotides" (1996) *J. Lab. Clin. Med.* 128:329–338.
Braun et al., "Immunogenic duplex nucleic acids are nuclease resistant" (1988) *J. Immunol.* 141:2084–2089.
Brazolot Millan et al., "CpG DNA can induce strong Th1 humoral and cell–mediated immune responses against hepatitis B surface antigen in young mice" (1988) *Proc. Natl. Acad. Sci. USA* 95:15553–15558.

Breiteneder et al., "The gene coding for the major birch pollen allergen Betvl is highly homologous to a pea disease resistance response gene" (1989) *EMBO J.* 8:1935–1938.
Broide et al., "Intradermal gene vaccination down–regulates both arms of the allergic response" (1997) *J. Allergy Clin. Immunol.* 99:Abstracts–S129: 523.
Broide et al., "Immunostimulatory DNA sequences inhibit IL–5, eosinophilic inflammation, and airway hyperresponsiveness in mice" (1988) *J. Immunol.* 161:7054–7062.
Broide et al., "DNA–based immunization for astham" (1999) *Int. Arch. Allergy Immunol.* 118:453–456.
Carson et al., "Oligonucleotide adjuvants for T helper 1 (Th1)–specific vaccination" (1997) *J. Exp. Med.* 186:1621–1622.
Castro et al., "The autoantigen La/SSB is a calmodulin–binding protein" (1996) *Cell Calcium* 20:493–500.
Chace et al., "Bacterial DNA–induced NK cell IFN–γ production is dependent on macrophage secretion of IL–12" (1997) *Clin. Immunol. and Immunopathol.* 84:185–193.
Chaturvedi et al., "Stabilization of triple–stranded oligonucleotide complexes: use of probes containing alternating phosphodiester and stereo–uniform cationic phosphoramidate linkages" (1996) *Nucleic Acids Res.* 24:2318–2323.
Chavany et al., "Polyalkylcyanoacrylate nanoparticles as polymeric carriers for antisense oligonucleotides" (1992) *Pharm. Res.* 9:441–449.
Chavany et al., "Adsorption of oligonucleotides onto polyisohexylcyanoacrylate nanoparticle protects them against nucleases and increases their cellular uptake" (1994) *Pharm. Res.* 11:1370–1378.
Chua et al., "CpG oligodeoxynucleotides act as adjuvants that switch on T helper 1 (Th1) immunity" (19970 *J. Exp. Med.* 186:1623–1631.
Chu et al., "Sequence analysis of cDNA coding for a major house dust mite allergen, Der p 1 homology with cysteine proteases" (1988) *J. Exp. Med.* 167:175–182.
Chua et al., "Expression of *Dermatophagoides pteronyssinus* allergen, Derr p II, in *Escherichia coli* and the binding studies with human IgE" (1990) *Int. Arch. Allergy Appl. Immunol.* 91:124–129.
Conboy et al., "Novel genetic regulation of T helper 1 (Th1)/Th2 cytokine production and encephalitogenicity in inbred mouse strains" (1997) *J. Exp. Med.* 185:439–451.
Connolly, Bernard A., "Chemical synthesis of oligonucleotides containing a free sulphydryl group and subsequent attachment of thiol specific probes" (1985) *Nucleic Acids Res.* 13:4485–4502.
Connolly, Bernard A., "The synthesis of oligonucleotides containing a primary amino group at the 5'–terminus" (1987) *Nucleic Acids Res.* 15:3131–3139.
Corey et al., "Generation of a hybrid sequence–specific single–stranded deoxyribonuclease" (1987) *Science* 238:1401–1403.
Cowdery et al., "Bacterial DNA induces NK cells to produce IFN–γ in vivo and increases the toxicity of lipopolysaccharides" (1996) *J. Immunol.* 156:4570–4575.
*Current Communications in Molecular Biology,* (1987) "Gene transfer vectors for mammalian cells" Jeffrey H. Miller, Michele P. Calos, eds., Cold Spring Harbor Laboratory (Table of Contents).
*Current Protocols in Immunology,* (1998) John E. Coligan et al., eds., John Wiley & Sons, Inc., (Table of Contents).

*Current Protocols in Molecular Biology,* (1995) Frederick M. Ausubel et al., eds., John Wiley & Sons, Inc., (Table of Contents).

Dixon, B., "The third vaccine revolution" (1995) *Bio/Technology* 13:420–421.

Douglas et al., "Nanoparticles in drug delivery" (1987) *Crit. Rev. Ther. Drug. Carrier Syst.* 3:233–261.

Dumas et al., "Induction of tolerance by administration of hapten–immunoglobulin conjugates is associated with decreased IL–2 and IL–4 production" (1995) *Arch. Dermatol. Res.* 287:123–128.

Elsayed et al., "The structural requirements of epitopes with IgE binding capacity demonstrated by three major allergens from fish, egg and tree pollen" (1991) *Scand. J. Clin. Lab. Invest. Suppl.* 204:17–31.

*Enzymatic Peptide Synthesis,* Willi Kullman, Ed., CRC Press, Inc., (Table of Contents).

Fraley et al., "New generation liposomes: the engineering of an efficient vehicle for intracellular delivery of nucleic acids" (1981) *Trends Biochem. Sci.* 6:77–80.

Friedmann, "Overcoming the obstacles to gene therapy" (Jun. 1997) *Scientific American,* pp. 96–101.

Froehler, Brian C., "Deoxynucleoside H–phosphonate diester intermediates in the synthesis of internucleotide phosphate analogues" (1986) *Tetrahedron Lett.* 27:5575–5578.

Gao et al., "Circularization of oligonucleotides by disulfide bridge formation" (1995) *Nucleic Acids Res.* 23:2025–2029.

Geoghegan et al., "Site–directed conjugation of nonpeptide groups to peptides and proteins via periodate oxidation of a 2–amino alcohol. Application to modification at N–terminal serine" (1992) *Bioconjug. Chem.* 3:138–146.

Goodchild, John, "Conjugates of oligonucleotides and modified oligonucleotides: A review of their synthesis and properties" (1990) *Bioconjug. Chem.* 1:165–187.

Grabarek et al., "Zero–length crosslinking procedure with the use of active esters" (1990) *Anal. Biochem.* 185:131–135.

Gramzinski et al., "Immune response to a hepatitis B DNA vaccine in aotus monkeys: A comparison of vaccine formulation, route, and method of administration" (1998) *Mol. Med.* 4:109–118.

Hagiwara et al., "A new drug–delivery–system of anticancer agents: Activated carbon particles adsorbing anticancer agents" (1987) *In Vivo* 1:241–252.

Halpern et al., "Bacterial DNA induces murine interferon–γ production by stimulation of interleukin–12 and tumor necrosis factor–α" (1996) *Cell. Immunol.* 167:72–78.

*Handbook of Experimental Immunology,* "Volume 4: Applications of immunological methods in biomedical sciences" D. M. Weir, ed., Blackwell Scientific Publications, Oxford (Table of Contents).

Haneji et al., "Identification of α–Fodrin as a candidate autoantigen in primary Sjögren's syndrome" (1997) *Science* 276:604–607.

Haralambidis et al., "The preparation of polyamide–oligonucleotide probes containing multiple non–radioactive labels" (1990) *Nucleic Acids Res.* 18:501–505.

Haralambidis et al., "The synthesis of polyamide–oligonucleotide conjugate molecules" (1990) *Nucleic Acids Res.* 18:493–499.

Horner et al., "Rapid communication: Immunostimulatory DNA is a potent mucosal adjuvant" (1998) *Cell Immunol.* 190:77–82.

Jäger et al., "Synthesis of deoxynucleoside methylphosphonates via a phosphonamidite approach" (1984) *Tetrahedron Lett.*25:1437–1440.

Jäger et al., "Oligonucleotide N–alkylphosphoramidates: Synthesis and binding to polynucleotides" (1988) *Biochem.* 27:7237–7246.

Jakob et al., "Activation of cutaneous dendrific cells by CpG–containing oligodeoxynucleotides: A role for dendritic cells in the augmentation of Th1 responses by immunostimulatory DNA" (1998) *J. Immunol.* 161:3042–3049.

James et al., "Safe administration of the measles vaccine to children allergic to eggs" (1995) *N. Engl. J. Med.* 332:1262–1266.

Jiang et al., "Inactivation of poliovirus with β–propiolactone" (1986) *J. Biol. Stand.* 14:103–109.

Kataoka et al., "Antitumor activity of synthetic oligonucleotides with sequences from cDNA encoding proteins of *mycobacterium bovis* BCG" (1992) *Jpn. J. Cancer Res.* 83:244–247.

Kessler, Christoph, "Nonradioactive labeling methods for nucleic acids" (1992) *Noniosotopic DNA Probe Techniques,* Kricka (ed.), Academic Press, Inc., pp. 29–92.

Kimura et al., "Binding of oligoguanylate to scavenger receptors is required for oligonucleotides to augment NK cell activity and induce IFN" (1994) *J. Biochem. (Tokyo)* 116:991–994.

Kline et al., "Immune redirection by CpG oligonucleotides conversion of a Th2 response to a Th1 response in a murine model of asthma" (1997) *J. Ivest. Med.* 45(3):282A.

Klinman et al., "CpG motifs present in bacterial DNA rapidly induce lymphocytes to secrete interleukin 6, interleukin 12, and interferon γ" (1996) *Proc. Natl. Acad. Sci. USA* 93:2879–2883.

Klinman et al., "Contribution of CpG motifs to the immunogenicity of DNA vaccines" (1997) *J. Immunol.* 158:3635–3639.

Kovarik et al., "CpG oligodeoxynucleotides can circumvent the Th2 polarizaiton of neonatal responses to vaccines but may fail to fully redirect Th2 responses established by neonatal priming" (1999) *J. Immunol.* 162:1611–1617.

Kramers et al., "Specificty of monoclonal anti–nucleosome auto–antibodies derived from lupus mice" (1996) *J.Autoimmun.* 9:723–729.

Kremsky et al., "Immobilization of DNA via oligonucleotides containing an aldehyde or carboxylic acid group at the 5' terminus" (1987) *Nucleic Acids Res.* 15:2891–2909.

Krieg et al., "A role for endogenous retroviral sequences in the regulation of lymphocyte activation" (1989) *J. Immunol.* 143:2448–2451.

Krieg et al., "CpG motifs in bacterial DNA trigger direct B–cell activation" (1995) *Nature* 374:546–549.

Krieg et al., "Oligodeoxynucleotide modifications determine the magnitude of B cell stimulation by CpG motifs" (1996) *Antisense & Nucleic Acid Drug Dev.* 6:133–139.

Krieg, Arthur M., "Lymphocyte activation by CpG dinucleotide motifs in prokaryotic DNA" (1996) *Trends in Microbiology* 4:73–77.

Krieg, Arthur M., "Leukocyte stimulation by oligodeoxynucleotides" (1998) *Applied Antisense Oligonucleotide Technology* Ch. 24, pp. 431–448, C.A. Stein et al., eds. Wiley–Liss, Inc.

Krieg et al., "The role of CpG dinucleotides in DNA vaccines" (1998) *Trends Microbiol.* 6:23–27.

Krieg, et al., "CpG induces sustained IL-12 expression in vivo and resistance to *listeria monocytogenes* challenge" (1998) *J. Immunol.* 161:2428–2434.

Krieg et al., "Sequence motifs in adenoviral DNA block immune activation by stimulatory CpG motifs" (1998) *Proc. Natl. Acad. Sci. USA* 95:12631–12636.

Kuramoto et al., "In situ infiltration of natural killer–like cells induced by intradermal injection of the nucleic acid fraction from BCG" (1989) *Microbiol. Immunol.* 33:929–940.

Lambert et al., "Effect of polyisobutylcyanoacrylate nanoparticles and lipofectin loaded with oligonucleotides on cell viability and PKCα neosynthesis in HepG2 cells" (1998) *Biochimie* 80:969–976.

Latimer et al., "Specificity of monoclonal antibodies produced against phosphorothioate and ribo modified DNAs" (1995) *Mol. Immunol.* 32:1057–1064.

Lea et al., "Cloning and sequencing of cDNAs encoding the human sperm protein, SP17" (1996) *Biochim. Biophys. Acta* 1307:263–266.

Leclerc et al., "The preferential induction of a TH1 immune response by DNA–based immunization is mediated by the immunostimulatory effect of plasmid DNA" (1997) *Cell. Immunol.* 179:97–106.

Leff, David N., "Non–lipid polymer beats liposome vector in mouse gene therapy experiment" (1997) *Bioworld* 86:1–2.

Lipford et al., "CpG–containing synthetic oligonucleotides promote B and cytotoxic T cell responses to protein antigen: a new class of vaccine adjuvants" (1997) *Eur. J. Immunol.* 27:2340–2344.

Lipford et al., "Immunostimulatory DNA: sequence–dependent production of potentially harmful or useful cytokines" (1997) *Eur. J. Immunol.* 27:3420–3426.

*Liposomes: From Physics to Applications,* (1993) D.D. Lasic, Elsevier, Amsterdam, (Table of Contents).

Liu et al., "Immunostimulatory CpG oligodeoxynucleotides enhance the immune response to vaccine strategies involving granulocyte–macrophage colony–stimulating factor" (1998) *Blood* 92:3730–3736.

Macfarlane et al., "Unmethylated CpG–containing oligodeoxynucleotides inhibit apoptosis in WEH1 231 B lymphocytes induced by several agents: evidence for blockade of apoptosis at a distal signalling step" (1997) *Immunology* 91:586–593.

Malley, Arthur, "The immune response of offspring mice from mothers immunized during pregnancy with protein antigens" (1989) *J. Reprod. Immunol.* 16:173–186.

Maniatis et al., "Dephosphorylation of DNA" (1982) *Molecular Cloning: A Laboratory Manual,* Cold Spring Harbor Laboratory, New York, pp. 133–134.

Manickan et al., "Genetic immunization against herpes simplex virus" (1995) *J. Immunol.* 155:259–265.

Mannino et al., "Liposome mediated gene transfer" (1988) *Biotechniques,* 6:682–690.

Matsuo et al., "Unmasking of an unusual myelin basic protein epitope during the process of myelin degeneration in humans" (1997) *Am. J. Pathol.* 150:1253–1266.

McCluskie et al., "Cutting edge: CpG DNA is a potent enhancer of systemic and mucosal immune responses against hepatitis B surface antigen with intranasal administration to mice" (1998) *J. Immunol.* 161(9):4463–4466.

McCutchan et al., "Genetic variants of HIV–1 in Thailand" (1992) *AIDS Res. Hum. Retroviruses* 8:1887–1895.

Menon et al., "The production, binding characteristics and sequence analysis of four human IgG monoclonal antiphospholipid antibodies" (1997) *J.Autoimmun.* 10:43–57.

Messina et al., "The influence of DNA structure on the in vitro stimulation of murine lymphocytes by natural and synthetic polynucleotide antigens" (1993) *Cell. Immunol.* 147:148–157.

Messing et al., "A system for shotgun DNA sequencing" (1981) *Nucleic Acids Res.* 9:309–321.

Miller et al., "Syntheses and properties of adenine and thymine nucleoside alkyl phosphotriesters, the neutral analogs of dinucleoside monophosphates" (1971) *JACS* 93:6657–6665.

Mitragotri et al., "Ultrasound–mediated transdermal protein delivery" (1995) *Science* 269:850–853.

Mojcik et al., "Administration of a phosphorothioate oligonucleotide antisense to murine endogenous retroviral MCF env causes immune effects in vivo in a sequence–specific manner" (1993) *Clin. Immuno. and Immunopathol.* 67:130–136.

Moldoveanu et al., "CpG DNA, a novel immune enhancer for systemic and mucosal immunication with influenza virus" (1998) *Vaccine* 16:1216–1224.

Molecular Cloning, A Laboratory Manual, (1982) T. Maniatis et al., eds., Cold Spring Harbor Laboratory, (Table of Contents).

Molecular Cloning: A Laboratory Manual, (1989) Second Edition, J. Sambrook et al., eds., Cold Spring Harbor Laboratory Press, (Table of Contents).

Myers et al., "The emergence of simian/human immunodeficiency viruses" (1992) *AIDS Res. Hum. Reroviruses* 8:373–386.

Nelson et al., "Bifunctional oligonucleotide probes synthesized using a novel CPG support are able to detect single base pair mutations" (1989) *Nucleic Acids Res.* 17:7187–7194.

Nemer et al., "Ribonucleotide analogues having novel internucleotide linkages" *Tetrahedron Lett.* (1980) 21:4149–4152.

Nguyen et al., "Studies towards the design of a modified GC base pair with stability similar to that of the AT base pair" (1997) *Tetrahedron Lett.* 38:4083–4086.

*Oligonucleotide Synthesis. A Practical Approach,* (1984) M.J. Gait, ed., IRL Press, (Table of Contents).

O'Shannessy et al., "Specific conjugation reactions of the oligosaccharide moieties of immunoglobulins" (1985) *J. Applied Biochem.* 7:347–355.

Paesen et al., "A tick homologue of the human Ki nuclear autoantigen" (1996) *Biochem.Biophys.Acta* 1309:9–13.

Pardoll et al., "Exposing the immunology of naked DNA vaccines" (1995) *Immunity* 3:165–169.

Pertmer et al., "Influenza virus nucleoprotein–specific immunoglobulin G subclass and cytokine responses elicited by DNA vaccination are dependent on the route of vector DNA delivery" (1996) *J. Virol.* 70:6119–6125.

Peyrottes et al., "Oligodeoxynucleoside phosphoramidates (P–NH$_2$): synthesis and thermal stability of duplexes with DNA and RNA targets" (1996) *Nucleic Acids Res.* 24:1841–1848.

Pisetsky et al., "Stimulation of murine lymphocyte proliferation by a phosphorothioate oligonucleotide with antisense activity for herpes simplex virus" (1994) *Life Sci.* 54:101–107.

Pisetsky et al., "Immunological properties of bacterial DNA. DNA vaccines: A new era in vaccinology" (1995) *Ann. N.Y. Acad. Sci.*, 772:152–163.

Pisetsky, David S., "The immunologic properties of DNA" (1996a) *J. Immunol.* 156:421–423.

Pisetsky, David S., "Immune activation by bacterial DNA: A new genetic code" (1996b) *Immunity* 5:303–310.

Rafnar et al., "Cloning of Amb αI (antigen E), the major allergen family of short ragweed pollen" (1991) *J. Biol. Chem.* 266:1229–1236.

Rahman et al., "Sequences of monoclonal antiphospholipid antibodies: Variations on an anti–DNA antibody theme" (1996) *Semin. Arthritis Rheum.* 26:515–525.

Raz et al., "Intradermal gene immunization: The possible role of DNA uptake in the induction of cellular immunity to viruses" (1994) *Proc. Natl. Acad. Sci. USA* 91:9519–9523.

Raz et al., "Preferential induction of a $Th_1$ immune response and inhibition of specific IgE antibody formation by plasmid DNA immunization" (1996) *Proc. Natl. Acad. Sci. USA* 93:5141–5145.

Redford et al., "Cyclosporin A enhances IL–12 production by CpG motifs in bacterial DNA and synthetic oligodeoxynucleotides" (1998) *J. Immunol.* 161:3930–3935.

Rogers et al., "Recombinant Fel d I: Expression, purification, IgE binding and reaction with cat–allergic human T cells" (1993) *Mol. Immunol.* 30:559–568.

Roget et al., "Synthesis and use of labelled nucleoside phosphoramidite building blocks bearing a reporter group: biotinyl, dinitrophenyl, pyrenyl and dansyl" (1989) *Nucleic Acids Res.* 17:7643–7651.

Roman et al., "Immunostimulatory DNA sequences function as T helper–1–promoting adjuvants" (1997) *Nature Medicine* 3:849–854.

Ruddy et al., "A 1.1–Mb transcript map of the hereditary hemochromatosis locus" (1997) *Genome Res.* 7:441–456.

Ruth, Jerry L., "Oligodeoxynuclotides with reporter groups attached to the base" (1991) *Oligonucleotides and Analogues: A Practical Approach*, Eckstein, ed., IRL Press, pp. 255–282.

Sato et al., "Immunostimulatory DNA sequences necessary for effective intradermal gene immunization" (1996) *Science* 273:352–354.

Schluesener et al., "Protection against generalized autoimmunity of the nervous system (GANS), a novel animal model with combined features of EAE, EAN and EAU by a recombinant HIV–1 $Tat_{37-72}$ peptide–based multiple T cell epitope vaccine" (1997) *FEMS Immunol. Med. Microbiol.* 17:179–186.

Schroeder et al., "Efficacy of oral dalargin–loaded nanoparticle delivery across the blood–brain barrier" (1998) *Peptides* 19:777–780.

Schultz et al., "Oligo–2'–fluoro–2'–deoxynucleotide N3'→P5' phosphoramidates; synthesis and properties" (1996) *Nucleic Acids Res.* 24:2966–2973.

Schwartz et al., "CpG motifs in bacterial DNA cause inflammation in the lower respiratory tract" (1997) *J. Clin. Invest.* 100:68–73.

Segal et al., "Microbial products induce autoimmune disease by an IL–12–dependent pathway" (1997) *J. Immunol.* 158:5087–5090.

*Selected Methods in Cellular Immunology*, Mishell B.B. et al., eds., W. H. Freeman & Co., San Francisco (Table of Contents).

Shimada et al., "In vivo augmentation of natural killer cell activity with a deoxyribonucleic acid fraction of BCG" (1986) *Jpn. J. Cancer Res.* 77:808–816.

Sinha et al., "Oligonucleotides with reporter groups attached to the 5'–terminus" (1991) *Oligonucleotide Analogues: A Practical Approach*, Eckstein, ed., IRL Press, pp. 185–210.

Sonehara et al., "Hexamer palindromic oligonucleotides with 5'–CG–3' motif(s) induce production of interferon" (1996) *J. Interferon and Cytokine Res.* 16:799–803.

Sparwasser et al., "Macrophages sense pathogens via DNA motifs: induction of tumor necrosis factor–60 –mediated shock" (1997) *Eur. J. Immunol.* 27:1671–1679.

Spiegelberg et al., "Inhibition of IgE formation and allergic inflammation by allergen gene immunization and by CpG motif immunostimulatory oligodeoxynuclotides" (1998) *Allergy* 53:93–97.

Stacey et al., "Macrophages ingest and are activated by bacterial DNA" (1996) *J. Immunol.* 157:2116–2122.

Staros et al., "Enhancement by N–hydroxysulfosuccinimide of water–soluble carbodiimide–mediated coupling reactions" (1986) *Anal. Biochem.* 156:220–222.

Stein et al., "Non–antisense effects of oligodeoxynucleotides" (1997) *Antisense Technology*, Ch. 11 pp. 241–264, C. Lichtenstein and W. Nellen, eds., IRL Press.

Stirchak et al., "Uncharged stereoregular nucleic acid analogs: 2. Morpholino nucleoside oligomers with carbamate internucleoside linkages" (1989) *Nucleic Acids Res.* 17:6129–6141.

Szoka, Francis, Jr., "Comparative properties and methods of preparation of lipid vesicles (liposomes)" (1980) *Ann. Rev. Biophys. Bioeng.* 9:467–509.

Takahashi et al., "Induction of $CD8^+$ cytotoxic T cells by immunization with purified HIV–1 envelope protein in ISCOMs" (1990) *Nature* 344:873–875.

Takanami et al., "RNA polymerase nascent product analysis" (1980) *Methods in Enzymology* 65:497–560.

*The Encyclopedia of Molecular Biology*, Sir John Kendrew, ed., Blackwell Science, (Table of Contents).

*The Polymerase Chain Reaction*, (1994) Kary B. Mullis et al., eds., Birkhäuser, (Table of Contents).

Tokunaga et al., "Synthetic oligonucleotides with particular base sequences from the cDNA encoding proteins of *Mycobacterium bovis* BCG induce interferons and activate natural killer cells" (1992) *Microbiol. Immunol.* 36:55–66.

*Transcription and Translation: A Practical Approach*, (1984) Hames, B.D. et al., ed., IRL Press, (Table of Contents).

Tripathy et al., "Immune responses to transgene–encoded proteins limit the stability of gene expression after injection of replication–defective adenovirus vectors" (1996) *Nature Medicine* 2:545–550.

Tung et al., "Preparation of oligonucleotide–peptide conjugates" (1991) *Bioconjug. Chem.* 2:464–465.

Ulmer et al., "Heterologous protection against influenza by injection of DNA encoding a viral protein" (1993) *Science* 259:1745–1749.

van Neerven et al., "T cell epitopes of house dust mite major allergen Der p II" (1993) *J. Immunol.* 151:2326–2335.

Waine et al., "Nucleic acids: Vaccines of the future" (1995) *Parasitology Today* 11:113–116.

Wang et al., "Circular RNA oligonucleotides. Synthesis, nucleic acid binding properties, and a comparison with circular DNAs" (1994) *Nucleic Acids Res.* 22:2326–2333.

Warner et al., "Laboratory methods. Construction and evaluation of an instrument for the automated synthesis of oligodeoxyribonucleotides" (1984) *DNA* 3:401–411.

Watwe et al., "Manufacture of lipsomes: A review" (1995) *Curr. Sci.* 68:715–724.

Weeratna et al., "Reduction of antigen expression from DNA vaccines by coadministered oligodeoxynuclotides" (1998) *Antisense & Nucleic Acid Drug Development* 8:351–356.

Weiner et al., "Immunostimulatory oligodeoxynucleotides containing the CpG motif are effective as immune adjuvants in tumor antigen immunization" (1997) *Proc. Natl. Acad. Sci. USA* 94:10833–10837.

Whitehead et al., "The spindle kinesin–like protein HsEg5 is an autoantigen in systemic lupus erythematosus" (1996) *Arthritis & Rheumatism* 39:1635–1642.

Wooldrige et al., "Immunostimulatory oligodeoxynucleotides containing CpG motifs enhance the efficacy of monoclonal antibody therapy of lymphoma" (1997) *Blood* 89:2994–2998.

Xiang et al., "Manipulation of the immune response to a plasmid–encoded viral antigen by coinoculation with plasmids expressing cytokines" (1995) *Immunity* 2:129–135.

Yamamoto et al., "DNA from bacteria, but not from vertebrates, induces interferons, activates natural killer cells and inhibits tumor growth" (1992a) *Microbiol Immunol.* 36:983–997.

Yamamoto et al., "Unique palindromic sequences in synthetic oligonucleotides are required to induce INF and augment INF–mediated natural killer activity" (1992b) *J. Immunol.* 148:4072–4076.

Yamamoto et al., "Ability of oligonucleotides with certain palindromes to induce interferon production and augment natural killer cell activity is associated with their base length" (1994) *Antisense Res. & Develop.* 4:119–122.

Yamamoto et al., "Synthetic oligonucleotides with certain palindromes stimulate interferon production of human peripheral blood lymphocytes in vitro" (1994) *Jpn. J. Cancer Res.* 85:775–779.

Yanagawa et al., "Analysis of superhelical structures of nucleic acid–lipid conjugates by image processing" (1988) *Nucleic Acids Symp. Series* 19:189–192.

Yi et al., "IFN–$\gamma$ promotes IL–6 and IgM secretion in response to CpG motifs in bacterial DNA and oligodeoxynucleotides" (1996) *J. Immunol.* 156:558–564.

Yi et al., "CpG DNA rescue from anti–IgM–induced WEHI–231 B lymphoma apoptosis via modulation of I$\kappa$B$\alpha$ and I$\kappa$B$\beta$ and sustained activation of nuclear factor–$\kappa$B/c–Rel" (1998a) *J. Immunol.* 160:1240–1245.

Yi et al., "CpG motifs in bacterial DNA activate leukocytes through the pH–dependent generation of reactive oxygen species" (1998b) *J. Immunol.* 160:4755–4761.

Yi et al., "CpG oligodeoxynucleotides rescue mature spleen B cells from spontaneous apoptosis and promote cell cycle entry" (1998c) *J. Immunol.* 160:5898–5906.

Yi et al., "Cutting edge: Rapid induction of mitogen–activated protein kinases by immune stimulatory CpG DNA" (1998d) *J. Immunol.* 161:4493–4497.

Zhao et al., "Effect of different chemically modified oligodeoxynucleotides on immune stimulation" (1996) *Biochem. Pharmacol.* 51:173–182.

Zuckermann et al., "Efficient methods for attachment of thiol specific probes to the 3'–ends of synthetic oligodeoxyribonucleotides" (1987) *Nucleic Acids Res.* 15:5305–5321.

\* cited by examiner

```
                           SEQUENCE LISTING

<160> NUMBER OF SEQ ID NOS: 21

<210> SEQ ID NO 1
    <211> LENGTH: 22
    <212> TYPE: DNA
    <213> ORGANISM: Artificial Sequence
    <220> FEATURE:
    <223> OTHER INFORMATION: Synthetic construct

<400> SEQUENCE: 1
tgaccgtgaa cgttcgagat ga                                           22

<210> SEQ ID NO 2
    <211> LENGTH: 22
    <212> TYPE: DNA
    <213> ORGANISM: Artificial Sequence
    <220> FEATURE:
    <223> OTHER INFORMATION: Synthetic construct

<400> SEQUENCE: 2
tgactgtgaa cgttcgagat ga                                           22

<210> SEQ ID NO 3
    <211> LENGTH: 22
    <212> TYPE: DNA
    <213> ORGANISM: Artificial Sequence
    <220> FEATURE:
    <223> OTHER INFORMATION: Synthetic construct

<400> SEQUENCE: 3
tgactgtgaa ggttagagat ga                                           22

<210> SEQ ID NO 4
    <211> LENGTH: 23
    <212> TYPE: DNA
    <213> ORGANISM: Artificial Sequence
    <220> FEATURE:
    <223> OTHER INFORMATION: Synthetic construct

<400> SEQUENCE: 4
tcatctcgaa cgttccacag tca                                          23

<210> SEQ ID NO 5
    <211> LENGTH: 22
    <212> TYPE: DNA
    <213> ORGANISM: Artificial Sequence
    <220> FEATURE:
    <223> OTHER INFORMATION: Synthetic construct

<400> SEQUENCE: 5
tcatctcgaa cgttcacggt ca                                           22
```

<210> SEQ ID NO 6
<211> LENGTH: 22
<212> TYPE: DNA
<213> ORGANISM: Artificial Sequence
<220> FEATURE:
<223> OTHER INFORMATION: Synthetic construct

<400> SEQUENCE: 6
tgactgtgaa cgttccagat ga                                    22

<210> SEQ ID NO 7
<211> LENGTH: 26
<212> TYPE: DNA
<213> ORGANISM: Artificial Sequence
<220> FEATURE:
<223> OTHER INFORMATION: Synthetic construct

<400> SEQUENCE: 7
tccataacgt tcgcctaacg ttcgtc                                26

<210> SEQ ID NO 8
<211> LENGTH: 22
<212> TYPE: DNA
<213> ORGANISM: Artificial Sequence
<220> FEATURE:
<223> OTHER INFORMATION: Synthetic construct

<400> SEQUENCE: 8
tgactgtgaa cgttagcgat ga                                    22

<210> SEQ ID NO 9
<211> LENGTH: 22
<212> TYPE: DNA
<213> ORGANISM: Artificial Sequence
<220> FEATURE:
<223> OTHER INFORMATION: Synthetic construct

<400> SEQUENCE: 9
tgactgtgaa cgttagacgt ga                                    22

<210> SEQ ID NO 10
<211> LENGTH: 21
<212> TYPE: DNA
<213> ORGANISM: Artificial Sequence
<220> FEATURE:
<223> OTHER INFORMATION: Synthetic construct

<400> SEQUENCE: 10
tgacgtgaac gttagagatg a                                     21

<210> SEQ ID NO 11
<211> LENGTH: 23
<212> TYPE: DNA
<213> ORGANISM: Artificial Sequence
<220> FEATURE:
<223> OTHER INFORMATION: Synthetic construct

<400> SEQUENCE: 11
tgactcgtga acgttagaga tga                                   23

<210> SEQ ID NO 12
<211> LENGTH: 22
<212> TYPE: DNA
<213> ORGANISM: Artificial Sequence
<220> FEATURE:

```
<223> OTHER INFORMATION: Synthetic construct
<220> FEATURE:
<221> NAME/KEY: modified_base
<222> LOCATION: (11)...(11)
<223> OTHER INFORMATION: 5-bromocytosine

<400> SEQUENCE: 12
tgactgtgaa ngttccagat ga                                        22

<210> SEQ ID NO 13
<211> LENGTH: 22
<212> TYPE: DNA
<213> ORGANISM: Artificial Sequence
<220> FEATURE:
<223> OTHER INFORMATION: Synthetic construct

<400> SEQUENCE: 13
tgactgtgaa gcttagagat ga                                        22

<210> SEQ ID NO 14
<211> LENGTH: 22
<212> TYPE: DNA
<213> ORGANISM: Artificial Sequence
<220> FEATURE:
<223> OTHER INFORMATION: Synthetic construct

<400> SEQUENCE: 14
tcactctctt ccttactctt ct                                        22

<210> SEQ ID NO 15
<211> LENGTH: 22
<212> TYPE: DNA
<213> ORGANISM: Artificial Sequence
<220> FEATURE:
<223> OTHER INFORMATION: Synthetic construct
<220> FEATURE:
<221> NAME/KEY: modified_base
<222> LOCATION: (11)...(11)
<223> OTHER INFORMATION: 5-bromocytosine

<400> SEQUENCE: 15
tgactgtgaa ngttcgagat ga                                        22

<210> SEQ ID NO 16
<211> LENGTH: 22
<212> TYPE: DNA
<213> ORGANISM: Artificial Sequence
<220> FEATURE:
<223> OTHER INFORMATION: Synthetic construct
<220> FEATURE:
<221> NAME/KEY: modified_base
<222> LOCATION: (11)...(11)
<223> OTHER INFORMATION: 5-bromocytosine
<220> FEATURE:
<221> NAME/KEY: modified_base
<222> LOCATION: (15)...(15)
<223> OTHER INFORMATION: 5-bromocytosine

<400> SEQUENCE: 16
tgactgtgaa ngttngagat ga                                        22

<210> SEQ ID NO 17
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: modified_base
```

```
<222> LOCATION: (8)...(8)
<223> OTHER INFORMATION: 5-bromocytosine

<400> SEQUENCE: 17
tccatgangt tcgtgatcgt                                           20

<210> SEQ ID NO 18
<211> LENGTH: 20
<212> TYPE: DNA
<213> ORGANISM: Artificial Sequence
<220> FEATURE:
<223> OTHER INFORMATION: Synthetic construct

<400> SEQUENCE: 18
tccataacgt tcctgatgct                                           20

<210> SEQ ID NO 19
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: modified_base
<222> LOCATION: (8)...(8)
<223> OTHER INFORMATION: 5-bromocytosine

<400> SEQUENCE: 19
tccataangt tcgtgatgct                                           20

<210> SEQ ID NO 20
<211> LENGTH: 24
<212> TYPE: DNA
<213> ORGANISM: Artificial Sequence
<220> FEATURE:
<223> OTHER INFORMATION: Synthetic construct
<220> FEATURE:
<221> NAME/KEY: modified_base
<222> LOCATION: (8)...(8)
<223> OTHER INFORMATION: 5-bromocytosine

<400> SEQUENCE: 20
tccataangt tcgcctaacg ttcg                                      24

<210> SEQ ID NO 21
<211> LENGTH: 24
<212> TYPE: DNA
<213> ORGANISM: Artificial Sequence
<220> FEATURE:
<223> OTHER INFORMATION: Synthetic construct
<220> FEATURE:
<221> NAME/KEY: modified_base
<222> LOCATION: (8)...(8)
<223> OTHER INFORMATION: 5-bromocytosine

<400> SEQUENCE: 21
tccataangt tcgcctaacg ttcg                                      24
```

IMMUNOSTIMULATORY OLIGONUCLEOTIDES, COMPOSITIONS THEREOF AND METHODS OF USE THEREOF

CROSS-REFERENCE TO RELATED APPLICATIONS

This is a continuation-in-part application of U.S. Ser. No. 09/092,329, filed Jun. 5, 1998, now abandoned, which claims the priority benefit of U.S. Provisional Patent Application No. 60/048,793, filed Jun. 6, 1997, both of which are incorporated by reference in their entirety.

STATEMENT OF RIGHTS TO INVENTIONS MADE UNDER FEDERALLY SPONSORED RESEARCH

Not applicable.

1. Technical Field

The present invention relates to immunomodulatory compositions comprising an immunostimulatory oligonucleotide sequence (ISS). The invention further relates to immunomodulatory compositions comprising an ISS in which at least one base has been substituted with a base modified by the addition to C-5 or C-6 on cytosine with an electron-withdrawing moiety. It also relates to the administration of the oligonucleotide sequences to modulate at least one immune response. The invention further relates to in vitro screening methods to identify oligonucleotides with potential immunomodulatory activity.

2. Background Art

The type of immune response generated to infection or other antigenic challenge can generally be distinguished by the subset of T helper (Th) cells involved in the response. The Th1 subset is responsible for classical cell-mediated functions such as delayed-type hypersensitivity and activation of cytotoxic T lymphocytes (CTLs), whereas the Th2 subset functions more effectively as a helper for B-cell activation. The type of immune response to an antigen is generally determined by the cytokines produced by the cells responding to the antigen. Differences in the cytokines secreted by Th1 and Th2 cells are believed to reflect different biological functions of these two subsets.

The Th1 subset may be particularly suited to respond to viral infections and intracellular pathogens because it secretes IL-2 and IFN-γ, which activate CTLs. The Th2 subset may be more suited to respond to free-living bacteria and helminthic parasites and may mediate allergic reactions, since IL-4 and IL-5 are known to induce IgE production and eosinophil activation, respectively. In general, Th1 and Th2 cells secrete distinct patterns of cytokines and so one type of response can moderate the activity of the other type of response. A shift in the Th1/Th2 balance can result in an allergic response, for example, or, alternatively, in an increased CTL response.

Immunization of a host animal against a particular antigen has been accomplished traditionally by repeatedly vaccinating the host with an immunogenic form of the antigen. While most current vaccines elicit effective humoral (antibody, or "Th2-type") responses, they fail to elicit cellular responses (in particular, major histocompatibility complex (MHC) class I-restricted CTL, or "Th1-type" responses) which are generally absent or weak. For many infectious diseases, such as tuberculosis and malaria, Th2-type responses are of little protective value against infection. Moreover, antibody responses are inappropriate in certain indications, most notably in allergy where an antibody response can result in anaphylactic shock. Proposed vaccines using small peptides derived from the target antigen and other currently used antigenic agents that avoid use of potentially infective intact viral particles, do not always elicit the immune response necessary to achieve a therapeutic effect. The lack of a therapeutically effective human immunodeficiency virus (HIV) vaccine is an unfortunate example of this failure.

Protein-based vaccines typically induce Th2-type immune responses, characterized by high titers of neutralizing antibodies but without significant cell-mediated immunity. In contrast, intradermal delivery of "naked", or uncomplexed, DNA encoding an antigen stimulates immune responses to the antigen with a Th1-type bias, characterized by the expansion of $CD4^+$ T cells producing IFN-γ and cytotoxic $CD8^+$ T cells. Manickan et al. (1995) *J. Immunol.* 155:250–265; Xiang et al. (1995) *Immunity* 2:129–135; Raz et al. (1995) *Proc. Natl. Acad. Sci. USA* 93:5141–5145; and Briode et al. (1997) *J. Allergy Clin. Immunol.* 99:s129. Injection of antigen-encoding naked DNA reproducibly induces both humoral and cellular immune responses against the encoded antigens. Pardoll and Beckerleg (1995) *Immunity* 3:165–169. DNA vaccines can provide a new approach to infectious disease prophylaxis. See, for instance, Dixon (1995) *Bio/Technology* 13:420 and references cited therein.

Certain types of DNA, without being translated, have been shown to stimulate immune responses. Bacterial DNA induces anti-DNA antibodies in injected mice, as well as cytokine production by macrophage and natural killer (NK) cells. Pisetsky (1996) *J. Immunol.* 156:421–423; Shimada et al. (1986) *Jpn. J. Cancer Res.* 77:808–816; Yamamoto et al. (1992a) *Microbiol. Immunol.* 36:983–897; and Cowdery et al. (1996) *J. Immunol.* 156:4570–4575.

B cell and NK cell activation properties of bacterial DNA have been associated with short (6 base pair hexamer) sequences that include a central unmethylated CpG dinucleotide. Yamamoto et al. (1992a); and Krieg et al. (1995) *Nature* 374:546–549. Oligonucleotides comprising a CpG sequence flanked by two 5' purines and two 3' pyrimidines have been shown to be most potent in B cell and NK cell stimulation. For example, when a variety of oligonucleotides comprising hexamers were tested for their ability to augment the NK cell activity of mouse spleen cells, the most immunogenic hexamers included AACGTT, AGCGCT, GACGTC. Yamamoto et al. (1992b) *J. Immunol.* 148:4072–4076. In a study in which B cell activation was measured in response to oligonucleotides, the most stimulatory hexamer sequences (e.g., AACGTC, AACGTT, GACGTC, GACGTT) also matched the sequence of 5'-purine, purine, CG, pyrimidine, pyrimidine-3'. Krieg et al. (1995). However, as shown herein, this prototypical hexamer sequence is found in many oligonucleotides that are not immunostimulatory. Thus, the prototypical hexamer sequence proposed by Krieg et al. (1995) is not predictive of immunostimulatory activity.

Bacterial DNA stimulated macrophages to produce IL-12 and TNF-α. These macrophage-produced cytokines were found to induce the production of IL-12 and IFN-γ from splenocytes. Halpern et al. (1996) *Cell. Immunol.* 167:72–78. In vitro treatment of splenocytes with either bacterial DNA or CpG containing oligonucleotides induced the production of IL-6, IL-12 and IFN-γ. Klinman et al. (1996) *Proc. Natl. Acad. Sci. USA* 93:2879–2883. Production of all of these cytokines is indicative of induction of a Th1-type immune response rather than a Th2-type response.

To date, no clear consensus has been reached on the sequences both necessary and sufficient of immune stimulation. A recent study which examined induction of NK activity in response to CpG containing-oligonucleotides suggested that the unmethylated CpG motif was necessary but not sufficient for oligonucleotide induction of NK lytic activity. Ballas et al. (1996) *J. Immunol.* 157:1840–1845. Sequences flanking the CpG appeared to influence the immunostimulatory activity of an oligonucleotide. Immunostimulatory activity of immunostimulatory sequences appears to be independent of adenosine-methylation, and whether the nucleotide is single or double-stranded. See, for example, Tokunaga et al. (1989) *Microbiol. Immunol.* 33:929; Tokunaga et al. (1992) *Microbiol. Immunol.* 36:55–66; Yamamoto et al. (1992b); Messina et al. (1993) *Cell. Immunol.* 147:148–157; and Sato et al. (1996) *Science* 273:352–354. Oligonucleotide length also does not seem to be a factor, as double-stranded DNA 4 kb long (Sato et al. (1996)) or single-stranded DNA as short as 15 nucleotides in length (Ballas et al. (1996)) illicited immune responses; though if oligonucleotide length was reduced below 8 bases or if the DNA was methylated with CpG methylase, immunostimulatory activity was abolished. Krieg et al. (1995).

Allergic responses, including those of allergic asthma, are characterized by an early phase response, which occurs within seconds to minutes of allergen exposure and is characterized by cellular degranulation, and a late phase response, which occurs 4 to 24 hours later and is characterized by infiltration of eosinophils into the site of allergen exposure. Specifically, during the early phase of the allergic response, activation of Th2-type lymphocytes stimulates the production of antigen-specific IgE antibodies, which in turn triggers the release of histamine and other mediators of inflammation from mast cells and basophils. During the late phase response, IL-4 and IL-5 production by CD4$^+$ Th2 cells is elevated. These cytokines appear to play a significant role in recruiting eosinophils into site of allergen exposure, where tissue damage and dysfunction result.

Antigen immunotherapy for allergic disorders involves the subcutaneous injection of small, but gradually increasing amounts, of antigen. Such immunization treatments present the risk of inducing IgE-mediated anaphylaxis and do not address the cytokine-mediated events of the allergic late phase response.

Vaccination with certain DNA containing immunostimulatory motifs induces an immune response with a Th1-type bias. For example, mice injected intradermally with *Escherichia coli* (*E. coli*) β-galactosidase (β-Gal) in saline or in the adjuvant alum responded by producing specific IgG1 and IgE antibodies, and CD4$^+$ cells that secreted IL-4 and IL-5, but not IFN-γ, demonstrating that the T cells were predominantly of the Th2 subset. However, mice injected intradermally (or with a tyne skin scratch applicator) with plasmid DNA (in saline) encoding β-Gal and containing an ISS responded by producing IgG2a antibodies and CD4$^+$ cells that secreted IFN-γ, but not IL-4 and IL-5, demonstrating that the T cells were predominantly of the Th1 subset. Moreover, specific IgE production by the plasmid DNA-injected mice was reduced 66–75%. Raz et al. (1996) *Proc. Natl. Acad. Sci. USA* 93:5141–5145. In general, the response to naked DNA immunization is characterized by production of IL-2, TNFα and IFN-γ by antigen-stimulated CD4$^+$ T cells, which is indicative of a Th1-type response. This is particularly important in treatment of allergy and asthma as shown by the decreased IgE production.

In another example, the presence of an immunostimulatory sequence, such as the palindromic hexamer AACGTT, in an antigen-encoding plasmid vector injected intradermally prompted the production of large amounts of IFN-α, IFN-β and IL-12. Sato et al. (1996). IFN-α plays a role in the differentiation of naive T cells toward a Th1-type phenotype, antagonizes Th2 cells, inhibits IgE synthesis, promotes IgG2a production and induces a Th1 phenotype of antigen-specific T cell clones. IL-12 promotes IFN-γ production by T cells and favors maturation of Th1 cells.

It would be useful in treatment of a wide variety of indications to be able to specifically enhance the Th1-type response to a particular antigen while down-regulating the Th2-type response to the same antigen. Treatment or palliation of these indications includes, but is not limited to, tumor therapy, treatment of allergic disorders and induction of a vigorous cellular immune response. The present invention provides compositions comprising oligonucleotide sequences that can be employed in these contexts.

All of the cited literature included in the preceding section, as well as the cited literature included in the following disclosure, are hereby incorporated herein by reference.

DISCLOSURE OF THE INVENTION

The present invention provides immunomodulatory compositions comprising an oligonucleotide that contains at least one immunostimulatory (ISS) octanucleotide.

In a preferred embodiment, the ISS octanucleotide comprises the sequence 5'-Purine, Purine, Cytosine, Guanine, Pyrimidine, Pyrimidine, Cytosine, Cytosine-3'.

In another preferred embodiment, the ISS octanucleotide comprises the sequence 5'-Purine, Purine, Cytosine, Guanine, Pyrimidine, Pyrimidine, Cytosine, Guanine-3'.

In a further embodiment, the ISS octanucleotide is selected from AACGTTCC, AACGTTCG, GACGTTCC and GACGTTCG.

In another embodiment, at least one of the cytosines of the ISS octanucleotide sequence is substituted with a modified cytosine, wherein the modified cytosine comprises an addition of an electron-withdrawing group to at least C-5 and/or C-6. Preferably, the modified cytosine is 5'-bromocytidine. Preferably, the C at the third position from the 5' end of the ISS octanucleotide is substituted with a 5'-bromocytidine.

In another embodiment, the immunomodulatory composition comprises an oligonucleotide that contains at least one ISS octanucleotide and an antigen.

In a further embodiment, the antigen is selected from the group consisting of proteins, glycoproteins, polysaccharides, and lipids.

In another embodiment, the antigen is conjugated to the ISS oligonucleotide.

In another embodiment, the immunomodulatory composition comprises an oligonucleotide that contains at least one immunostimulatory (ISS) octanucleotide and a facilitator selected from the group consisting of co-stimulatory molecules, cytokines, chemokines, targeting protein ligand, a trans-activating factor, a peptide, and a peptide comprising a modified amino acid.

In another embodiment, the immunomodulatory composition comprises an oligonucleotide that contains at least one ISS octanucleotide, an antigen, and an adjuvant.

In another embodiment, an immunomodulatory composition comprises an immunomodulatory oligonucleotide and an antigen proximately associated at a distance effective to enhance an immune response.

In another embodiment, an immunomodulatory composition comprises an immunomodulatory oligonucleotide and an antigen proximately associated to co-deliver the oligonucleotide and the antigen to an immune target.

In another embodiment, an immunomodulatory composition comprises an immunomodulatory oligonucleotide and the antigen associated with an adjuvant. Further, the immunomodulatory oligonucleotide and the antigen are associated in microparticles. In another embodiment, the immunomodulatory oligonucleotide and the antigen are associated in liposomes.

The invention also provides for methods of modulating an immune response comprising the administration of an immunomodulatory composition comprising an antigen and an oligonucleotide that contains at least one ISS octanucleotide.

In a further embodiment, the immune response modulation comprises the induction of a Th1 response.

The invention also provides for a method of modulating an immune response comprising the administration of an immunomodulatory composition comprising an immunomodulatory facilitator and an oligonucleotide that contains at least one ISS.

The invention also provides for a method of screening for human immunostimulatory activity of oligonucleotides comprising the steps of: (a) providing macrophage cells and an aliquot of the oligonucleotide to be tested; (b) incubating the cells and oligonucleotide of step a) for an appropriate length of time; and (c) determining the relative amount of Th1-biased cytokines in the cell culture supernatant.

The invention also provides for a methods of treating individuals in need of immune modulation comprising administration of a composition comprising an immunomodulatory oligonucleotide that contains at least one ISS, including, but not limited to, individuals suffering from cancer, allergic diseases and infectious diseases. Further embodiments provide methods from treating individuals infected with hepatitis B virus, papillomavirus, and human immunodeficiency virus.

In another embodiment, the invention provides methods of preventing an infectious disease in an individual comprising administration of an immunomodulatory composition comprising and ISS and antigen.

Further embodiments include methods of preventing infectious disease due to viral infection, including, but not limited to, those diseases due to infection by hepatitis B virus, influenza virus, herpes virus, human immunodeficiency virus and papillomavirus.

Further embodiments include methods of preventing infectious disease due to bacterial infection, including, but not limited to, those diseases due to infection by *Hemophilus influenza*, *Mycobacterium tuberculosis* and *Bordetella pertussis*.

Further embodiments include methods of preventing infectious disease due to parasitic infection, including, but not limited to, those diseases due to infection by malarial plasmodia, Leishmania species, Trypanosoma species and Schistosoma species.

MODES FOR CARRYING OUT THE INVENTION

Figure 1:
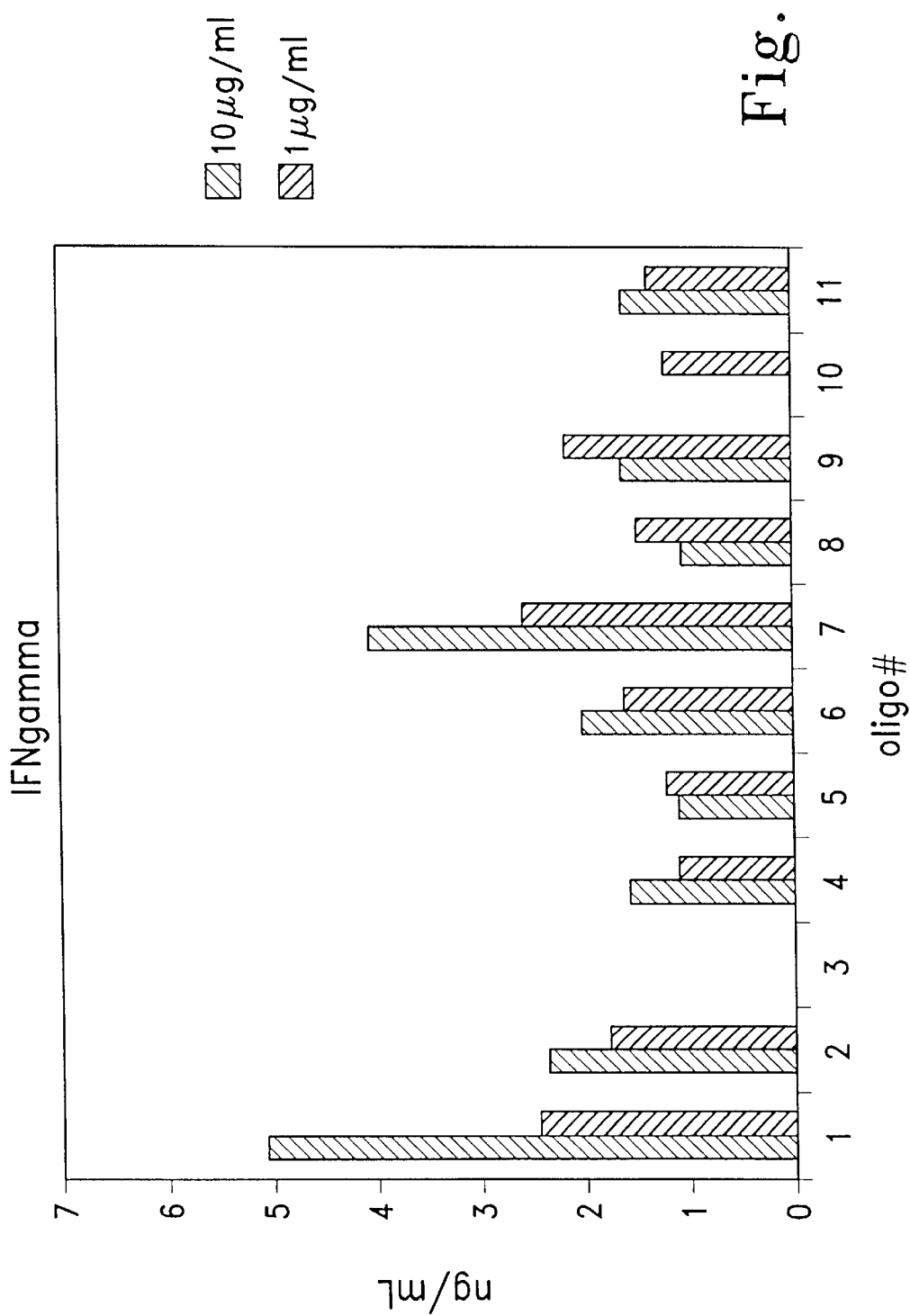
FIG. 1 is a graph depicting the level of IFN-γ found in the culture supernatant of splenocytes after exposure to oligonucleotides for 48 hours. See Table 1 for identification of oligonucleotides.

It has now been found that a particular set of octanucleotide sequences within oligonucleotide sequences renders the oligonucleotide capable of modulating an immune response. Such oligonucleotide sequences comprise an immunostimulatory octanucleotide sequence (ISS). Compositions of the invention comprise the ISS octanucleotide-containing oligonucleotide alone or in conjunction with a immunomodulatory agent, such as a peptide, an antigen and/or an additional adjuvant. The oligonucleotides themselves have been found to have adjuvant activity and are suitable for use as adjuvants alone and have also been found to potentiate the effect of another adjuvant.

Previously described immunostimulatory sequences have been defined as containing a hexamer sequence with a central CpG dinucleotide. Unfortunately, relying on the hexamer sequence to predict immunostimulatory activity yields, for the most part, immunologically inactive oligonucleotides. For instance, as shown in Example 1, 5 different oligonucleotides with the hexamer AACGTT had clearly demonstrable immunostimulatory activity whereas 5 other oligonucleotides with AACGTT had much reduced immunostimulatory activity. Thus, the previous hexamer algorithm is not predictive of immunostimulatory activity.

The ISS of the present invention comprise an octanucleotide sequence which comprises the previously described hexamer and two additional nucleotides 3' of the hexamer. Preferably, the ISS octamer comprises 5'-purine, purine, cytosine, guanine, pyrimidine, pyrimidine, cytosine, guanine-3' or the ISS octamer comprises 5'-purine, purine, cytosine, guanine, pyrimidine, pyrimidine, cytosine, cytosine-3'. More preferably, the ISS octanucleotide comprises 5'-GACGTTCG-3' or 5'-GACGTTCC-3'. Still more preferably, the ISS octanucleotide comprises 5'-AACGTTCG-3' or 5'-AACGTTCC-3'. The present invention demonstrates that, relative to the hexameric ISS sequence, the ISS octanucleotide is a reliable predictor of immunostimulatory activity in oligonucleotides.

In another embodiment, the ISS oligonucleotide of the present invention can also comprise a CG dinucleotide in which the C residue is modified by addition to C-5 and/or C-6 of an electron-withdrawing moiety ("modified ISS"). When the same cytosine is methylated, all immunostimulatory activity of the oligonucleotide is lost. Preferably, in such compositions, the cytosine in the third position from the 5' end can be substituted with a cytosine analog, preferably 5-bromocytidine, fluorinated cytosine, or chlorinated cytosine. Some of the modified ISS have approximately the same, if not greater, immunostimulatory activity relative to the same sequence without a modified base.

The ISS oligonucleotide of the present invention can comprise any other physiologically acceptable modified nucleotide base.

The invention also provides a method and compositions for a general stimulation of an immune response through the adjuvant-like effect of an administered ISS.

The invention also provides compositions for the enhancement of an immune response which comprise an ISS-antigen conjugate. An ISS-antigen conjugate can be formed through covalent and/or non-covalent interactions between the ISS and the antigen.

The invention also provides compositions which comprise an ISS-antigen admixture in which the ISS and the antigen are proximately associated at a distance effective to enhance an immune response compared to the co-administration of the ISS and antigen in solution. The invention further provides compositions which comprise an encapsulating agent that can maintain the ISS and antigen in proximate association until the ISS-antigen complex is available to the target. In an ISS-antigen admixture, the ISS and antigen are maintained in proximate association such that both ISS and antigen can be taken up by the same target cell. Further, ISS and antigen in an admixture are maintained at concentrations effective to modulate an immune response. Preferably, the ISS and antigen are proximately associated at a distance of about 0.04 μm to about 100 μm, more preferably, at a distance of about 0.1 μm to about 20 μm, even more preferably, at a distance of about 0.15 μm to about 10 μm. Targets of the ISS-antigen conjugate or the ISS-antigen admixture include, but are not limited to, antigen presenting cells (APCs), such as macrophages, dendritic cells, and/or lymphocytes, lymphatic structures, such as lymph nodes and/or the spleen, and nonlymphatic structures, particularly those in which dendritic cells are found, such as skin, lungs, and/or gastrointestinal tract.

Enhancement of an immune response by a composition in which an ISS and an immunomodulatory agent are proximately associated refers to a modulation of an immune response following administration of said composition as compared to the immune response following administration of the ISS and immunomodulatory agent freely soluble with respect to each other. Enhancement of an immune response includes modulation of an immune response including, but not limited to, stimulation, suppression and a shift in the type of immune response, for instance, between a Th1-type response and a Th2-type response.

The invention also provides for compositions which comprise an ISS-antigen conjugate or an ISS-antigen admixture and an adjuvant where, upon co-administration, the association of ISS-antigen and adjuvant is effective to enhance an immune response compared to the co-administration of the ISS-antigen without adjuvant. In such compositions, the adjuvant is maintained in association with ISS-antigen so as to recruit and activate target cells to the ISS-antigen.

The present invention also provides methods for the use of ISS in conjunction with an antigen in stimulation of an immune response. Preferably, as used in such methods, the ISS provides an adjuvant-like activity in the generation of a Th1-type immune response to the antigen.

Preferably, the immune response stimulated according to the invention is biased toward the Th1-type phenotype and away from the Th2-type phenotype. With reference to the invention, stimulating a Th1-type immune response can be determined in vitro or ex vivo by measuring cytokine production from cells treated with ISS as compared to those treated without ISS. Methods to determine the cytokine production of cells include those methods described herein and any known in the art. The type of cytokines produced in response to ISS treatment indicate a Th1-type or a Th2-type biased immune response by the cells. As used herein, the term "Th1-type biased" cytokine production refers to the measurable increased production of cytokines associated with a Th1-type immune response in the presence of a stimulator as compared to production of such cytokines in the absence of stimulation. Examples of such Th1-type biased cytokines include, but are not limited to, IL-2, IL-12, and IFN-γ. In contrast, "Th2-type biased cytokines" refers to those associated with a Th2-type immune response, and include, but are not limited to, IL-4, IL-5, IL-10 and IL-13. Cells useful for the determination of ISS activity include cells of the immune system, primary cells isolated from a host and/or cell lines, preferably APCs and lymphocytes, even more preferably macrophages and T cells.

Stimulating a Th1-type immune response can also be measured in a host treated with an ISS-antigen composition and can be determined by any method known in the art including, but not limited to: (1) a reduction in levels of IL-4 measured before and after antigen-challenge; or detection of lower (or even absent) levels of IL-4 in an ISS-antigen treated host as compared to an antigen-primed, or primed and challenged, control treated without ISS; (2) an increase in levels of IL-12, IL-18 and/or IFN (α, β or γ) before and after antigen challenge; or detection of higher levels of IL-12, IL-18 and/or IFN (α, β or γ) in an ISS-antigen treated host as compared to an antigen-primed or, primed and challenged, control treated without ISS; (3) IgG2a antibody production in an ISS-antigen treated host as compared to a control treated without ISS; and/or (4) a reduction in levels of antigen-specific IgE as measured before and after antigen challenge; or detection of lower (or even absent) levels of antigen-specific IgE in an ISS-antigen treated host as compared to an antigen-primed, or primed and challenged, control treated without ISS. A variety of these determinations can be made by measuring cytokines made by APCs and/or lymphocytes, preferably macrophages and/or T cells, in vitro or ex vivo using methods described herein or any known in the art. Methods to determine antibody production include any known in the art.

The Th1-type biased cytokine induction which occurs as a result of ISS administration produces enhanced cellular immune responses, such as those performed by NK cells, cytotoxic killer cells, Th1 helper and memory cells. These responses are particularly beneficial for use in protective or therapeutic vaccination against viruses, fungi, protozoan parasites, bacteria, allergic diseases and asthma, as well as tumors.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); and "Current Protocols in Immunology" (J. E. Coligan et al., eds., 1991).

Compositions Comprising ISS

A composition of the subject invention is an ISS that is capable of eliciting a desired immune response. The term "ISS" as used herein refers to oligonucleotide sequences that effect a measurable immune response as measured in vitro, in vivo and/or ex vivo. Examples of measurable immune responses include, but are not limited to, antigen-specific antibody production, secretion of cytokines, activation or expansion of lymphocyte populations such as NK cells, $CD4^+$ T lymphocytes, $CD8^+$T lymphocytes, B lymphocytes, and the like. Preferably, the ISS sequences preferentially activate a Th1-type response. The oligonucleotide of the composition contains at least one octameric ISS.

The octameric ISS preferably comprises a CG containing sequence of the general octameric sequence 5'-Purine, Purine, Cytosine, Guanine, Pyrimidine, Pyrimidine, Cytosine, (Cytosine or Guanine)-3'. As is readily evident to one skilled in the art, this class of sequences encompasses the following: GACGTTCC; GACGCTCC; GACGTCCC; GACGCCCC; AGCGTTCC; AGCGCTCC; AGCGTCCC; AGCGCCCC; AACGTTCC; AACGCTCC; AACGTCCC; AACGCCCC; GGCGTTCC; GGCGCTCC; GGCGTCCC; GGCGCCCC; GACGTTCG; GACGCTCG; GACGTCCG; GACGCCCG; AGCGTTCG; AGCGCTCG; AGCGTCCG; AGCGCCCG; AACGTTCG; AACGCTCG; AACGTCCG; AACGCCCG; GGCGTTCG; GGCGCTCG; GGCGTCCG; GGCGCCCG. Most preferably, the ISS comprises an octamer selected from the group consisting of: AACGTTCC, AACGTTCG, GACGTTCC, and GACGTTCG.

Where the immunostimulatory oligonucleotide comprises an RNA sequence, the ISS preferably comprises a single-stranded or double-stranded sequence selected from the group consisting of AACGUUCC, AACGUUCG, GACGUUCC, and GACGUUCG.

In accordance with the present invention, the oligonucleotide contains at least one ISS, and can contain multiple ISSs. The ISSs can be adjacent within the oligonucleotide, or they can be separated by additional nucleotide bases within the oligonucleotide.

As used interchangeably herein, the terms "oligonucleotide" and "polynucleotide" include single-stranded DNA (ssDNA), double-stranded DNA (dsDNA), single-stranded RNA (ssRNA) and double-stranded RNA (dsRNA), modified oligonucleotides and oligonucleosides or combinations thereof. The oligonucleotide can be linearly or circularly configured, or the oligonucleotide can contain both linear and circular segments.

The ISS can be of any length greater than 6 bases or base pairs, preferably greater than 15 bases or basepairs, more preferably greater than 20 bases or base pairs in length.

In general, dsRNA exerts an immunostimulatory effect and is encompassed by the invention. Modifications of ISS include any known in the art, but are not limited to, modifications of the 3'OH or 5'OH group, modifications of the nucleotide base, modifications of the sugar component, and modifications of the phosphate group. Various such modifications are described below.

Modified Bases and Base Analogs

Oligonucleotides are polymers of nucleosides joined, generally, through phosphoester linkages. A nucleoside consists of a purine (adenine or guanine or derivative thereof) or pyrimidine (thymine, cytosine or uracil, or derivative thereof) base bonded to a sugar. The four nucleoside units (or bases) in DNA are called deoxyadenosine, deoxyguanosine, deoxythymidine, and deoxycytidine. A nucleotide is a phosphate ester of a nucleoside.

Multiple bases, sugars, or phosphates in any combination can be substituted in the ISS.

The oligonucleotide of the invention can comprise ribonucleotides (containing ribose as the only or principal sugar component), deoxyribonucleotides (containing deoxyribose as the principal sugar component), or, in accordance with the state of the art, modified sugars or sugar analogs can be incorporated in the ISS. Thus, in addition to ribose and deoxyribose, the sugar moiety can be pentose, deoxypentose, hexose, deoxyhexose, glucose, arabinose, xylose, lyxose, and a sugar "analog" cyclopentyl group. The sugar can be in pyranosyl or in a furanosyl form. In the ISS, the sugar moiety is preferably the filranoside of ribose, deoxyribose, arabinose or 2'-0-methylribose, and the sugar can be attached to the respective heterocyclic bases either in $\alpha$ or $\beta$ anomeric configuration. The preparation of these sugars or sugar analogs and the respective "nucleosides" wherein such sugars or analogs are attached to a heterocyclic base (nucleic acid base) per se is known, and need not be described here, except to the extent such preparation can pertain to any specific example.

The phosphorous derivative (or modified phosphate group) which can be attached to the sugar or sugar analog moiety in the oligonucleotides of the present invention can be a monophosphate, diphosphate, triphosphate, alkylphosphate, alkanephosphate, phosphorothioate, phosphorodithioate or the like. A phosphorothiate linkage can be used in place of a phosphodiester linkage. The preparation of the above-noted phosphate analogs, and their incorporation into nucleotides, modified nucleotides and oligonucleotides, per se, is also known and need not be described here in detail. Peyrottes et al. (1996) *Nucleic Acids Res.* 24:1841–1848; Chaturvedi et al. (1996) *Nucleic Acids Res.* 24:2318–2323; and Schultz et al. (1996) *Nucleic Acids Res.* 24:2966–2973. Preferably, oligonucleotides of the present invention comprise phosphorothioate linkages. Oligonucleotides with phosphorothioate backbones can be more immunogenic than those with phosphodiester backbones and appear to be more resistant to degradation after injection into the host. Braun et al. (1988) *J. Immunol.* 141:2084–2089; and Latimer et al. (1995) *Mol. Immunol.* 32:1057–1064.

The heterocyclic bases, or nucleic acid bases, which are incorporated in the ISS can be the naturally-occurring principal purine and pyrimidine bases, (namely uracil or thymine, cytosine, adenine and guanine, as mentioned above), as well as naturally-occurring and synthetic modifications of said principal bases.

Those skilled in the art will recognize that a large number of "synthetic" non-natural nucleosides comprising various heterocyclic bases and various sugar moieties (and sugar analogs) are available in the art, and that as long as other criteria of the present invention are satisfied, the ISS can include one or several heterocyclic bases other than the principal five base components of naturally-occurring nucleic acids. Preferably, however, the heterocyclic base in the ISS includes, but is not limited to, uracil-5-yl, cytosin-5-yl, adenin-7-yl, adenin-8-yl, guanin-7-yl, guanin-8-yl, 4-aminopyrrolo[2.3-d]pyrimidin-5-yl, 2-amino-4-oxopyrolo[2,3-d]pyrimidin-5-yl, 2-amino-4-oxopyrrolo[2.3-d]pyrimidin-3-yl groups, where the purines are attached to the sugar moiety of the ISS via the 9-position, the pyrimidines via the 1-position, the pyrrolopyrimidines via the 7-position and the pyrazolopyrimidines via the 1-position.

In one embodiment, the ISS comprises at least one modified base. As used herein, the term "modified base" is synonymous with "base analog", for example, "modified cytosine" is synonymous with "cytosine analog." Similarly, "modified" nucleosides or nucleotides are herein defined as being synonymous with nucleoside or nucleotide "analogs." In a preferred embodiment, a cytosine of the ISS is substituted with a cytosine modified by the addition to C-5 and/or C-6 on cytosine with an electron-withdrawing moiety. Preferably, the electron-withdrawing moiety is a halogen. Such modified cytosines can include, but are not limited to, azacytosine, 5-bromocytosine, bromouracil, 5-chlorocytosine, chlorinated cytosine, cyclocytosine, cytosine arabinoside, fluorinated cytosine, fluoropyrimidine, fluorouracil, 5,6-dihydrocytosine, halogenated cytosine, halogenated pyrimidine analogue, hydroxyurea, iodouracil, 5-nitrocytosine, uracil, and any other pyrimidine analog or modified pyrimidine.

Methods of Modulating Immune Responses with ISS

In one embodiment, the invention provides compositions comprising ISS as the only immunologically active substance. Upon administration, such ISS induces a stimulation of the immune system.

In other embodiments, ISS-can be administered in conjunction with one or more members of the group of immunomodulatory molecules comprising antigens (including, but not limited to, proteins, glycoproteins, polysaccharides, and lipids), and/or immunomodulatory facilitators such as co-stimulatory molecules (including, but not limited to, cytokines, chemokines, targeting protein ligand, transactivating factors, peptides, and peptides comprising a modified amino acid) and adjuvants (including but not limited to, alum, lipid emulsions, and polylactide/polyglycolide microparticles). The term "immunomodulatory" as used herein includes immunostimulatory as well as immunosuppressive effects. Immunostimulatory effects include, but are not limited to, those that directly or indirectly enhance cellular or humoral immune responses. Examples of immunostimulatory effects include, but are not limited to, increased antigen-specific antibody production; activation or proliferation of a lymphocyte population such as NK cells, $CD4^+$ T lymphocytes, $CD8^+$ T lymphocytes, macrophages and the like; increased synthesis of immunostimulatory cytokines including, but not limited to, IL-1, IL-2, IL-4, IL-5, IL-6, IL-12, IFN-γ, TNF-α and the like. Immunosuppressive effects include those that directly or indirectly decrease cellular or humoral immune responses. Examples of immunosuppressive effects include, but are not limited to, a reduction in antigen-specific antibody production such as reduced IgE production; activation of lymphocyte or other cell populations that have immunosuppressive activities such as those that result in immune tolerance; and increased synthesis of cytokines that have suppressive effects toward certain cellular functions. One example of this is IFN-γ, which appears to block IL-4 induced class switch to IgE and IgG1, thereby reducing the levels of these antibody subclasses.

The ISS and the antigen and/or immunomodulatory facilitator can be administered together in the form of a conjugate or co-administered in an admixture sufficiently close in time so as to modulate an immune response. Preferably, the ISS and immunomodulatory molecule are administered simultaneously. The term "co-administration" as used herein refers to the administration of at least two different substances sufficiently close in time to modulate an immune response. Preferably, co-administration refers to simultaneous administration of at least two different substances.

As used herein, the term "conjugate" refers to a complex in which an ISS and an immunomodulatory molecule are linked. Such conjugate linkages include covalent and/or non-covalent linkages.

As used herein, the term "antigen" means a substance that is recognized and bound specifically by an antibody or by a T cell antigen receptor. Antigens can include peptides, proteins, glycoproteins, polysaccharides, gangliosides and lipids; portions thereof and combinations thereof. The antigens can be those found in nature or can be synthetic. Haptens are included within the scope of "antigen." A hapten is a low molecular weight compound that is not immunogenic by itself but is rendered immunogenic when conjugated with an immunogenic molecule containing antigenic determinants.

As used herein, the term "adjuvant" refers to a substance which, when added to an immunogenic agent, nonspecifically enhances or potentiates an immune response to the agent in the recipient host upon exposure to the mixture.

In the stimulation of an immune response, most adjuvants have generally been found to stimulate macrophages at the site of injection. As described herein, ISS have been shown to stimulate cytokine production from macrophage cells and, as such, immunostimulatory polynucleotides function as adjuvants. Thus, in another embodiment, the invention provides compositions comprising ISS and an antigen. Antigens suitable for administration with ISS include any molecule capable of eliciting a B cell or T cell antigen-specific response. Preferably, antigens elicit an antibody response specific for the antigen. A wide variety of molecules are antigens. These include, but are not limited to, sugars, lipids and polypeptides, as well as macromolecules such as complex carbohydrates, and phospholipids. Small molecules may need to be haptenized in order to be rendered antigenic. Preferably, antigens of the present invention include peptides, lipids (e.g. sterols, fatty acids, and phospholipids), polysaccharides such as those used in *Hemophilus influenza* vaccines, gangliosides and glycoproteins.

As used herein, the term "peptide" includes peptides and proteins that are of sufficient length and composition to effect a biological response, e.g. antibody production or cytokine activity whether or not the peptide is a hapten. Typically, the peptides are of at least six amino acid residues in length. The term "peptide" further includes modified amino acids, such modifications including, but not limited to, phosphorylation, glycosylation, pegylation, lipidization and methylation.

In one embodiment, the invention provides compositions comprising ISS and antigenic peptides. Antigenic peptides can include purified native peptides, synthetic peptides, recombinant proteins, crude protein extracts, attenuated or inactivated viruses, cells, micro-organisms, or fragments of such peptides.

Many antigenic peptides and proteins are known, and available in the art; others can be identified using conventional techniques. Protein antigens that can serve as immunomodulatory facilitators include, but are not limited to, the following examples. Isolated native or recombinant antigens can be derived from plant pollens (see, for example, Rafnar et al. (1991) *J. Biol. Chem.* 266:1229–1236; Breiteneder et al. (1989) *EMBO J.* 8:1935–1938; Elsayed et al. (1991) *Scand. J. Clin. Lab. Invest. Suppl.* 204:17–31; and Malley (1989) *J. Reprod. Immunol.* 16:173–186), dust mite proteins (see, for example, Chua et al. (1988) *J. Exp. Med.* 167:175–182; Chua et al. (1990) *Int. Arch. Allergy Appl. Immunol.* 91:124–129; and Joost van Neerven et al. (1993) *J. Immunol.* 151:2326–2335), animal dander (see, for example, Rogers et al. (1993) *Mol. Immunol.* 30:559–568), animal saliva, bee venom, and fungal spores. Live, attenuated and inactivated microorganisms such as HIV-1, HIV-2, herpes simplex virus, hepatitis A virus (Bradley et al. (1984) *J. Med. Virol.* 14:373–386), rotavirus, polio virus (Jiang et al. (1986) *J. Biol. Stand.* 14:103–109), hepatitis B virus, measles virus (James et al. (1995) *N. Engl. J. Med.* 332:1262–1266), human and bovine papilloma virus, and slow brain viruses can provide peptide antigens. For immunization against tumor formation, immunomodulatory peptides can include tumor cells (live or irradiated), tumor cell extracts, or protein subunits of tumor antigens. Vaccines for immuno-based contraception can be formed by including sperm proteins administered with ISS. Lea et al. (1996) *Biochim. Biophys. Acta* 1307:263.

The ISS and antigen can be administered as an ISS-antigen conjugate and/or they can be co-administered as a complex in the form of an admixture, such as in an emulsion. The association of the ISS and the antigen molecules in an ISS-antigen conjugate can be through covalent interactions and/or through non-covalent interactions, including high affinity and/or low affinity interactions. Examples of non-covalent interactions that can couple an ISS and an antigen in an ISS-antigen conjugate include, but are not limited to, ionic bonds, hydrophobic interactions, hydrogen bonds and van der Waals attractions.

In another embodiment, ISS can be administered in conjunction with one or more immunomodulatory facilitator. Thus, the invention provides compositions comprising ISS and an immunomodulatory facilitator. As used herein, the term "immunomodulatory facilitator" refers to molecules which support and/or enhance the immunomodulatory activity of an ISS. Examples of immunomodulatory facilitators can include co-stimulatory molecules, such as cytokines, and/or adjuvants. The ISS and facilitator can be administered as an ISS-facilitator conjugate and/or they can be co-administered as a complex in the form of an admixture, such as in an emulsion. The association of the ISS and the facilitator molecules in an ISS-facilitator conjugate can be through covalent interactions and/or through non-covalent interactions, including high affinity and/or low affinity interactions. Examples of non-covalent interactions that can couple an ISS and a facilitator in an ISS-facilitator conjugate include, but are not limited to, ionic bonds, hydrophobic interactions, hydrogen bonds and van der Waals attractions.

Immunomodulatory facilitators include, but are not limited to, co-stimulatory molecules (such as cytokines, chemokines, targeting protein ligand, trans-activating factors, peptides, and peptides comprising a modified amino acid) and adjuvants (such as alum, lipid emulsions, and polylactide/polyglycolide microparticles).

Among suitable immunomodulatory cytokine peptides for administration with ISS are the interleukins (e.g., IL-1, IL-2, IL-3, etc.), interferons (e.g., IFN-α, IFN-β, IFN-γ), erythropoietin, colony stimulating factors (e.g., G-CSF, M-CSF, GM-CSF) and TNF-α. Preferably, immunostimulatory peptides for use in conjunction with ISS oligonucleotides are those that stimulate Th1-type immune responses, such as IL-12 (Bliss et al. (1996) *J. Immunol.* 156:887–894), IL-18, TNF-α, β and γ, and/or transforming growth factor (TGF)-α.

Peptides administered with ISS can also include amino acid sequences that mediate protein binding to a specific receptor or that mediate targeting to a specific cell type or tissue. Examples include, but are not limited to, antibodies or antibody fragments, peptide hormones such as human growth hormone, and enzymes. Immunomodulatory peptides also include peptide hormones, peptide neurotransmitters and peptide growth factors. Co-stimulatory molecules such as B7 (CD80), trans-activating proteins such as transcription factors, chemokines such as macrophage chemotactic protein (MCP) and other chemoattractant or chemotactic peptides are also useful peptides for administration with ISS.

The invention also provides for the administration of ISS in conjunction with an adjuvant to effect modulation of an immune response. Administration of an antigen with an ISS and an adjuvant leads to a potentiation of a immune response to the antigen and thus, can result in an enhanced immune response compared to that which results from a composition comprising the ISS and antigen alone. For example, we have shown that administration of an antigen with an ISS and an adjuvant leads to an enhanced primary immune response. More surprisingly, and significantly, there is an enhanced Th1 immune response compared to administration of ISS and antigen alone (i.e., without adjuvant). This enhancement is often synergistic, i.e., a greater effect than what one would expect by adding the contributions of the individual components. As is understood in the art, some adjuvants stimulate a Th2 response when administered with antigen. Surprisingly, a Th1 response is enhanced (and the Th2 response is diminished) when ISS is administered with these adjuvants. Other types of adjuvants enhance a Th1 or a Th1/Th2 mixed response. ISS enhances a Th1 response when administered with these adjuvants (i.e., those adjuvants which enhance a Th1 or Th1/Th2 mixed response), and this enhancement is synergistic.

Thus, in another embodiment, the invention provides compositions comprising ISS, an antigen and an adjuvant whereby the ISS/antigen/adjuvant are co-administered. Preferably, the immunogenic composition contains an amount of an adjuvant sufficient to potentiate the immune response to the immunogen. Preferably, adjuvants include, but are not limited to, oil-in-water emulsions, water-in oil emulsions, alum (aluminum salts), liposomes and microparticles, including but not limited to, polystyrene, starch, polyphosphazene and polylactide/polyglycosides. More preferably, the ISS and antigen are co-administered with alum. More preferably, the ISS and antigen are co-administered with liposomes. Still more preferably, the ISS and antigen are co-administered with an oil-in-water emulsion. As the data in Example 3 indicates, adjuvants other than alum are most preferable. Accordingly, the invention provides compositions and methods using adjuvants other than alum (such as MF59).

The invention accordingly also provides methods of modulating an immune response, preferably a Th1 response (i.e., stimulation of Th1 lymphocytes) comprising administering an ISS, antigen, and adjuvant (preferably other than alum). Alternatively, these methods may be practiced by administering composition(s) comprising an ISS, antigen and adjuvant (preferably other than alum). The modulation of the immune response, particularly the enhancement or stimulation of the immune response, is greater than the modulation or enhancement observed upon administration of ISS and antigen alone (i.e., no adjuvant). Further, this modulation occurs regardless of the type of antigen administered.

It is understood that, with respect to these embodiments, the ISS may be any ISS, i.e., a polynucleotide which exhibits the requisite functional requirements of modulating, preferably enhancing, an immune response, including the humoral and/or cellular immune response. ISS are discussed below.

Suitable adjuvants also include, but are not limited to, squalene mixtures (SAF-1), muramyl peptide, saponin derivatives, mycobacterium cell wall preparations, monophosphoryl lipid A, mycolic acid derivatives, nonionic block copolymer surfactants, Quil A, cholera toxin B subunit, polyphosphazene and derivatives, and immunostimulating complexes (ISCOMs) such as those described by Takahashi et al. (1990) *Nature* 344:873–875, as well as, lipid-based adjuvants and others described herein. For veterinary use and for production of antibodies in animals, mitogenic components of Freund's adjuvant (both complete and incomplete) can be used.

As with all immunogenic compositions, the immunologically effective amounts of the components must be determined empirically. Factors to be considered include the antigenicity, whether or not ISS and/or antigen will be complexed with or covalently attached to an immunomodulatory facilitator, an adjuvant or carrier protein or other carrier, route of administration and the number of immunizing doses to be administered. Such factors are known in the vaccine art and it is well within the skill of immunologists to make such determinations without undue experimentation.

The invention further provides for compositions in which ISS and an immunomodulatory molecule(s) are in proximate association at a distance effective to enhance the immune response generated compared to the administration of the ISS and the immunomodulatory molecule as an admixture. It is understood that, with respect to these embodiments, the ISS may be any ISS, i.e., a polynucleotide which exhibits the requisite functional requirements of modulating, preferably enhancing, an immune response, including the humoral and/or cellular immune response. Besides the ISS described above, ISS have been described in the art and may be readily identified using standard assays which indicate various aspects of the immune response. See, e.g., WO 97/28259; WO 98/16247; WO 99/11275; Krieg et al. (1995) *Nature* 374:546–549; Yamamoto et al. (1992) *Microbiol. Immunol.* 36:983–987; Ballas et al. (1996) *J. Immunol.* 157: 1840; Klinman et al. (1997) *J. Immunol.* 158:3635; Sato et al. (1996) *Science* 273:352; Pisetsky (1996) *J. Immunol.* 156:421–423; Shimada et al. (1986) *Jpn. J. Cancer Res.* 77:808–816; and Cowdery et al. (1996) *J. Immunol.* 156:4570–4575.

Generally, an ISS comprises a sequence 5'-cytosine (C), guanine (G)-3'. An ISS may also comprise a hexameric sequence 5'-purine, purine, C, G, pyrimidine, pyrimidine-3'. For example, an ISS may comprise any of the following sequences: AACGTT, AGCGTC, GACGTT, GGCGTT, AACGTC, GACGTC, GGCGTC, AACGCC, AGCGCC, GACGCC, GGCGCC, AGCGCT, GACGCT, GGCGCT, GGCGTT, and AACGCC.

It is understood that an ISS may be single stranded or double stranded DNA, as well as single or double-stranded RNA and/or oligonucleosides. An ISS may or may not include one or more palindromic regions, which may be present in the hexameric motif described above or may extend beyond the motif. An ISS may comprise additional flanking sequences, some of which are described herein. An ISS may contain naturally-occurring or modified, non-naturally occurring bases, and may contain modified sugar, phosphate, and/or termini. For example, phosphate group (backbone) modifications may be made (e.g., methylphosphonate, phosphorothioate, phosphoroamidate and phosphorodithioate internucleotide linkages).

An ISS can be identified and/or its function confirmed by testing for aspects of an immune response using assays well known in the art, for example cytokine secretion, antibody production, and T cell proliferation (see Examples).

In some embodiments, the ISS which is in proximate association with an antigen comprises any of the following sequences: GACGCTCC; GACGCCC; AGCGTTCC; AGCGCTCC; AGCGTCCC; AGCGCCCC; AACGTCCC; AACGCCCC; GGCGTTCC; GGCGCTCC; GGCGTCCC; GGCGCCCC; GACGCTCG; GACGTCCG; GACGCCCG; AGCGTTCG; AGCGTCCG; AGCGCCCG; AACGTCCG; AACGCCCG; GGCGTTCG; GGCGCTCG; GGCGTCCG; GGCGCCCG. In other embodiments, the ISS which is in proximate association with antigen comprises any of SEQ ID NOS:1, 2, 5, 6, 7, 12, 15, and 16.

An ISS may be proximately associated with an antigen(s) by a number of ways. In some embodiments, an ISS and antigen are proximately associated by encapsulation. In other embodiments, an ISS and antigen are proximately associated by linkage to a platform molecule. A "platform molecule" (also termed "platform") is a molecule containing sites which allow for attachment of the ISS and antigen(s). In other embodiments, an ISS and antigen are proximately associated by adsorption onto a surface, preferably a carrier particle.

Thus, the invention provides compositions and methods of use thereof comprising an encapsulating agent that can maintain the proximate association of the ISS and immunomodulatory molecule until the complex is available to the target. Preferably, the composition comprising ISS, immunomodulatory molecule and encapsulating agent is in the form of adjuvant oil-in-water emulsions, microparticles and/or liposomes. More preferably, adjuvant oil-in-water emulsions, microparticles and/or liposomes encapsulating an ISS-immunomodulatory molecule are in the form of particles from about 0.04 $\mu$m to about 100 $\mu$m in size, more preferably, from about 0.1 $\mu$m to about 20 $\mu$m, even more preferably, from about 0.15 $\mu$m to about 10 $\mu$m.

Colloidal dispersion systems, such as microspheres, beads, macromolecular complexes, nanocapsules and lipid-based system, such as oil-in-water emulsions, micelles, mixed micelles and liposomes can provide effective encapsulation of ISS-containing compositions.

The encapsulation composition further comprises any of a wide variety of components. These include, but are not limited to, alum, lipids, phospholipids, lipid membrane structures (LMS), polyethylene glycol (PEG) and other polymers, such as polypeptides, glycopeptides, and polysaccharides.

Polypeptides suitable for encapsulation components include any known in the art and include, but are not limited to, fatty acid binding proteins. Modified polypeptides contain any of a variety of modifications, including, but not limited to glycosylation, phosphorylation, myristylation, sulfation and hydroxylation. As used herein, a suitable polypeptide is one that will protect an ISS-containing composition to preserve the immunomodulatory activity thereof. Examples of binding proteins include, but are not limited to, albumins such as bovine serum albumin (BSA) and pea albumin.

Other suitable polymers can be any known in the art of pharmaceuticals and include, but are not limited to, naturally-occurring polymers such as dextrans, hydroxyethyl starch, and polysaccharides, and synthetic polymers. Examples of naturally occurring polymers include proteins, glycopeptides, polysaccharides, dextran and lipids. The additional polymer can be a synthetic polymer. Examples of synthetic polymers which are suitable for use in the present invention include, but are not limited to, polyalkyl glycols (PAG) such as PEG, polyoxyethylated polyols (POP), such as polyoxyethylated glycerol (POG), polytrimethylene glycol (PTG) polypropylene glycol (PPG), polyhydroxyethyl methacrylate, polyvinyl alcohol (PVA), polyacrylic acid, polyethyloxazoline, polyacrylamide, polyvinylpyrrolidone (PVP), polyamino acids, polyurethane and polyphosphazene. The synthetic polymers can also be linear or branched, substituted or unsubstituted, homopolymeric, co-polymers, or block co-polymers of two or more different synthetic monomers.

PEGs constitute a diverse group of molecules. A general formula for PEGs is as follows:

$R_1O-(CH_2CH_2O)_n-R_3$ where $R_1$ and $R_3$ are independently H, $H_3C$, OH, or a linear or branched, substituted or unsubstituted alkyl group and n is an integer between 1 and about 1,000. The term "PEG" includes both unsubstituted ($R_1$ and $R_3$=H) as well as substituted PEG. The PEGs for use in encapsulation compositions of the present invention are either purchased from chemical suppliers or synthesized using techniques known to those of skill in the art.

The term "LMS", as used herein, means lamellar lipid particles wherein polar head groups of a polar lipid are arranged to face an aqueous phase of an interface to form membrane structures. Examples of the LMSs include liposomes, micelles, cochleates (i.e., generally cylindrical liposomes), microemulsions, unilamellar vesicles, multilamellar vesicles, and the like.

A preferred colloidal dispersion system of this invention is a liposome. In mice immunized with a liposome-encapsulated antigen, liposomes appeared to enhance a Th1-type immune response to the antigen. Aramaki et al. (1995) *Vaccine* 13:1809–1814. As used herein, a "liposome" or "lipid vesicle" is a small vesicle bounded by at least one and possibly more than one bilayer lipid membrane. Liposomes are made artificially from phospholipids, glycolipids, lipids, steroids such as cholesterol, related molecules, or a combination thereof by any technique known in the art, including but not limited to sonication, extrusion, or removal of detergent from lipid-detergent complexes. A liposome can also optionally comprise additional components, such as a tissue targeting component. It is understood that a "lipid membrane" or "lipid bilayer" need not consist exclusively of lipids, but can additionally contain any suitable other components, including, but not limited to, cholesterol and other steroids, lipid-soluble chemicals, proteins of any length, and other amphipathic molecules, providing the general structure of the membrane is a sheet of two hydrophilic surfaces sandwiching a hydrophobic core. For a general discussion of membrane structure, see *The Encyclopedia of Molecular Biology* by J. Kendrew (1994). For suitable lipids see e.g., Lasic (1993) "Liposomes: from Physics to Applications" Elsevier, Amsterdam.

Preferably, a liposomal composition is chosen that allows the membrane to be formed with reproducible qualities, such as diameter, and is stable in the presence of elements expected to occur where the liposome is to be used, such as physiological buffers and circulating molecules. Preferably, the liposome is resilient to the effects of manipulation by storage, freezing, and mixing with pharmaceutical excipients.

Lipids suitable for incorporation into lipid membrane structures include, but are not limited to, natural, semi-synthetic or synthetic mono- or di-glycerophospholipids including, but not limited to, phosphatidylcholines (PCs), phosphatidylethanolamines (PEs), phosphatidylglycerols (PGs), phosphatidylinositols (PIs), phosphatidic acids (PAs), phosphatidylserines (PSs), glycero- and cardiolipins. Sphingolipids such as sphingomyelin (SM) and cerebrosides can also be incorporated. While natural phospholipids occur with the phospho moiety at the sn-3 position and hydrophobic chains at the sn-1 and sn-2 positions, synthetic lipids can have alternative stereochemistry with, e.g., the phospho group at the sn-1 or sn-2 positions. Furthermore, the hydrophobic chains can be attached to the glycerol backbone by acyl, ether, alkyl or other linkages. Derivatives of these lipids are also suitable for incorporation into liposomes. Derivatives suitable for use include, but are not limited to, haloalkyl derivatives, including those in which all or some of the hydrogen atoms of the alkyl chains are substituted with, e.g., fluorine. In addition, cholesterol and other amphipathic steroids, bolaamphiphiles (lipids with polar moieties at either end of the molecule which form monolayer membranes) and polyglycerolmonoalkylthers can also be incorporated. Liposomes can be composed of a single lipid or mixtures of two or more different lipids.

In one embodiment, the lipid bilayer of the liposome is formed primarily from phospholipids. Preferably, the phospholipid composition is a complex mixture, comprising a combination of PS and additional lipids such as PC, PA, PE, PG and SM, PI, and/or cardiolipin (diphosphatidylglycerol). If desired, SM can be replaced with a greater proportion of PC, PE, or a combination thereof. PS can be optionally replaced with PG. The composition is chosen so as to confer upon the LMS both stability during storage and administration.

Practitioners of ordinary skill will readily appreciate that each phospholipid in the foregoing list can vary in its structure depending on the fatty acid moieties that are esterified to the glycerol moiety of the phospholipid. Generally, most commercially available forms of a particular phospholipid can be used. However, phospholipids containing particular fatty acid moieties may be preferred for certain applications.

A general process for preparing liposomes containing ISS-containing compositions is as follows. An aqueous dispersion of liposomes is prepared from membrane components, such as phospholipids (e.g. PS, PC, PG, SM and PE) and glycolipids according to any known methods. See, e.g., *Ann. Rev. Biophys. Bioeng.* 9:467 (1980). The liposomes can further contain sterols, dialkylphosphates, diacylphosphatidic acids, stearylamine, α-tocopherol, etc., in the liposomal membrane.

To the liposomal dispersion thus prepared is added an aqueous solution of the ISS-containing composition and the mixture is allowed to stand for a given period of time, preferably under warming at a temperature above the phase transition temperature of the membrane or above 40° C., followed by cooling to thereby prepare liposomes containing the ISS-containing composition in the liposomal membrane. Alternatively, the desired liposomes can also be prepared by previously mixing the above-described membrane components and ISS-containing composition and treating the mixture in accordance with known methods for preparing liposomes.

The lipid vesicles can be prepared by any suitable technique known in the art. Methods include, but are not limited to, microencapsulation, microfluidization, LLC method, ethanol injection, freon injection, the "bubble" method, detergent dialysis, hydration, sonication, and reverse-phase evaporation. Reviewed in Watwe et al. (1995) *Curr. Sci.* 68:715–724. For example, ultrasonication and dialysis methods generally produce small unilamellar vesicles; extrusion and reverse-phase evaporation generally produce larger sized vesicles. Techniques may be combined in order to provide vesicles with the most desirable attributes.

Optionally, the LMS also includes steroids to improve the rigidity of the membrane. Any amount of a steroid can be used. Suitable steroids include, but are not limited to, cholesterol and cholestanol. Other molecules that can be used to increase the rigidity of the membrane include, but are not limited to, cross-linked phospholipids.

Other preferred LMSs for use in vivo are those with an enhanced ability to evade the reticuloendothelial system, which normally phagocytoses and destroys non-native materials, thereby giving the liposomes a longer period in which to reach the target cell. Effective lipid compositions in this regard are those with a large proportion of SM and cholesterol, or SM and PI. LMSs with prolonged circulation time also include those that comprise the monosialoganglioside GM1, glucuronide, or PEG.

The invention encompasses LMSs containing tissue or cellular targeting components. Such targeting components are components of a LMS that enhance its accumulation at certain tissue or cellular sites in preference to other tissue or cellular sites when administered to an intact animal, organ, or cell culture. A targeting component is generally accessible from outside the liposome, and is therefore preferably either bound to the outer surface or inserted into the outer lipid bilayer. A targeting component can be inter alia a peptide, a region of a larger peptide, an antibody specific for a cell surface molecule or marker, or antigen binding fragment thereof, a nucleic acid, a carbohydrate, a region of a complex carbohydrate, a special lipid, or a small molecule such as a drug, hormone, or hapten, attached to any of the aforementioned molecules. Antibodies with specificity toward cell type-specific cell surface markers are known in the art and are readily prepared by methods known in the art.

The LMSs can be targeted to any cell type toward which a therapeutic treatment is to be directed, e.g., a cell type which can modulate and/or participate in an immune response. Such target cells and organs include, but are not limited to, APCs, such as macrophages, dendritic cells and lymphocytes, lymphatic structures, such as lymph nodes and the spleen, and nonlymphatic structures, particularly those in which dendritic cells are found.

The LMS compositions of the present invention can additionally comprise surfactants. Surfactants can be cationic, anionic, amphiphilic, or nonionic. A preferred class of surfactants are nonionic surfactants; particularly preferred are those that are water soluble. Nonionic, water soluble surfactants include polyoxyethylene derivatives of fatty alcohols, fatty acid ester of fatty alcohols and glyceryl esters, wherein the polyoxyethylene group is coupled via an ether linkage to an alcohol group. Examples include, but are not limited to, polyoxyethylene sorbitan fatty acid esters, polyoxyethylene castor oil derivatives, polyoxyethylene hardened castor oil derivatives, fatty acid sodium salts, sodium cholates, polyexyethylene fatty acid ester and polyoxyethylene alkyl ethers.

The LMS compositions encompassed herein include micelles. The term "micelles" as used herein means aggregates which form from tenside molecules in aqueous solutions above a specific temperature (Krafft point) or a characteristic concentration, the critical micellization concentration (cmc). When the cmc is exceeded, the monomer concentration remains practically constant and the excess tenside molecules form micelles. Micelles are thermodynamically stable association colloids of surfactant substances in which the hydrophobic radicals of the monomers lie in the interior of the aggregates and are held together by hydrophobic interaction; the hydrophilic groups face the water and by solvation provide the solubility of the colloid. Micelles occur in various shapes (spheres, rods, discs) depending on the chemical constitution of the tenside and on the temperature, concentration or ionic strength of the solution. Reaching the cmc is manifest by abrupt changes in surface tension, osmotic pressure, electrical conductivity and viscosity.

A process for preparing micelles containing ISS-containing compositions is as follows. A micelle-forming surfactant, such as polyoxyethylene sorbitan fatty acid esters, polyoxyethylene castor oil -derivatives, polyoxyethylene hardened castor oil derivatives, fatty acid sodium salts, sodium cholates, polyoxyethylene fatty acid ester, and polyoxyethylene alkyl ethers, alkyl glycosides, is added to water at a concentration above the cmc to prepare a micellar dispersion. To the micellar dispersion is added an aqueous solution of an ISS-containing composition and the mixture is allowed to stand for a given period of time, preferably under warming at 40° C. or higher, followed by cooling, to thereby prepare micelles containing ISS-containing compositions in the micellar membrane. Alternatively, the desired micelles can also be prepared by previously mixing the above-described micelle-forming substances and ISS-containing compositions and treating the mixture according to known methods for micelle formation.

In embodiments in which an ISS and antigen are proximately associated by linkage to a platform molecule, the platform may be proteinaceous or non-proteinaceous (i.e., organic). Examples of proteinaceous platforms include, but are not limited to, albumin, gammaglobulin, immunoglobulin (IgG) and ovalbumin. Borel et al. (1990) *Immunol. Methods* 126:159–168; Dumas et al. (1995) Arch. *Dematol. Res.* 287:123–128; Borel et al. (1995) *Int. Arch. Allergy Immunol.* 107:264–267; Borel et al. (1996) *Ann. N.Y. Acad. Sci.* 778:80–87. A platform is multi-valent (i.e., contains more than one binding, or linking, site) to accommodate binding to both an ISS and antigen, and may preferably contain multiple binding sites. Other examples of polymeric platforms are dextran, polyacrylamide, ficoll, carboxymethylcellulose, polyvinyl alcohol, and poly D-glutamic acid/D-lysine.

The principles of using platform molecules are well understood in the art. Generally, a platform contains, or is derivatized to contain, appropriate binding sites for ISS and antigen. In addition, or alternatively, ISS and/or antigen is derivatized to provide appropriate linkage groups. For example, a simple platform is a bi-functional linker (i.e., has two binding sites), such as a peptide. Further examples are discussed below.

Preferred platform molecules are biologically stabilized, i.e., they exhibit an in vivo excretion half-life often of hours to days to months to confer therapeutic efficacy, and are preferably composed of a synthetic single chain of defined composition. They generally have a molecular weight in the range of about 200 to about 200,000, preferably about 200 to about 50,000 (or less, such as 30,000). Examples of valency platform molecules are polymers (or are comprised of polymers) such as polyethylene glycol (PEG), poly-D-lysine, polyvinyl alcohol, polyvinylpyrrollidone, D-glutamic acid and D-lysine (in a ratio of 3:2). Preferred polymers are based on polyethylene glycols (PEGs) having a molecular weight of about 200 to about 8,000. Other molecules that may be used are albumin and IgG.

Other preferred platform molecules suitable for use within the present invention are the chemically-defined, non-polymeric valency platform molecules disclosed in U.S. Pat. No. 5,552,391. Particularly preferred homogeneous chemically-defined valency platform molecules suitable for use within the present invention are derivatized 2,2'-ethylenedioxydiethylamine (EDDA) and triethylene glycol (TEG).

Additional suitable valency platform molecules include, but are not limited to, tetraaminobenzene, heptaaminobetacyclodextrin, tetraaminopentaerythritol, 1,4,8,11-tetraazacyclotetradecane (Cyclam) and 1,4,7,10-tetraazacyclododecane (Cyclen).

In general, these platforms are made by standard chemical synthesis techniques. PEG must be derivatized and made multivalent, which is accomplished using standard techniques. Some substances suitable for conjugate synthesis, such as PEG, albumin, and IgG are available commercially.

Conjugation of an ISS and antigen to a platform molecule may be effected in any number of ways, typically involving one or more crosslinking agents and functional groups on the antigen and ISS platform and platform molecule. Platforms and ISS and antigen must have appropriate linking groups. Linking groups are added to platforms using standard synthetic chemistry techniques. Linking groups may be added to polypeptide antigens and ISS using either standard solid phase synthetic techniques or recombinant techniques. Recombinant approaches may require post-translational modification in order to attach a linker, and such methods are known in the art.

As an example, polypeptides contain amino acid side chain moieties containing functional groups such as amino, carboxyl or sulfhydryl groups that serve as sites for coupling the polypeptide to the platform. Residues that have such functional groups may be added to the polypeptide if the polypeptide does not already contain these groups. Such residues may be incorporated by solid phase synthesis techniques or recombinant techniques, both of which are well known in the peptide synthesis arts. When the polypeptide has a carbohydrate side chain(s) (or if the antigen is a carbohydrate), functional amino, sulfhydryl and/or aldehyde groups may be incorporated therein by conventional chemistry. For instance, primary amino groups may be incorporated by reaction with ethylenediamine in the presence of sodium cyanoborohydride, sulfhydryls may be introduced by reaction of cysteamine dihydrochloride followed by reduction with a standard disulfide reducing agent, while aldehyde groups may be generated following periodate oxidation. In a similar fashion, the platform molecule may also be derivatized to contain functional groups if it does not already possess appropriate functional groups.

Hydrophilic linkers of variable lengths are useful for connecting ISS and antigen to platform molecules. Suitable linkers include linear oligomers or polymers of ethylene glycol. Such linkers include linkers with the formula $R^1S(CH_2CH_2O)_nCH_2CH_2O(CH_2)_mCO_2R^2$ wherein n=0–200, m=1 or 2, $R^1$=H or a protecting group such as trityl, $R^2$=H or alkyl or aryl, e.g., 4-nitrophenyl ester. These linkers are useful in connecting a molecule containing a thiol reactive group such as haloaceyl, maleiamide, etc., via a thioether to a second molecule which contains an amino group via an amide bond. These linkers are flexible with regard to the order of attachment, i.e., the thioether can be formed first or last.

In embodiments in which an ISS and antigen are proximately associated by adsorption onto a surface, the surface may be in the form of a carrier particle (for example, a nanoparticle) made with either an inorganic or organic core. Examples of such nanoparticles include, but are not limited to, nanocrystalline particles, nanoparticles made by the polymerization of alkylcyanoacrylates and nanoparticles made by the polymerization of methylidene malonate. Additional surfaces to which an ISS and antigen may be adsorbed include, but are not limited to, activated carbon particles and protein-ceramic nanoplates.

Adsorption of polynucleotides and polypeptides to a surface for the purpose of delivery of the adsorbed molecules to cells is well known in the art. See, for example, Douglas et al., 1987, *Crit. Rev. Ther. Drug. Carrier Syst.* 3:233–261; Hagiwara et al., 1987, *In Vivo* 1:241–252; Bousquet et al., 1999, *Pharm. Res.* 16:141–147; and Kossovsky et al., U.S. Pat. No. 5,460,831. Preferably, the material comprising the adsorbent surface is biodegradable. Adsorption of an ISS and/or antigen to a surface may occur through non-covalent interactions, including ionic and/or hydrophobic interactions.

In general, characteristics of nanoparticles, such as surface charge, particle size and molecular weight, depend upon polymerization conditions, monomer concentration and the presence of stabilizers during the polymerization process (Douglas et al., 1987). The surface of carrier particles may be modified, for example, with a surface coating, to allow or enhance adsorption of the ISS and/or antigen. Carrier particles with adsorbed ISS and/or antigen may be further coated with other substances. The addition of such other substances may, for example, prolong the half-life of the particles once administered to the subject and/or may target the particles to a specific cell type or tissue, as described herein.

Preferred nanocrystalline surfaces to which an ISS and antigen may be adsorbed have been described (see, for example, U.S. Pat. No. 5,460,831). Nanocrystalline core particles (with diameters of 1 µm or less) are coated with a surface energy modifying layer that promotes adsorption of polypeptides, polynucleotides and/or other pharmaceutical agents. As described in U.S. Pat. No. 5,460,83 1, for example, a core particle is coated with a surface that promotes adsorption of an oligonucleotide and is subsequently coated with an antigen preparation, for example, in the form of a lipid-antigen mixture. Such nanoparticles are self-assembling complexes of nanometer sized particles, typically on the order of 0.1 µm, that carry an inner layer of ISS and an outer layer of antigen.

Another preferred adsorbent surface are nanoparticles made by the polymerization of alkylcyanoacrylates. Alkylcyanoacrylates can be polymerized in acidified aqueous media by a process of anionic polymerization. Depending on the polymerization conditions, the small particles tend to have sizes in the range of 20 to 3000 nm, and it is possible to make nanoparticles specific surface characteristics and with specific surface charges (Douglas et al., 1987). For example, oligonucleotides may be adsorbed to polyisobutyl- and polyisohexlcyanoacrylate nanoparticles in the presence of hydrophobic cations such as tetraphenylphosphonium chloride or quaternary ammonium salts, such as cetyltrimethyl ammonium bromide. Oligonucleotide adsorption on these nanoparticles appears to be mediated by the formation of ion pairs between negatively charged phosphate groups of the nucleic acid chain and the hydrophobic-cations. See, for example, Lambert et al., 1998, *Biochimie* 80:969–976, Chavany et al., 1994, *Pharm. Res.* 11: 1370–1378; Chavany et al., 1992, *Pharm. Res.* 9:441–449. Polypeptides may also be adsorbed to polyalkylcyanoacrylate nanoparticles. See, for example, Douglas et al., 1987; Schroeder et al., 1998, *Peptides* 19:777–780.

Another preferred adsorbent surface are nanoparticles made by the polymerization of methylidene malonate. For example, as described in Bousquet et al., 1999, polypeptides adsorbed to poly(methylidene malonate 2.1.2) nanoparticles appear to do so initially through electrostatic forces followed by stabilization through hydrophobic forces.

ISS Synthesis a) ISS

The ISS can be synthesized using techniques and nucleic acid synthesis equipment which are well known in the art including, but not limited to, enzymatic methods, chemical methods, and the degradation of larger oligonucleotide sequences. See, for example, Ausubel et al. (1987); and Sambrook et al. (1989). When assembled enzymatically, the individual units can be ligated, for example, with a ligase such as T4 DNA or RNA ligase. U.S. Pat. No. 5,124,246. Chemical synthesis of oligonucleotides can involve conventional automated methods, such as the phosphoramidite method disclosed by Warner et al. (1984) *DNA* 3:401. See also U.S. Pat. No. 4,458,066. Oligonucleotide degradation can be accomplished through the exposure of an oligonucleotide to a nuclease, as exemplified in U.S. Pat. No. 4,650,675.

The ISS can also be isolated using conventional polynucleotide isolation procedures. Such procedures include, but are not limited to, hybridization of probes to genomic or cDNA libraries to detect shared nucleotide sequences, antibody screening of expression libraries to detect shared structural features and synthesis of particular native sequences by the polymerase chain reaction.

Circular ISS can be isolated, synthesized through recombinant methods, or chemically synthesized. Where the circular ISS is obtained through isolation or through recombinant methods, the ISS will preferably be a plasmid. The chemical synthesis of smaller circular oligonucleotides can be performed using any method described in the literature. See, for instance, Gao et al. (1995) *Nucleic Acids Res.* 23:2025–2029; and Wang et al. (1994) *Nucleic Acids Res.* 22:2326–2333.

The ISS can also contain phosphorous based modified oligonucleotides. These can be synthesized using standard chemical transformations. The efficient solid-support based construction of methylphosphonates has also been described. The synthesis of other phosphorous based modified oligonucleotides, such as phosphotriesters (Miller et al. (1971) *JACS* 93:6657–6665), phosphoramidates (Jager et al. (1988) *Biochem.* 27:7247–7246), and phosphorodithioates (U.S. Pat. No. 5,453,496) has also been described. Other non-phosphorous based modified oligonucleotides can also be used. Stirchak et al. (1989) *Nucleic Acids Res.* 17:6129–6141.

The techniques for making phosphate group modifications to oligonucleotides are known in the art. For review of one such useful technique, an intermediate phosphate triester for the target oligonucleotide product is prepared and oxidized to the naturally occurring phosphate triester with aqueous iodine or with other agents, such as anhydrous amines. The resulting oligonucleotide phosphoramidates can be treated with sulfur to yield phosphorothioates. The same general technique (excepting the sulfur treatment step) can be applied to yield methylphosphoamidites from methylphosphonates. See also, U.S. Pat. Nos. 4,425,732; 4,458,066; 5,218,103; and 5,453,496.

The preparation of base-modified nucleosides, and the synthesis of modified oligonucleotides using said basemodified nucleosides as precursors, has been described, for example, in U.S. Pat. Nos. 4,910,300, 4,948,882, and 5,093,232. These base-modified nucleosides have been designed so that they can be incorporated by chemical synthesis into either terminal or internal positions of an oligonucleotide. Such base-modified nucleosides, present at either terminal or internal positions of an oligonucleotide, can serve as sites for attachment of a peptide or other antigen. Nucleosides modified in their sugar moiety have also been described (including, but not limited to, e.g., U.S. Pat. Nos. 4,849,513, 5,015,733, 5,118,800, 5,118,802) and can be used similarly.

b) Immunomodulatory Molecules

Attenuated and inactivated viruses are suitable for use herein as the antigen. Preparation of these viruses is well-known in the art. Polio virus can be inactivated by chemical agents such as beta-propiolactone. Jiang et al. (1986). The growth of attenuated strains of Hepatitis A virus has been described (Bradley et al. (1984)), as well as the growth of attenuated measles virus (James et al. (1995). Additionally, attenuated and inactivated viruses such as HIV-1, HIV-2, herpes simplex virus, hepatitis B virus, rotavirus, human and non-human papillomavirus and slow brain viruses can provide peptide antigens.

Allergens are suitable for use herein as immunomodulatory molecules. Preparation of many allergens is well-known in the art, including, but not limited to, preparation of ragweed pollen allergen Antigen E (Amb aI) (Rafnar et al. 1991), major dust mite allergens Der pI and Der PII (Chua et al. (1988); and Chua et al. (1990)), white birch pollen Betvl (Breitneder et al. 1989), domestic cat allergen Fel dI (Rogers et al. (1993), and protein antigens from tree pollen (Elsayed et al. (1991)). Preparation of protein antigens from grass pollen for in vivo administration has been reported. Malley (1989).

Immunomodulatory peptides can be native or synthesized chemically or enzymatically. Any method of chemical synthesis known in the art is suitable. Solution phase peptide synthesis can be used to construct peptides of moderate size or, for the chemical construction of peptides, solid phase synthesis can be employed. Atherton et al. (1981) *Hoppe Seylers Z. Physiol. Chem.* 362:833–839. Proteolytic enzymes can also be utilized to couple amino acids to produce peptides. Kullmann (1987) *Enzymatic Peptide Synthesis*, CRC Press, Inc. Alternatively, the peptide can be obtained by using the biochemical machinery of a cell, or by isolation from a biological source. Recombinant DNA techniques can be employed for the production of peptides. Hames et al. (1987) *Transcription and Translation: A Practical Approach*, IRL Press. Peptides can also be isolated using standard techniques such as affinity chromatography.

Preferably the antigens are peptides, lipids (e.g. sterols, fatty acids, and phospholipids), polysaccharides such as those used in *H. influenza* vaccines, gangliosides and glycoproteins. These can be obtained through several methods known in the art, including isolation and synthesis using chemical and enzymatic methods. In certain cases, such as for many sterols, fatty acids and phospholipids, the antigenic portions of the molecules are commercially available.

c) ISS-Immunomodulatory Molecule Conjugates

The ISS portion can be coupled with the immunomodulatory molecule portion of a conjugate in a variety of ways, including covalent and/or non-covalent interactions.

The link between the portions can be made at the 3' or 5' end of the ISS, or at a suitably modified base at an internal position in the ISS. If the immunomodulatory molecule is a peptide and contains a suitable reactive group (e.g., an N-hydroxysuccinimide ester) it can be reacted directly with the $N^4$ amino group of cytosine residues. Depending on the number and location of cytosine residues in the ISS, specific labeling at one or more residues can be achieved.

Alternatively, modified oligonucleosides, such as are known in the art, can be incorporated at either terminus, or at internal positions in the ISS. These can contain blocked functional groups which, when deblocked, are reactive with a variety of functional groups which can be present on, or attached to, the immunomodulatory molecule of interest.

Where the immunomodulatory molecule is a peptide, this portion of the conjugate can be attached to the 3'-end of the ISS through solid support chemistry. For example, the ISS portion can be added to a polypeptide portion that has been presynthesized on a support. Haralambidis et al. (1 990a) Nucleic Acids Res. 18:493–499; and Haralambidis et al. (1990b) Nucleic Acids Res. 18:501–505. Alternatively, the ISS can be synthesized such that it is connected to a solid support through a cleavable linker extending from the 3'-end. Upon chemical cleavage of the ISS from the support, a terminal thiol group is left at the 3'-end of the oligonucleotide (Zuckermann et al. (1987) Nucleic Acids Res. 15:5305–5321; and Corey et al. (1987) Science 238:1401–1403) or a terminal amine group is left at the 3'-end of the oligonucleotide (Nelson et al. (1989) Nucleic Acids Res. 17:1781–1794). Conjugation of the amino-modified ISS to amino groups of the peptide can be performed as described in Benoit et al. (1987) Neuromethods 6:43–72. Conjugation of the thiol-modified ISS to carboxyl groups of the peptide can be performed as described in Sinah et al. (1991) Oligonucleotide Analogues. A Practical Approach, IRL Press. Coupling of an oligonucleotide carrying an appended maleimide to the thiol side chain of a cysteine residue of a peptide has also been described. Tung et al. (1991) Bioconjug. Chem. 2:464–465.

The peptide portion of the conjugate can be attached to the 5'-end of the ISS through an amine, thiol, or carboxyl group that has been incorporated into the oligonucleotide during its synthesis. Preferably, while the oligonucleotide is fixed to the solid support, a linking group comprising a protected amine, thiol, or carboxyl at one end, and a phosphoramidite at the other, is covalently attached to the 5'-hydroxyl. Agrawal et al. (1986) Nucleic Acids Res. 14:6227–6245; Connolly (1985) Nucleic Acids Res. 13:4485–4502; Kremsky et al. (1987) Nucleic Acids Res. 15:2891–2909; Connolly (1987) Nucleic Acids Res. 15:3131–3139; Bischoff et al. (1987) Anal. Biochem. 164:336–344; Blanks et al. (1988) Nucleic Acids Res. 16:10283–10299; and U.S. Pat. Nos. 4,849,513, 5,015,733, 5,118,800, and 5,118,802. Subsequent to deprotection, the latent amine, thiol, and carboxyl functionalities can be used to covalently attach the oligonucleotide to a peptide. Benoit et al. (1987); and Sinah et al. (1991).

The peptide portion can be attached to a modified cytosine or uracil at any position in the ISS. The incorporation of a "linker arm" possessing a latent reactive functionality, such as an amine or carboxyl group, at C-5 of the modified base provides a handle for the peptide linkage. Ruth, 4th Annual Congress for Recombinant DNA Research, p. 123.

An ISS-immunomodulatory molecule conjugate can also be formed through non-covalent interactions, such as ionic bonds, hydrophobic interactions, hydrogen bonds and/or van der Waals attractions.

Non-covalently linked conjugates can include a non-covalent interaction such as a biotin-streptavidin complex. A biotinyl group can be attached, for example, to a modified base of an ISS. Roget et al. (1989) Nucleic Acids Res. 17:7643–7651. Incorporation of a streptavidin moiety into the peptide portion allows formation of a non-covalently bound complex of the streptavidin conjugated peptide and the biotinylated oligonucleotide.

Non-covalent associations can also occur through ionic interactions involving an ISS and residues within the immunomodulatory molecule, such as charged amino acids, or through the use of a linker portion comprising charged residues that can interact with both the oligonucleotide and the immunomodulatory molecule. For example, non-covalent conjugation can occur between a generally negatively-charged ISS and positively-charged amino acid residues of a peptide, e.g., polylysine and polyarginine residues.

Non-covalent conjugation between ISS and immunomodulatory molecules can occur through DNA binding motifs of molecules that interact with DNA as their natural ligands. For example, such DNA binding motifs can be found in transcription factors and anti-DNA antibodies.

The linkage of the ISS to a lipid can be formed using standard methods. These methods include, but are not limited to, the synthesis of oligonucleotide-phospholipid conjugates (Yanagawa et al. (1988) Nucleic Acids Symp. Ser. 19:189–192), oligonucleotide-fatty acid conjugates (Grabarek et al. (1990) Anal. Biochem. 185:131–135; and Staros et al. (1986) Anal. Biochem. 156:220–222), and oligonucleotide-sterol conjugates. Boujrad et al. (1993) Proc. Natl. Acad. Sci. USA 90:5728–5731.

The linkage of the oligonucleotide to an oligosaccharide can be formed using standard known methods. These methods include, but are not limited to, the synthesis of oligonucleotide-oligosaccharide conjugates, wherein the oligosaccharide is a moiety of an immunoglobulin. O'Shannessy et al. (1985) J. Applied Biochem. 7:347–355.

The linkage of a circular ISS to a peptide or antigen can be formed in several ways. Where the circular ISS is synthesized using recombinant or chemical methods, a modified nucleoside is suitable. Ruth (1991) in Oligonucleotides and Analogues: A Practical Approach, IRL Press. Standard linking technology can then be used to connect the circular ISS to the antigen or other peptide. Goodchild (1990) Bioconjug Chem. 1:165. Where the circular ISS is isolated, or synthesized using recombinant or chemical methods, the linkage can be formed by chemically activating, or photoactivating, a reactive group (e.g. carbene, radical) that has been incorporated into the antigen or other peptide.

Additional methods for the attachment of peptides and other molecules to oligonucleotides can be found in U.S. Pat. No. 5,391,723; Kessler (1992) "Nonradioactive labeling methods for nucleic acids" in Kricka (ed.) Nonisotopic DNA Probe Techniques, Academic Press; and Geoghegan et al. (1992) Bioconjug. Chem. 3:138–146.

Assessment of Immune Response to ISS

Analysis (both qualitative and quantitative) of the immune response to ISS-containing compositions can be by any method known in the art, including, but not limited to, measuring antigen-specific antibody production, activation of specific populations of lymphocytes such as CD4+ T cells or NK cells, and/or production of cytokines such as IFN, IL-2, IL-4, or IL-12. Methods for measuring specific antibody responses include enzyme-linked immunosorbent assay (ELISA) and are well known in the art. Measurement of numbers of specific types of lymphocytes such as CD4+ T cells can be achieved, for example, with fluorescence-activated cell sorting (FACS). Cytotoxicity assays can be performed for instance as described in Raz et al. (1994) *Proc. Natl. Acad Sci. USA* 91:9519–9523. Serum concentrations of cytokines can be measured, for example, by ELISA. These and other assays to evaluate the immune response to an immunogen are well known in the art. See, for example, *Selected Methods in Cellular Immunology* (1980) Mishell and Shiigi, eds., W.H. Freeman and Co.
Administration of the ISS The ISS can be administered alone or in combination with other pharmaceutical and/or immunogenic and/or immunostimulatory agents and can be combined with a physiologically acceptable carrier thereof. The effective amount and method of administration of the particular ISS formulation can vary based on the individual patient and the stage of the disease and other factors evident to one skilled in the art. The route(s) of administration useful in a particular application are apparent to one of skill in the art. Routes of administration include but are not limited to topical, dermal, transdermal, transmucosal, epidermal parenteral, gastrointestinal, and naso-pharyngeal and pulmonary, including transbronchial and transalveolar. A suitable dosage range is one that provides sufficient ISS-containing composition to attain a tissue concentration of about 1–10 $\mu$M as measured by blood levels. The absolute amount given to each patient depends on pharmacological properties such as bioavailability, clearance rate and route of administration.

As described herein, APCs and tissues with high concentration of APCs are preferred targets for the ISS-containing compositions. Thus, administration of ISS to mammalian skin and/or mucosa, where APCs are present in relatively high concentration, is preferred.

The present invention provides ISS-containing compositions suitable for topical application including, but not limited to, physiologically acceptable implants, ointments, creams, rinses and gels. Topical administration is, for instance, by a dressing or bandage having dispersed therein a delivery system, or by direct administration of a delivery system into incisions or open wounds. Creams, rinses, gels or ointments having dispersed therein an ISS-containing composition are suitable for use as topical ointments or wound filling agents.

Preferred routes of dermal administration are those which are least invasive. Preferred among these means are transdermal transmission, epidermal administration and subcutaneous injection. Of these means, epidermal administration is preferred for the greater concentrations of APCs expected to be in intradermal tissue.

Transdermal administration is accomplished by application of a cream, rinse, gel, etc. capable of allowing the ISS-containing composition to penetrate the skin and enter the blood stream. Compositions suitable for transdermal administration include, but are not limited to, pharmaceutically acceptable suspensions, oils, creams and ointments applied directly to the skin or incorporated into a protective carrier such as a transdermal device (so-called "patch"). Examples of suitable creams, ointments etc. can be found, for instance, in the Physician's Desk Reference.

For transdermal transmission, iontophoresis is a suitable method. Iontophoretic transmission can be accomplished using commercially available patches which deliver their product continuously through unbroken skin for periods of several days or more. Use of this method allows for controlled transmission of pharmaceutical compositions in relatively great concentrations, permits infusion of combination drugs and allows for contemporaneous use of an absorption promoter.

An exemplary patch product for use in this method is the LECTRO PATCH trademarked product of General Medical Company of Los Angeles, Calif. This product electronically maintains reservoir electrodes at neutral pH and can be adapted to provide dosages of differing concentrations, to dose continuously and/or periodically. Preparation and use of the patch should be performed according to the manufacturer's printed instructions which accompany the LECTRO PATCH product; those instructions are incorporated herein by this reference.

For transdermal transmission, low-frequency ultrasonic delivery is also a suitable method. Mitragotri et al. (1995) *Science* 269:850–853. Application of low-frequency ultrasonic frequencies (about 1 MHz) allows the general controlled delivery of therapeutic compositions, including those of high molecular weight.

Epidermal administration essentially involves mechanically or chemically irritating the outermost layer of the epidermis sufficiently to provoke an immune response to the irritant. Specifically, the irritation should be sufficient to attract APCs to the site of irritation.

An exemplary mechanical irritant means employs a multiplicity of very narrow diameter, short tines which can be used to irritate the skin and attract APCs to the site of irritation, to take up ISS-containing compositions transferred from the end of the tines. For example, the MONO-VACC old tuberculin test manufactured by Pasteur Merieux of Lyon, France contains a device suitable for introduction of ISS-containing compositions.

The device (which is distributed in the U.S. by Connaught Laboratories, Inc. of Swiftwater, Pa.) consists of a plastic container having a syringe plunger at one end and a tine disk at the other. The tine disk supports a multiplicity of narrow diameter tines of a length which will just scratch the outermost layer of epidermal cells. Each of the tines in the MONO-VACC kit is coated with old tuberculin; in the present invention, each needle is coated with a pharmaceutical composition of ISS-containing composition. Use of the device is preferably according to the manufacturer's written instructions included with the device product. Similar devices which can also be used in this embodiment are those which are currently used to perform allergy tests.

Another suitable approach to epidermal administration of ISS is by use of a chemical which irritates the outermost cells of the epidermis, thus provoking a sufficient immune response to attract APCs to the area. An example is a keratinolytic agent, such as the salicylic acid used in the commercially available topical depilatory creme sold by Noxema Corporation under the trademark NAIR. This approach can also be used to achieve epithelial administration in the mucosa. The chemical irritant can also be applied in conjunction with the mechanical irritant (as, for example, would occur if the MONO-VACC type tine were also coated with the chemical irritant). The ISS can be suspended in a carrier which also contains the chemical irritant or coadministered therewith.

Another delivery method for administering ISS-containing compositions makes use of non-lipid polymers, such as a synthetic polycationic amino polymer. Leff(1997) *Bioworld* 86:1–2.

Parenteral routes of administration include but are not limited to electrical (iontophoresis) or direct injection such as direct injection into a central venous line, intravenous, intramuscular, intraperitoneal, intradermal, or subcutaneous injection. Compositions suitable for parenteral administration include, but are not limited to pharmaceutically acceptable sterile isotonic solutions. Such solutions include, but are not limited to, saline and phosphate buffered saline for injection of the ISS-containing compositions.

Gastrointestinal routes of administration include, but are not limited to, ingestion and rectal. The invention includes ISS-containing compositions suitable for gastrointestinal administration including, but not limited to, pharmaceutically acceptable, powders, pills or liquids for ingestion and suppositories for rectal administration.

Naso-pharyngeal and pulmonary routes of administration include, but are not limited to, by-inhalation, transbronchial and transalveolar routes. The invention includes ISS-containing compositions suitable for by-inhalation administration including, but not limited to, various types of aerosols for inhalation, as well as powder forms for delivery systems. Devices suitable for by-inhalation administration of ISS-containing compositions include, but are not limited to, atomizers and vaporizers. Atomizers and vaporizers filled with the powders are among a variety of devices suitable for use in by-inhalation delivery of powders. See, e.g., Lindberg (1993) Summary of Lecture at Management Forum Dec. 6–7, 1993 "Creating the Future for Portable Inhalers."

The methods of producing suitable devices for injection, topical application, atomizers and vaporizers are known in the art and will not be described in detail.

The choice of delivery routes can be used to modulate the immune response elicited. For example, IgG titers and CTL activities were identical when an influenza virus vector was administered via intramuscular or epidermal (gene gun) routes; however, the muscular inoculation yielded primarily IgG2A, while the epidermal route yielded mostly IgG1. Pertmer et al. (1996) *J. Virol.* 70:6119–6125. Thus, one of skill in the art can take advantage of slight differences in immunogenicity elicited by different routes of administering the immunomodulatory oligonucleotides of the present invention.

The above-mentioned compositions and methods of administration are meant to describe but not limit the methods of administering the ISS-containing compositions of the invention. The methods of producing the various compositions and devices are within the ability of one skilled in the art and are not described in detail here.

Screening for ISS

The present invention also provides a method to screen for the immunomodulatory activity of ISS. In particular, the method provided allows in vitro screening of ISS for the ability to stimulate a Th1-type immune response in vivo. As described in Example 6, the screening method can involve the use of either a murine cell line, e.g., P388D.1, or a human cell line, e.g., 90196.B. Treatment of these cell lines with oligonucleotides with potential ISS activity and subsequent determination of cytokine production from the treated cells provided a reliable indication as to immunostimulatory activity of the oligonucleotide when administered in vivo. The use of cell lines, such as P388D.1 and/or 90109.B, allows for a readily available, consistent cell population on which the effect of the oligonucleotide composition can be measured. In general, oligonucleotides administered at concentrations ranging from 0.1 to 10 µg/ml that stimulated a production of cytokine, for example, IL-6 and/or IL-12, to a concentration >2 ng/ml in the culture supernatant after 48 to 72 hours indicate immunomodulatory activity. Details of in vitro techniques useful in making such an evaluation are given in the Examples; those of ordinary skill in the art will also know of, or can readily ascertain, other methods for measuring cytokine secretion and antibody production along the parameters taught herein.

The following examples are provided to illustrate, but not limit, the invention.

EXAMPLES

Example 1

Stimulation of Cytokine Production by Oligonucleotides Comprising an ISS Octanucleotide As described above, ISS activity in polynucleotides was initially associated with DNA containing unmethylated CpG dinucleotides. The ISS element was further defined as a hexameric sequence, preferably the sequence 5'-Purine, Purine, C, G, Pyrimidine, Pyrimidine-3' (Krieg et al. (1995)). Unfortunately, relying on the hexamer sequence to predict immunostimulatory activity yields, for the most part, inactive oligonucleotides. Additional experimentation provided herein indicates, however, that nucleotides surrounding the ISS hexamer can contribute significantly to the immunostimulatory activity associated with the ISS element. In particular, specific ISS sequences have been identified that stimulate a Th1-type immune response. Experiments that have identified such ISS elements are described below.

Over 150 different oligonucleotides (see Table 1 for examples) were tested for immunostimulatory activity on mouse splenocytes and/or on human peripheral blood mononuclear cells (hPBMCs). Immunostimulation in response to oligonucleotide was assessed by measurement of cytokine secretion into the culture media and by cell proliferation. Cytokine levels in the culture supernatant were determined by enzyme-linked immunosorbent assay (ELISA) tests.

The oligonucleotides were synthesized using standard solid phase oligonucleotide techniques. The solid phase ready analog monomers were purchased from Glen Research, Sterling, Va. and included in the standard manner in a solid phase oligonucleotide synthesizer. The synthesis of the oligonucleotides were performed by TriLink BioTechnologies Inc., San Diego, Calif.

Cells were isolated and prepared using standard techniques. hPBMCs were isolated from heparinized peripheral blood from healthy donors by ficoll Hypaque gradients. Spleens of BALB/c mice were harvested and the splenocytes isolated using standard teasing and treatment with ACK lysing buffer from BioWhittaker, Inc. Isolated cells were washed in RPMI 1640 media supplemented with 2% heat-inactivated fetal calf serum (FCS), 50 µM 2-mercaptoethanol, 1% penicillin-streptomycin, and 2 mM L-glutamine and resuspended at approximately $4 \times 10^6$ cells/ml in 10% FCS/RPMI (RPMI 1640 media with 10% heat-inactivated FCS, 50 µM 2-mercaptoethanol, 1% penicillin-streptomycin, and 2 mM L-glutamine).

Generally, cell cultures were set up in triplicate with approximately $4 \times 10^5$ cells/well in a 96-well, flat microtiter plate in 100 µl 10% F.CS/RPMI with the cells allowed to rest for at lest 1 hour after plating. For oligonucleotide activity assays, oligonucleotides were diluted in 10% FCS/RPMI and 100 µl of the desired oligonucleotide dilution was added to the appropriate well. In general, final oligonucleotide concentrations included 0.1 μg/ml, 1.0 μg/ml, and 10 μg/ml. Cells were then incubated for 1, 2, or 3 days.

To determine cell proliferation, 100 μl of supernatant was harvested from each well on appropriate days, pulsed with 1.0 μM tritiated thymidine and incubated overnight. Standard methods to assess tritiated thymidine incorporation were used to determine cell proliferation. Cytokine production by the cells was determined by ELISAs of culture supernatant using commercially-available antibodies to the cytokines.

Figure 2:
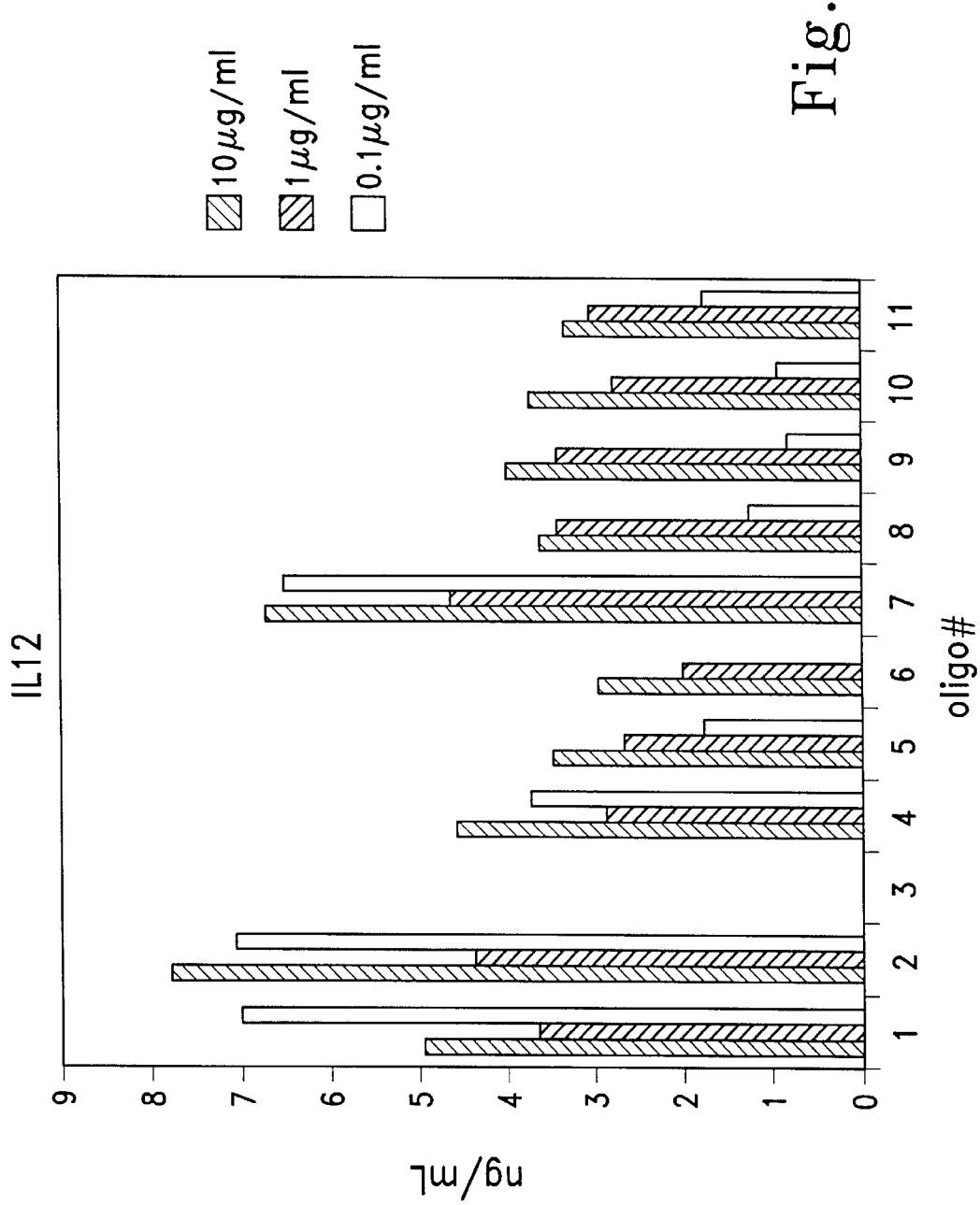
FIG. 2 is a graph depicting the level of IL-12 found in the culture supernatant of splenocytes after exposure to oligonucleotides for 48 hours. See Table 1 for identification of oligonucleotides.
Figure 3:
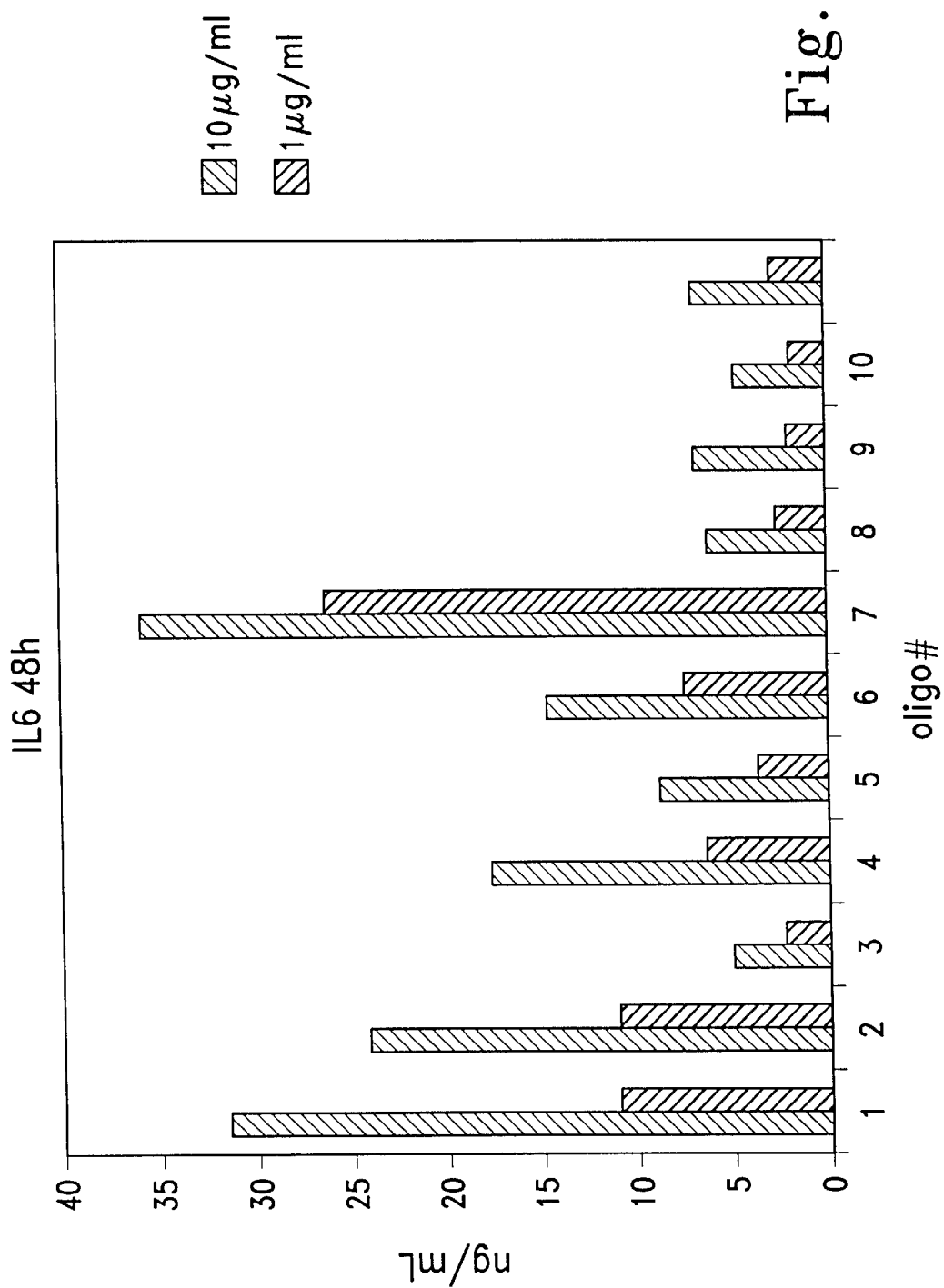
FIG. 3 is a graph depicting the level of IL-6 found in the culture supernatant of splenocytes after exposure to oligonucleotides for 48 hours. See Table 1 for identification of oligonucleotides.

Results of such experiments are graphically depicted in FIGS. 1–3. The oligonucleotides used included the following:

TABLE 1

| SEQ ID NO: | Oligonucleotide Sequence | |
| --- | --- | --- |
| 1 | tgaccgtgaacgttcgagatga | ISS (bold, underline) |
| 2 | tgactgtgaacgttcgagatga | ISS |
| 3 | tgactgtgaaggttagagatga | |
| 4 | tcatctcgaacgttccacagtca | ISS |
| 5 | tcatctcgaacgttcacggtca | |
| 6 | tgactgtgaacgttccagatga | ISS |
| 7 | tccataacgttcgcctaacgttcgtc | 2 × ISS |
| 8 | tgactgtgaacgttagcgatga | |
| 9 | tgactgtgaacgttagacgtga | |
| 10 | tgacgtgaacgttagagatga | |
| 11 | tgactcgtgaacgttagagatga | |

All oligonucleotides used in these experiments contained a phosphorothioate backbone.

As shown in FIGS. 1–3, the phosphorothioate oligonucleotides 1, 2 and 7 (SEQ ID NO:1, SEQ ID NO:2 and SEQ ID NO:7, respectively) are potent stimulators of secretion of IL-12, IFN-γ and IL-6 from murine splenocytes. These oligonucleotides also stimulate cytokine secretion from hPBMCs. All three of these oligonucleotides comprise the preferred octanucleotide sequence of 5'-Purine, Purine, Cytosine, Guanosine, Pyrimidine, Pyrimidine, Cytosine, Guanosine-3' (see Table 1).

Examples of additional oligonucleotides with immunostimulatory activity include oligonucleotides 4 and 6 (SEQ ID NO: 4 and SEQ ID NO:6). These immunostimulatory oligonucleotides also comprise a preferred octanucleotide sequence (see Table 1). FIGS. 1–3 and Table 1 also indicate that the inclusion of a hexameric ISS element, defined by Krieg et al. (1995) as 5'-Purine, Purine, C, G, Pyrimidine, Pyrimidine-3', in an oligonucleotide was not a reliable predictor of immunostimulatory activity for the oligonucleotide. See, for example, oligonucleotides 5, and 8–11.

Example 2

Stimulation of Cytokine Production by ISS Comprising Modified Bases

Several oligonucleotides comprising modified bases were tested for their immunostimulatory activity on mouse splenocytes and on hPBMCs. Immmunostimulation in response to oligonucleotide was assessed by measurement of cytokine secretion into the culture media and by cell proliferation as described above. Cell cultures and oligonucleotide activity assays were set up and performed as described above.

TABLE 2

| SEQ ID NO: | Oligonucleotide Sequence | |
| --- | --- | --- |
| 2 | tgactgtaacgttcgagatga | ISS (bold, underline) |
| 12 | tgactgtaabgttccagatga | b = 5-bromocytosine |
| 13 | tgactgtgaagcttagagatga | no ISS |
| 14 | tcactctcttccttactcttct | no ISS |
| 15 | tgactgtaabgttcgagatga | b = 5-bromocytosine |
| 16 | tgactgtaabgttbgagatga | b = 5-bromocytosine |
| 17 | tccatgabgttcgtgatcgt | b = 5-bromocytosine |
| 18 | tccataabgttcctgatgct | b = 5-bromocytosine |
| 19 | tccataabgttcgtgatgct | b = 5-bromocytosine |
| 20 | tccataabgttcgcctaacgttcg | b = 5-bromocytosine |
| 21 | tccataabgttcgcctaabgttcg | b = 5-bromocytosine |

Figure 4:
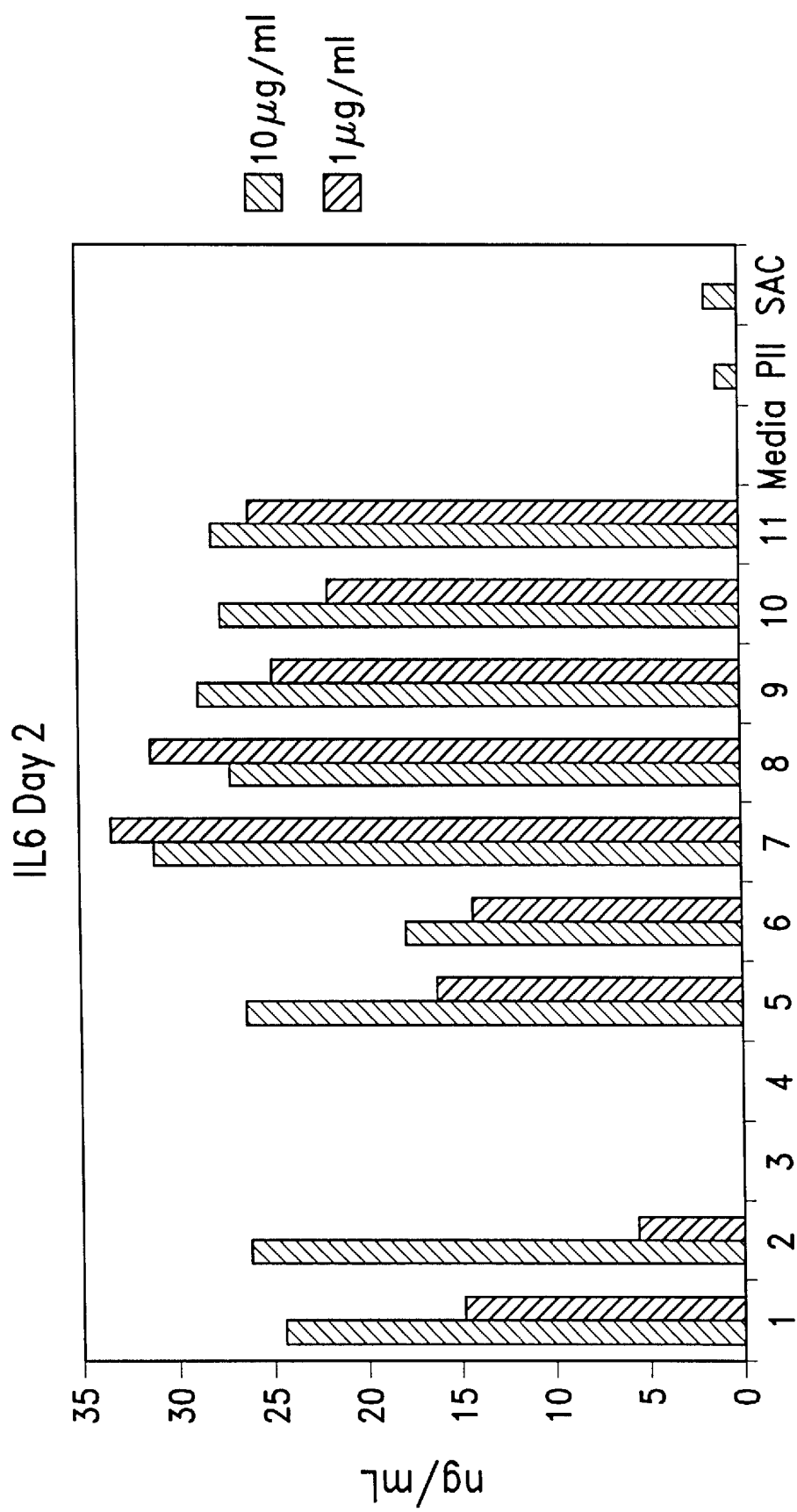
FIG. 4 presents a graph depicting the level of IL-6 found in the culture supernatant of splenocytes after exposure to oligonucleotides for 48 hours. See Table 2 for identification of oligonucleotides.
Figure 5:
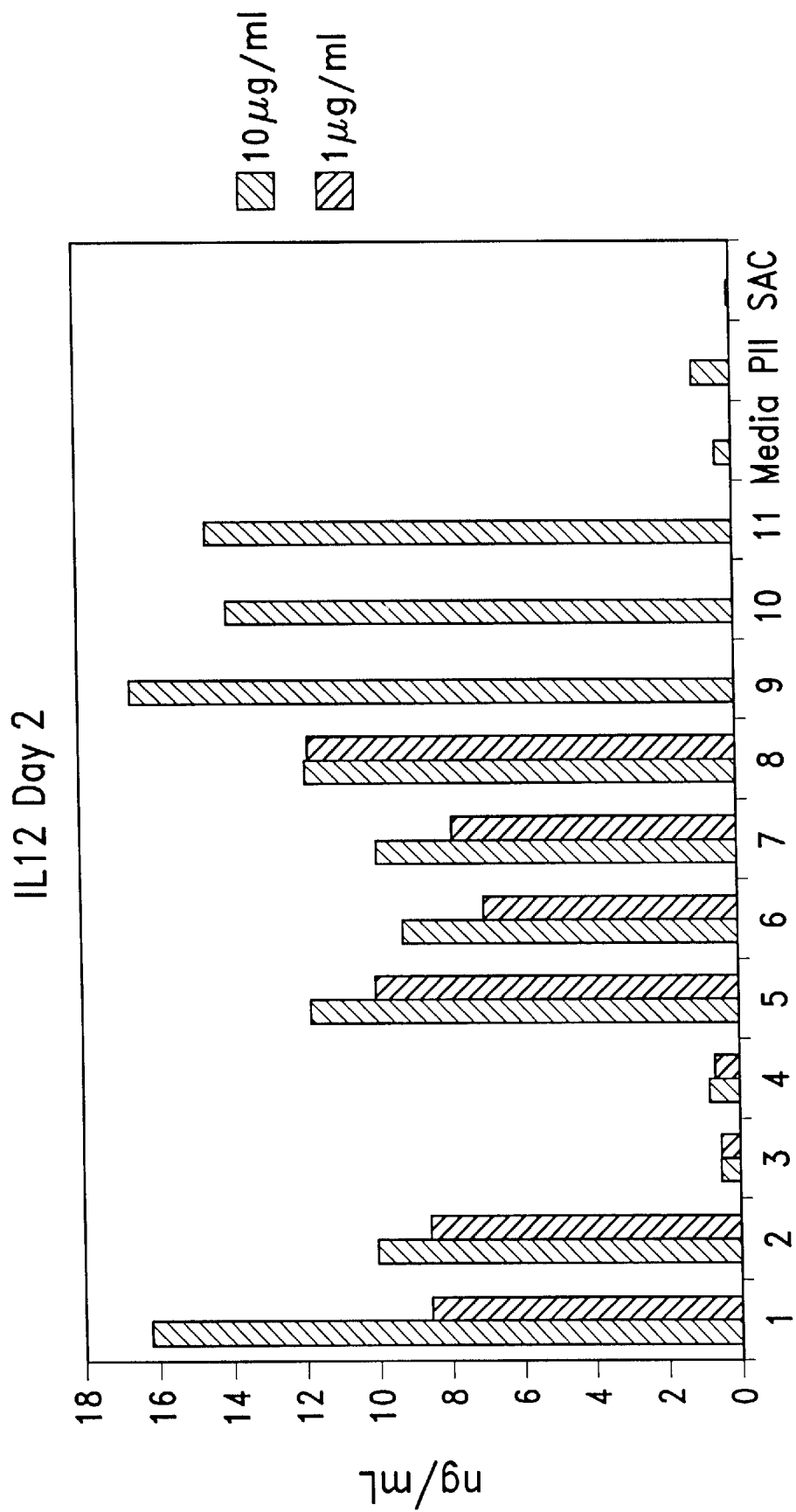
FIG. 5 presents a graph depicting the level of IL-12 found in the culture supernatant of splenocytes after exposure to oligonucleotides for 48 hours. See Table 2 for identification of oligonucleotides.
Figure 6:
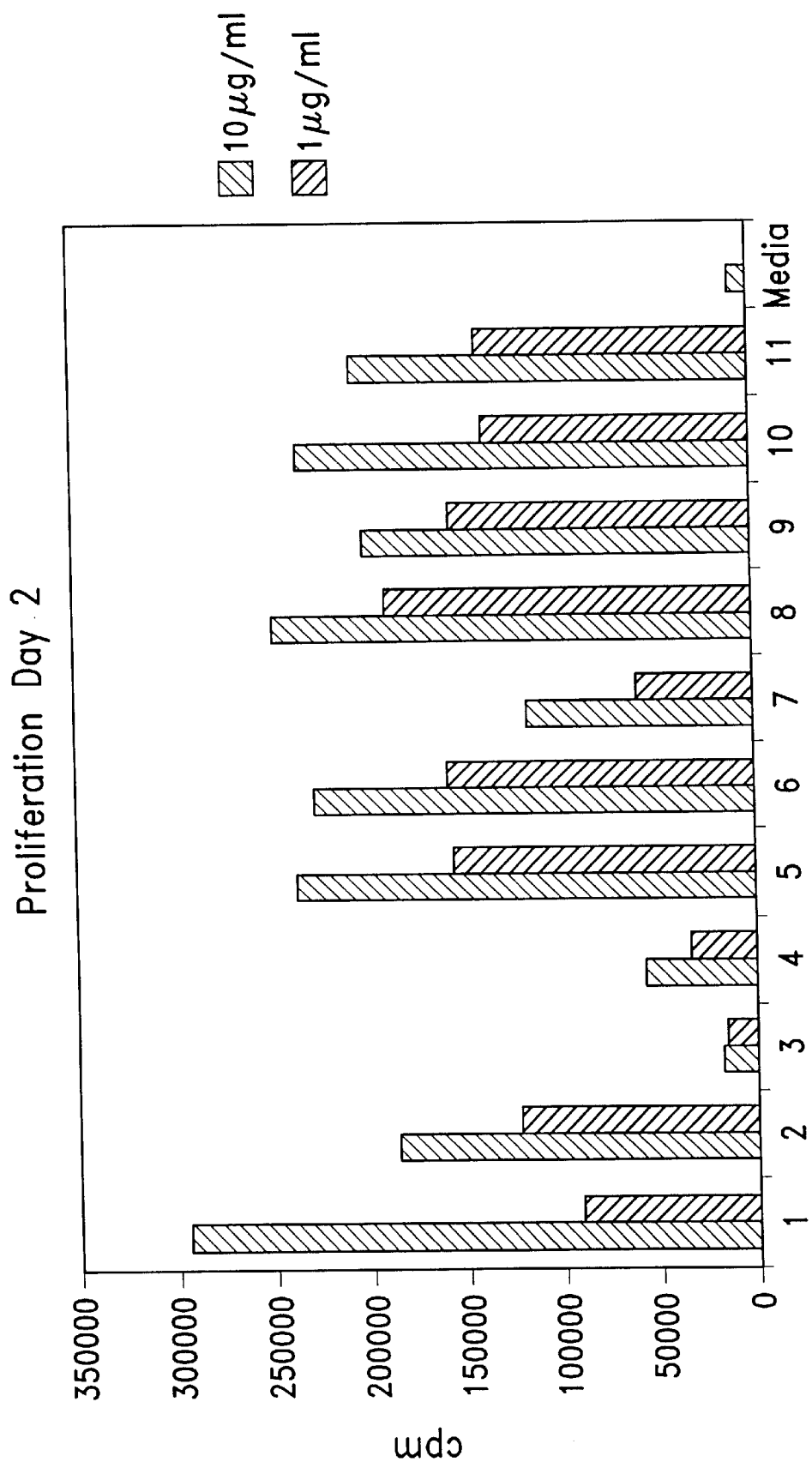
FIG. 6 presents a graph showing the efficacy of various oligonucleotides comprising modified cytosines to stimulate proliferation of splenocytes. Cell proliferation determined after 48 hours in culture. See Table 2 for identification of oligonucleotides.

FIGS. 4–6 depict cytokine production and cell proliferation results from an experiment in which mouse splenocytes were cultured oligonucleotides listed in Table 2, where b is 5-bromocytosine and an ISS octamer sequence is in bold and underlined. Oligonucleotides were used at a final concentration of 1.0 μg/ml or 10 μg/ml. Treatment of the cells with oligonucleotides containing at least one ISS resulted in the production of IL-6 and IL-12 from the cells, as well as a stimulation of cell proliferation. The oligonucleotides containing a modified ISS were, in general, as effective as or more effective than the oligonucleotide with an unmodified ISS. Oligonucleotides without an ISS were unable to stimulate IL-6 or IL-12 production or cell proliferation. All oligonucleotides used in this experiment contained a phosphorothioate backbone.

Example 3

Potentiation of an Immune Response with Adjuvant Co-administration

The effect of adjuvant co-administration with antigen and ISS on an immune response to the antigen was examined using the adjuvant aluminum hydroxide (alum) and the oil-in-water emulsion adjuvant, MF59. Compositions comprising 1 μg AgE, also known as Amb aI, a major allergic component of short ragweed, was injected intradermally into mice at week 0, 2, and 4. Antigen compositions used are listed in Table 3. Oligonucleotide 2 (SEQ ID NO:2) was used in the compositions as indicated.

TABLE 3

| | |
| --- | --- |
| AgE | AgE-oligo 2 conjugate |
| AgE + oligo 2 mix (equivalent) | AgE + oligo 2 mix (50 μg oligo 2) |
| AgE and MF59 | AgE-oligo 2 conjugate and MF59 |
| AgE and alum (25 μg) | AgE-oligo 2 conjugate and alum (25 μg) |
| AgE and alum (800 μg) | |

The amount of anti-AgE antibody in the serum of the mice was determined at day 0 and weeks 2, 4, and 6. Anti-AgE IgG1 and anti-AgE IgG2a antibody assays were performed by ELISA tests using the original AgE vaccine as the coated antigen on microtiter plates as described in Raz et al. (1996). Anti-AgE IgE was determined by standard radioimmunoassay techniques. Results of these experiments are depicted in FIGS. 7–9.

Figure 7:
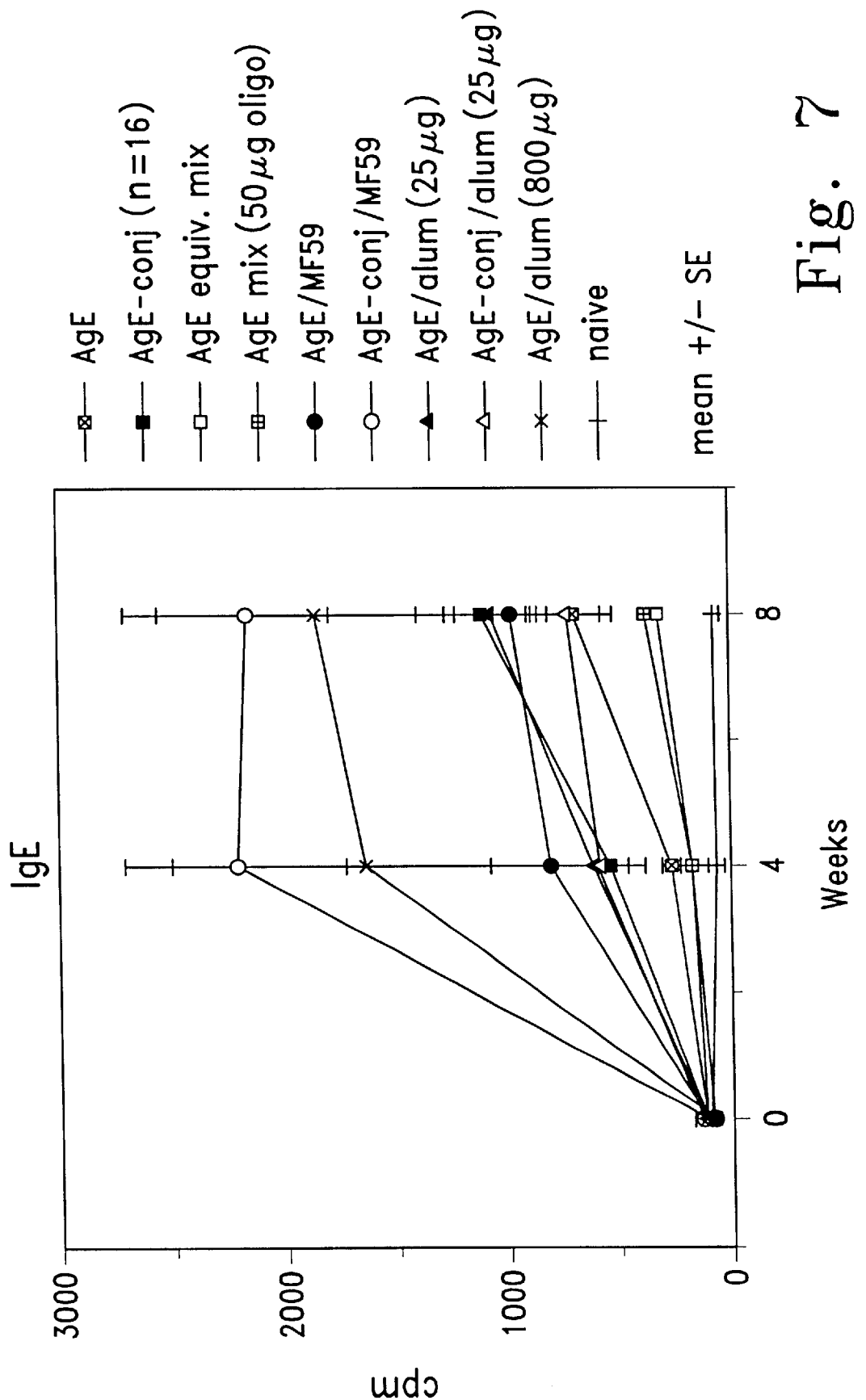
FIG. 7 is a graph depicting serum levels of anti-Amb aI IgE generated in treated animals.
Figure 8:
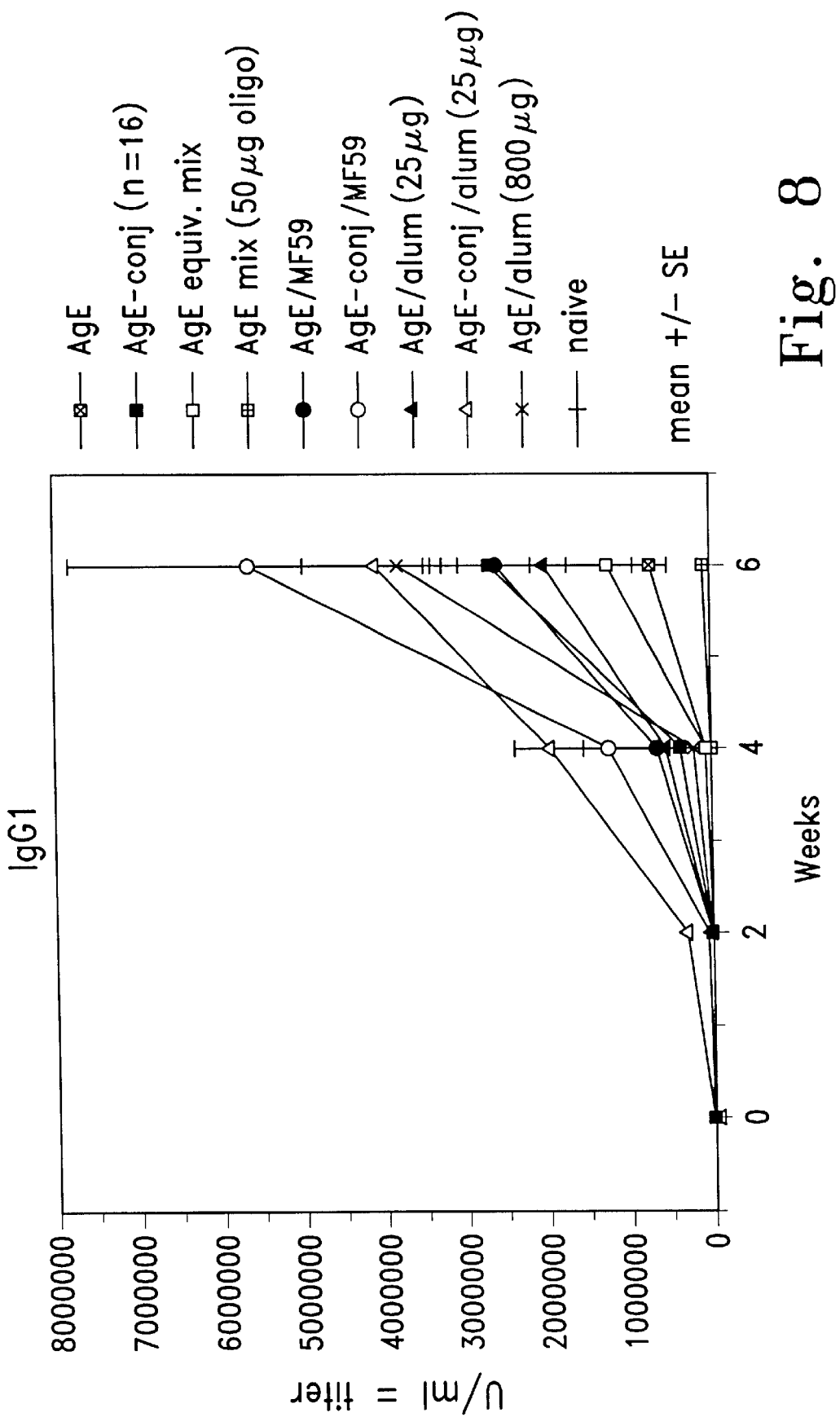
FIG. 8 is a graph depicting serum levels of anti-Amb aI IgG1 generated in treated animals.

As shown in FIG. 7, administration of antigen alone or in a mixture with ISS resulted in almost no anti-AgE IgG2a production, whereas administration of an antigen-ISS conjugate generated a significant level of anti-AgE IgG2a antibody. Simultaneous co-administration of an antigen-ISS conjugate and adjuvant MF59 resulted in an approximately two-fold increase in anti-AgE IgG2a antibody production relative to that obtained from the administration of the antigen-ISS conjugate alone. Thus, administration of antigen and ISS in proximate association, such as in the form of a conjugate, or co-administration of MF59 and antigen-ISS increased the primary Th1-type immune response generated by the antigen or by the antigen-ISS conjugate, respectively, indicating that the ISS has an independent adjuvant activity.

Figure 9:
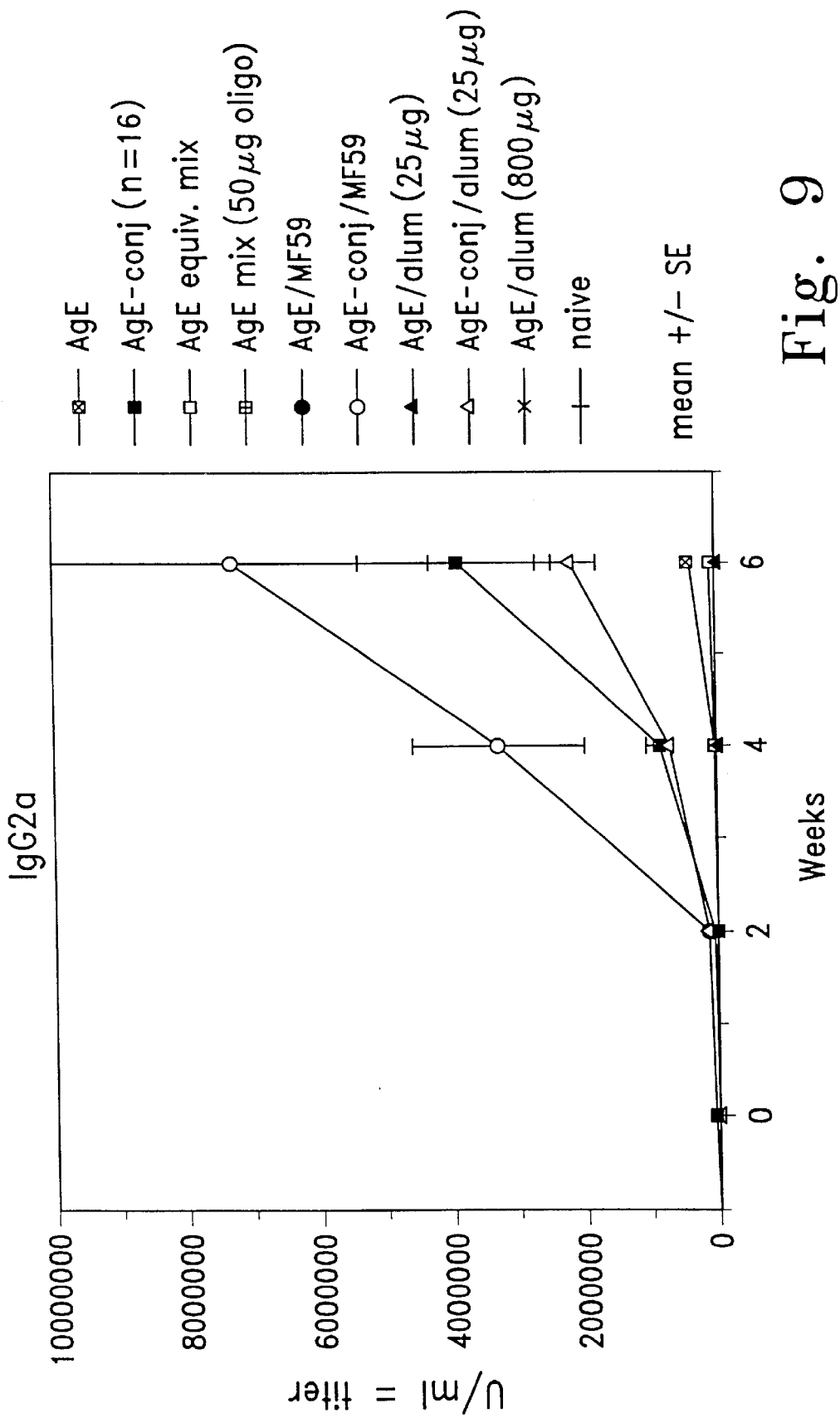
FIG. 9 is a graph depicting serum levels of anti-Amb aI IgG2a generated in treated animals.
Figure 10:
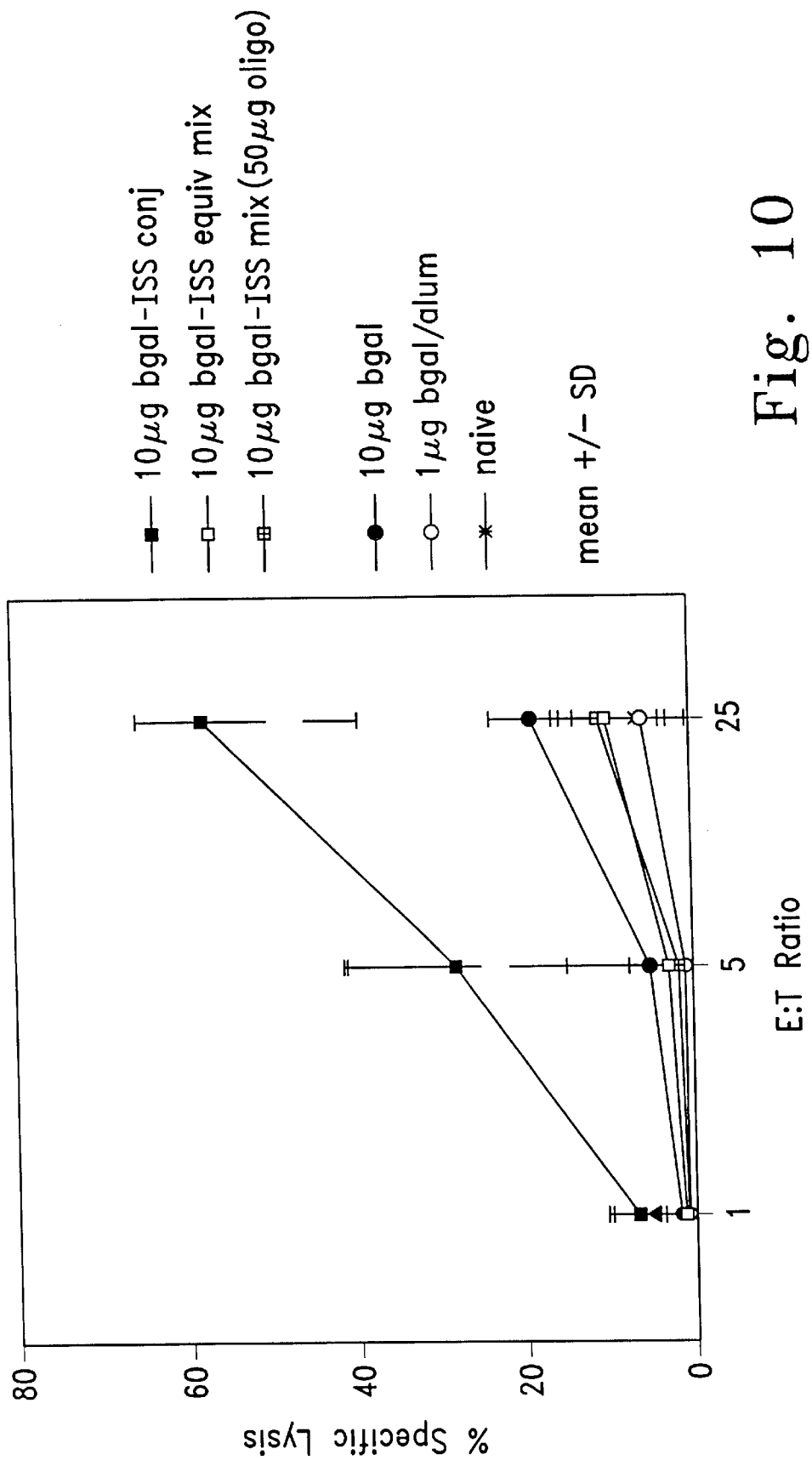
FIG. 10 is a graph depicting CTL responses from splenocytes of treated animals.

Anti-AgE IgG2a production as a result of co-administration of alum and antigen-ISS conjugate as compared to that of co-administration of antigen and alum also indicates an independent adjuvant activity associated with ISS (FIG. 9).

CpG containing oligonucleotides were recently shown to promote a Th1-type immune response when administered with antigen and incomplete Freund's adjuvant (IFA) as compared to the Th2-type response generated to the administration of antigen with IFA alone. Chu et al. (1997) *J. Exp. Med* 10:1623–1631. In this study, the oligonucleotides were always administered in the presence or the presence of IFA. Although this study indicates that co-administration of CpG-containing oligonucleotides with an antigen and an adjuvant can result in a shift in the immune response from a Th2-type response to a Th1-type response, experiments were not performed to indicate any independent adjuvant activity for the oligonucleotide, as presented in the instant invention.

Example 4

Selective Induction of a Th1-type Response in a Host after Administration of a Composition Comprising an ISS As described herein, a Th1-type immune response is associated with the production of specific cytokines, such as IFN-γ, and results in production of CTLs.

To determine if a Th1-type immune response would be produced in mice receiving ISS oligonucleotide compositions according to the invention, mice were immunized with β-galactosidase (β-Gal) protein in various compositions, with and without co-administration of ISS oligonucleotides. The compositions used included 1 or 10 μg β-Gal and are listed in Table 4.

TABLE 4

| β-Gal | β-Gal-oligo 2 conjugate |
|---|---|
| β-Gal-oligo 2 mix (equivalent) | β-Gal-oligo 2 mix (50 μg oligo 2) |
| 1 μg β-Gal/Alum | |

BALB/c mice were injected intradermally with the amounts and compositions shown above and sacrificed 2 weeks after injection. Their antigen dependent CTL responses and cytokine secretion profile were tested in vitro. CTL responses were determined as described in Sato et al. (1996). Cytokine secretion was determined by ELISA tests. Naïve mice are also included in the experiment. Results are depicted in FIGS. 10–13.

Figure 11:
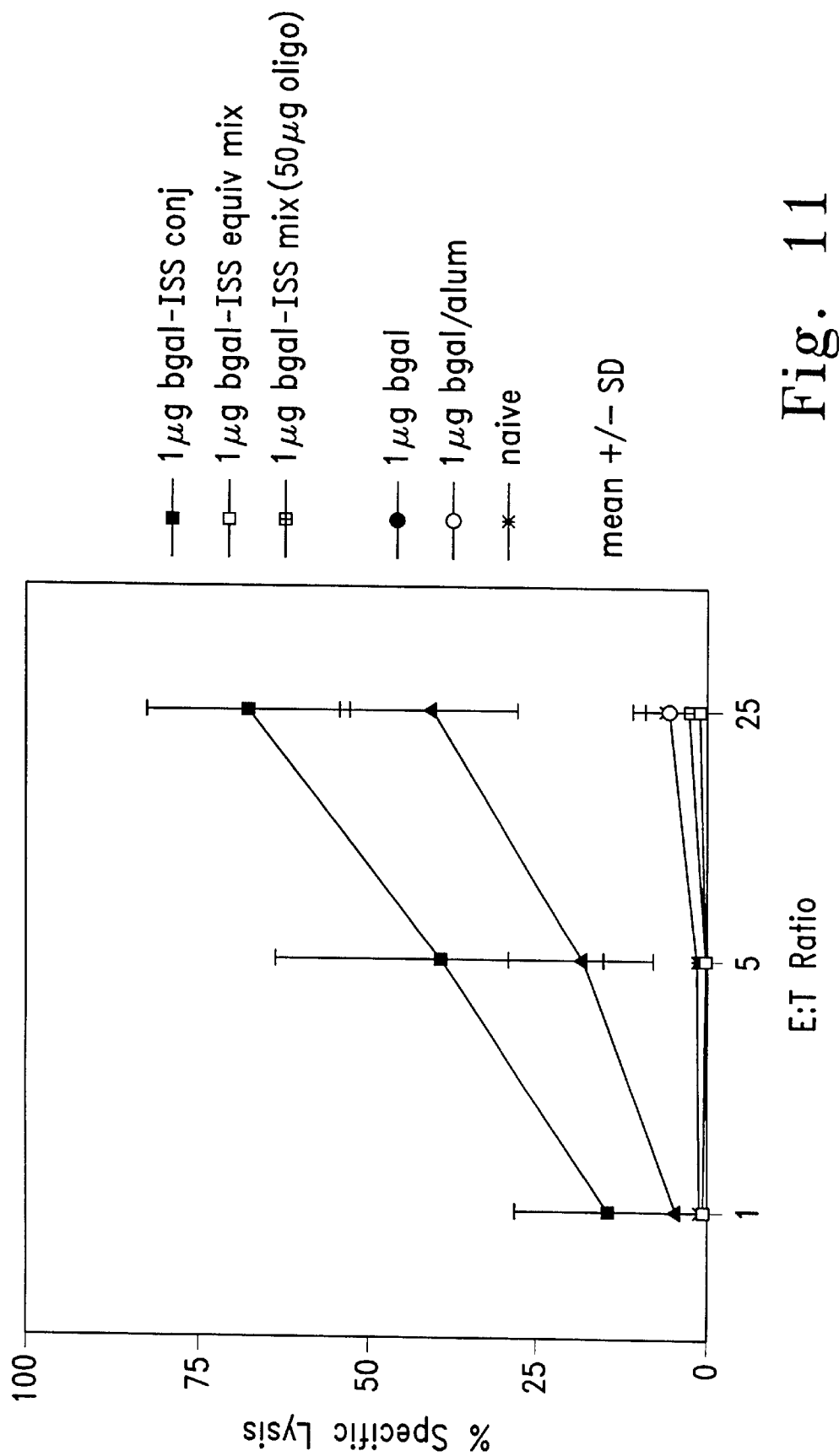
FIG. 11 is a graph depicting CTL responses from splenocytes of treated animals.
Figure 12:
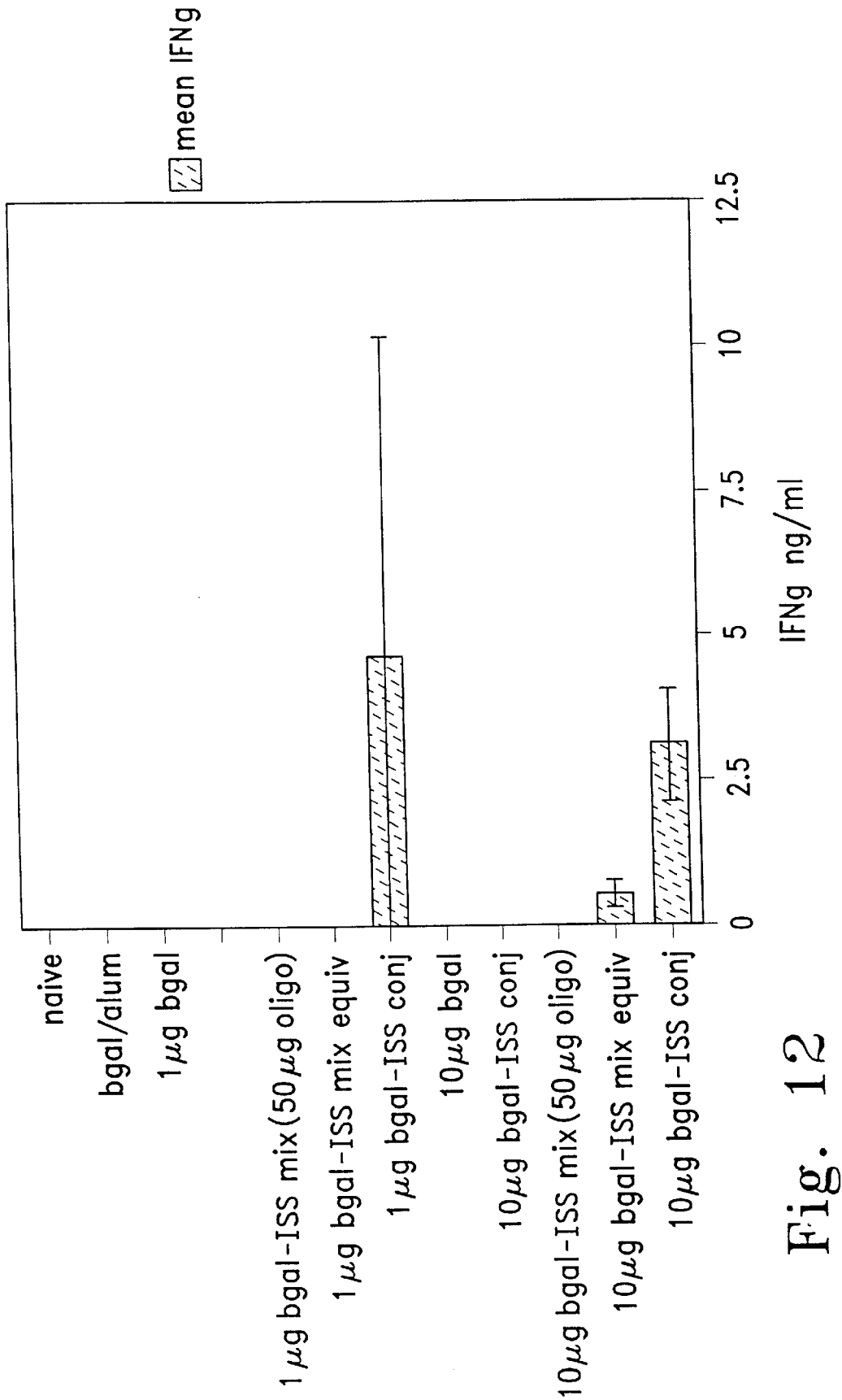
FIG. 12 is a graph depicting IFN-γ produced from splenocytes of treated animals.
Figure 13:
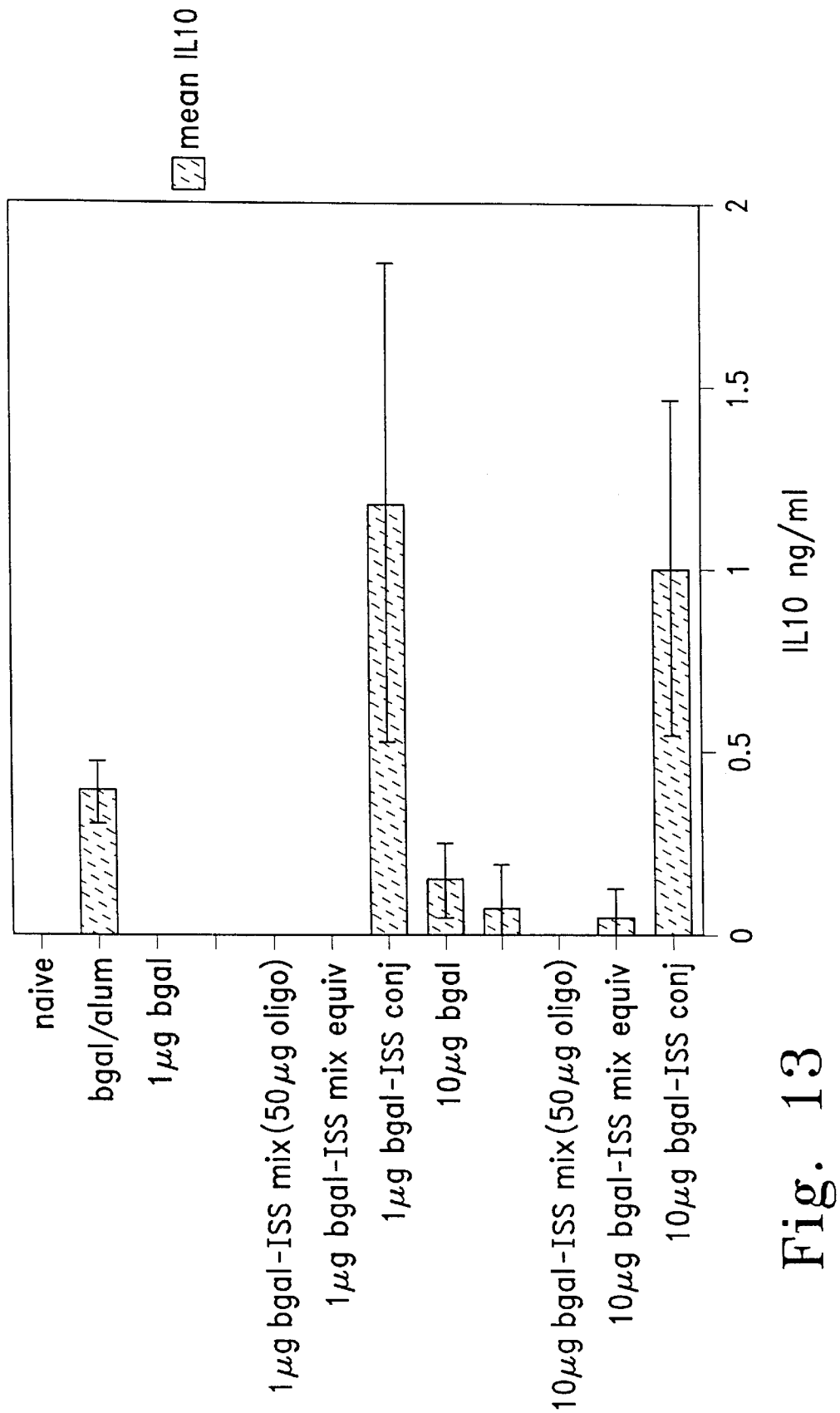
FIG. 13 is a graph depicting IL-10 produced from splenocytes of treated animals.

At an early time point in the immune response, two weeks after administration of the compositions, CTL activity was found from cells of mice receiving 10 μg antigen conjugated with an ISS (FIG. 10) Splenocytes from mice receiving 1 μg βgal conjugated with ISS generated an amount of CTL activity comparable to that of those receiving 10 μg βgal conjugated with ISS (FIG. 11). IFN-γ, a Th1-biased cytokine, was produced only from cells of mice which had received βgal conjugated with ISS (FIG. 12). Cells from these mice also produced IL-10, a Th2-biased cytokine (FIG. 13).

Example 5

Primate Immune Response to Antigen-ISS Compositions

To examine the immunomodulatory activity of ISS beyond in vitro and murine experiments, immune responses in the presence of ISS are examined in primates.

Figure 14:
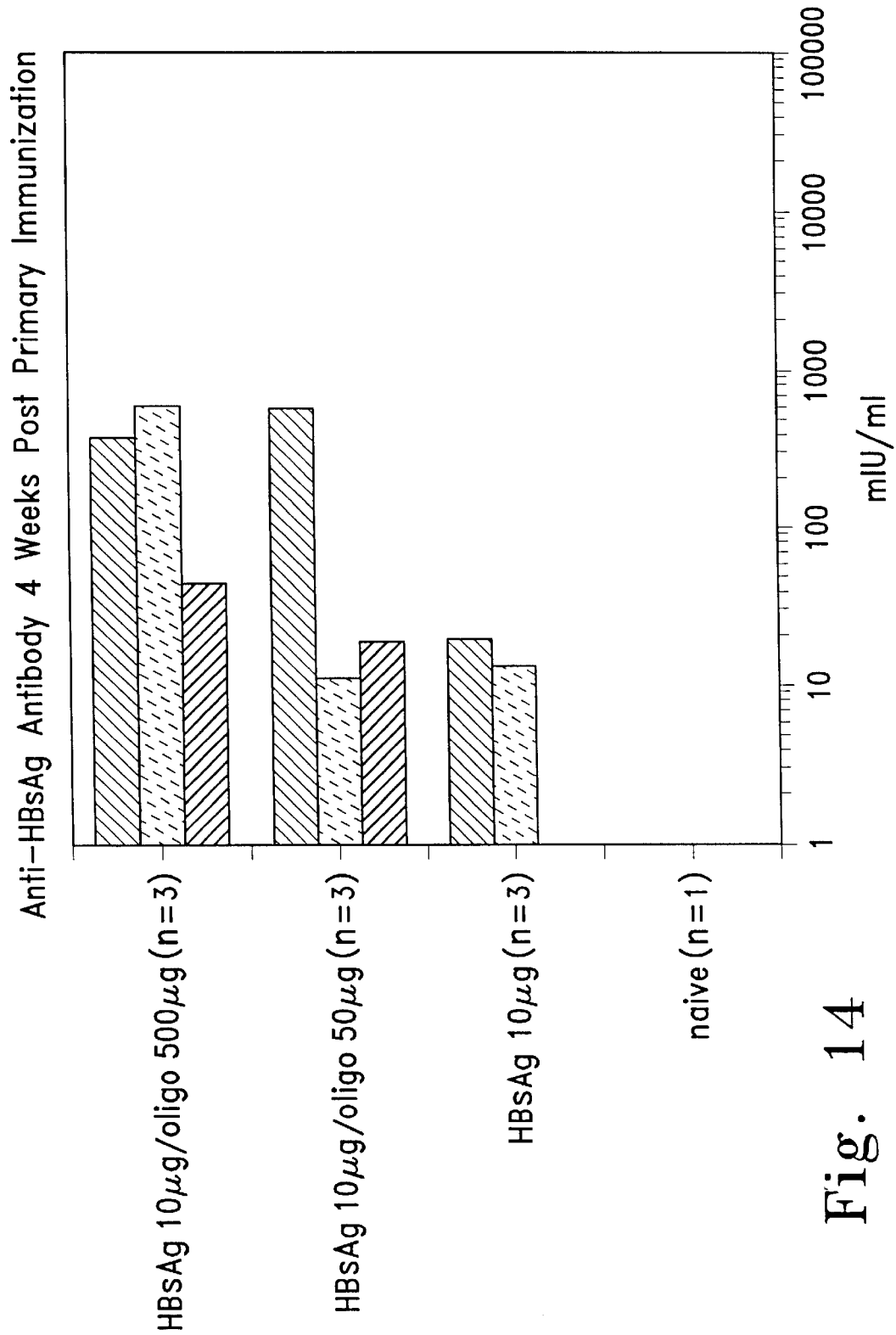
FIG. 14 is a graph depicting serum levels of anti-HBsAg antibodies four weeks after primary immunization.
Figure 15:
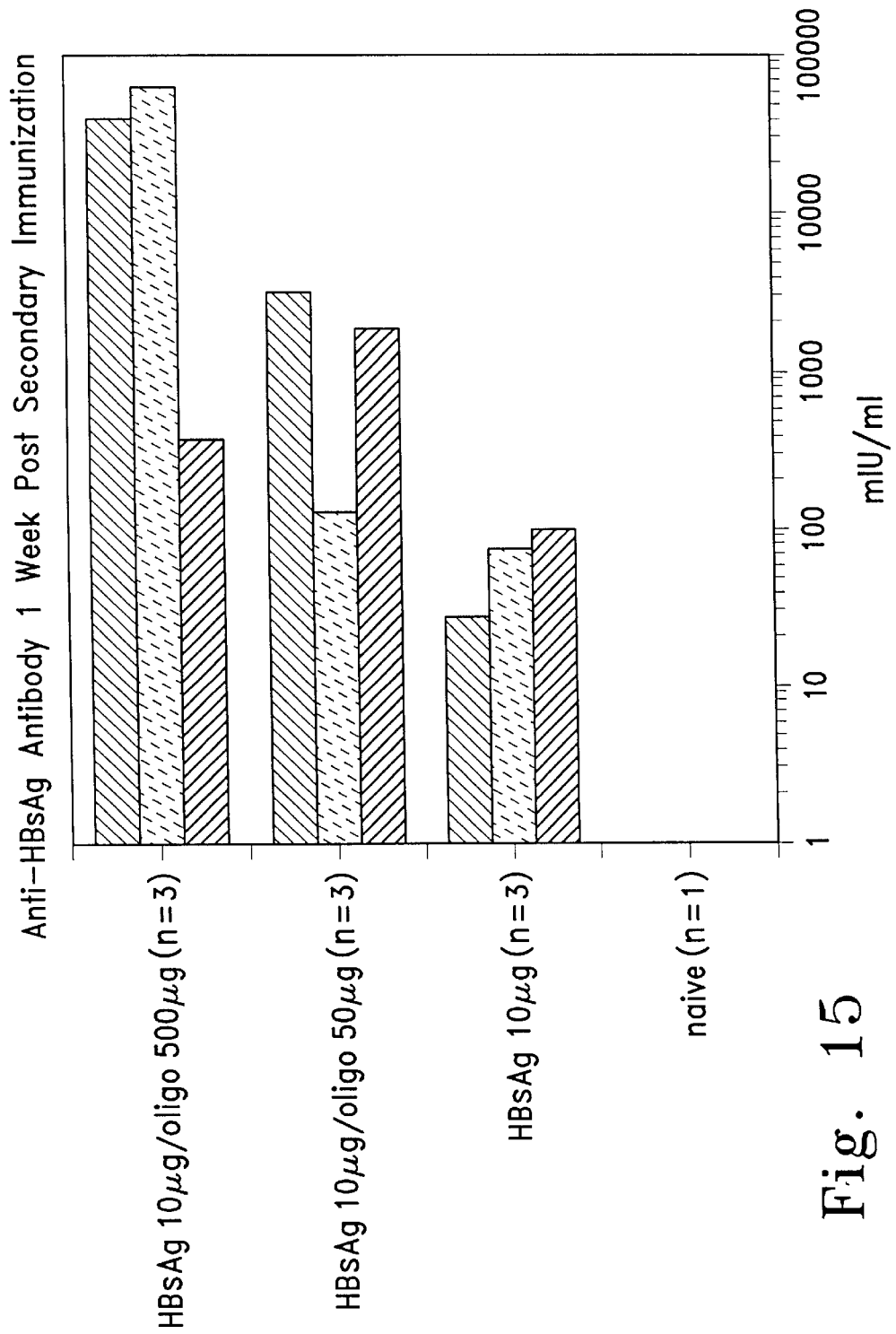
FIG. 15 is a graph depicting serum levels of anti-HBsAg antibodies one week after secondary immunization.
Figure 16:
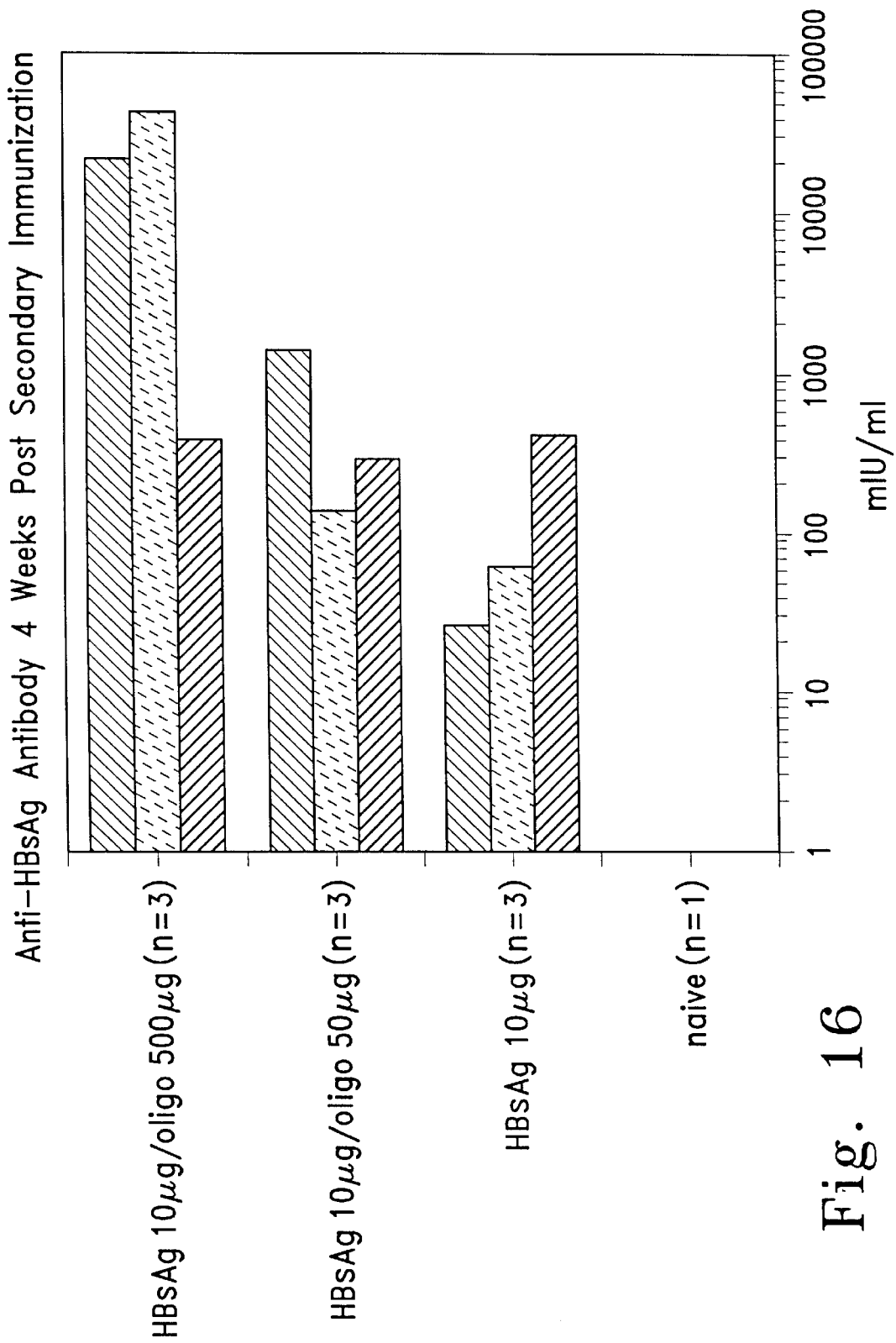
FIG. 16 is a graph depicting serum levels of anti-HBsAg antibodies four weeks after secondary immunization.

Cynomolgous monkeys were immunized intramuscularly with 10 μg hepatitis B surface antigen (HBsAg) either alone or mixed with either 50 μg of oligonucleotide 2 (SEQ ID NO:2) or 500 μg of oligonucleotide 2 at week 0, 4, and 8. Antibody responses to HBsAg were measured using Abbott Laboratories AUSAB kit at week 4 (4 weeks after first injection), week 5 (5 weeks after first injection and one week after second injection) and week 8 (8 weeks after first injection and 4 weeks after second injection). The results are shown in FIGS. 14, 15, and 16. At each time point examined, co-administration of antigen with ISS generally resulted in a greater antibody response to the antigen. Thus, in primates, ISS provides an adjuvant-like activity in the generation of an immune response to the co-administered antigen.

In the experiment with cynomolgus monkeys, ISS and antigen were administered as an admixture. To determine the immunomodulatory activity of an ISS-antigen conjugate in primates, baboons are injected with compositions comprising ISS-Amb aI conjugates. At appropriate intervals, antigen specific immune responses are determined as described herein. For example, antigen-specific serum antibody levels are determined and compared to such levels in pre-immune serum.

Example 6

Method of Screening for Immunostimulatory Oligonucleotides

To identify oligonucleotides with potential ISS activity, cell lines are treated with the oligonucleotides to be tested and resultant cytokine production is determined, if any. Cell lines used for the screening of ISS activity are the murine cell line P388D.1 or the human cell line 90196.B, both of which are available from the American Type Culture Collection.

Cells are grown and prepared using standard techniques. Cells are harvested during growth phase and are washed in RPMI 1640 media supplemented with 2% heat-inactivated fetal calf serum (FCS), 50 μM 2-mercaptoethanol, 1% penicillin-streptomycin, and 2 mM L-glutarnine and resuspended at approximately $4 \times 10^6$ cells/ml in 10% FCS/RPMI Cell cultures are set up in triplicate with approximately $4 \times 10^5$ cells/well in a 96-well, flat microtiter plate in 100 μl 10% FCS/RPMI with the cells allowed to rest for at lest 1 hour after plating. Oligonucleotides to be tested are diluted in 10% FCS/RPMI and 100 μl of oligonucleotide dilution is added to an appropriate well. In general, final oligonucleotide concentrations include 0.1 μg/ml, 1.0 μg/ml, and 10 μg/ml. Cells are then incubated for 1, 2, or 3 days.

To determine cell proliferation, 100 μl of supernatant is harvested from each well on appropriate days, pulsed with 1.0 μM tritiated thymidine and incubated overnight. Standard methods to assess tritiated thymidine incorporation are used to determine cell proliferation.

Cytokine production by the cells is determined by ELISAs of culture supernatant using commercially-available antibodies to the cytokines. Detection of >2 ng/ml IFN-γ and/or IL-12 in the cell culture supernatant 48 or 72 hours after addition of an oligonucleotide to the cells is indicative of ISS activity in the oligonucleotide. Production of IFN-γ and/or IL-12 in particular is indicative of activity to induce a Th1-type ISS immune response.

Although the foregoing invention has been described in some detail by way of illustration and example for purposes of clarity of understanding, it will be apparent to those skilled in the art that certain changes and modifications may be practiced. Therefore, the descriptions and examples should not be construed as limiting the scope of the invention, which is delineated by the appended claims.

What is claimed is:

1. An immunomodulatory oligonucleotide comprising the sequence of SEQ ID NO:2.

2. The immunomodulatory oligonucleotide according to claim 1, wherein the oligonucleotide is single-stranded.

3. The immunomodulatory oligonucleotide according to claim 1, wherein the oligonucleotide is double-stranded.

4. The immunomodulatory oligonucleotide according to claim 1, wherein the oligonucleotide comprises a phosphate backbone modification.

5. The immunomodulatory oligonucleotide according to claim 4, wherein the oligonucleotide comprises a phosphorothioate bond.

6. A composition comprising the immunomodulatory oligonucleotide according to claim 1 and a pharmaceutically acceptable carrier.

7. The composition according to claim 6, wherein the oligonucleotide is single-stranded.

8. An immunomodulatory composition comprising the immunomodulatory oligonucleotide according to claim 1;

and further comprising a facilitator selected from the group consisting of co-stimulatory molecules, cytokines, chemokines, targeting protein ligand, a trans-activating factor, a peptide, and a peptide comprising a modified amino acid.

9. The immunomodulatory composition of claim 8, wherein the facilitator is conjugated to the immunomodulatory oligonucleotide.

10. An immunomodulatory composition comprising the immunomodulatory oligonucleotide according to claim 1; and further comprising an antigen.

11. The immunomodulatory composition of claim 10, wherein the antigen is selected from the group consisting of peptides, glycoproteins, polysaccharides, and lipids.

12. The immunomodulatory composition according to claim 10, wherein the antigen comprises hepatitis B surface antigen (HBsAg).

13. The immunomodulatory composition according to claim 10, wherein the antigen is an allergen.

14. An immunomodulatory composition according to claim 10, wherein the oligonucleotide is single-stranded.

15. The immunomodulatory composition according to claim 10, wherein the oligonucleotide is double-stranded.

16. The immunomodulatory composition according to claim 10, wherein the oligonucleotide comprises a phosphate backbone modification.

17. The immunomodulatory composition according to claim 16, wherein the oligonucleotide comprises a phosphorothioate bond.

18. The immunomodulatory composition of claim 10, wherein the immunomodulatory oligonucleotide and the antigen are linked to a platform molecule.

19. The immunomodulatory composition of claim 18, further comprising an adjuvant.

20. The immunomodulatory composition of claim 19, further comprising a pharmaceutically acceptable carrier.

21. The immunomodulatory composition of claim 18, further comprising a pharmaceutically acceptable carrier.

22. The immunomodulatory composition according to claim 18, wherein the polynucleotide is single-stranded.

23. The immunomodulatory composition according to claim 18, wherein the polynucleotide is double-stranded.

24. The immunomodulatory composition according to claim 18, wherein the polynucleotide comprises a phosphate backbone modification.

25. The immunomodulatory composition according to claim 24, wherein the polynucleotide comprises a phosphorothioate bond.

26. The immunomodulatory composition of claim 10, wherein the immunomodulatory oligonucleotide and the antigen are adsorbed onto a nanoparticle.

27. The immunomodulatory composition of claim 26, wherein the nanoparticle is about 0.1 $\mu$m or less.

28. The immunomodulatory composition of claim 26, wherein the nanoparticle is organic.

29. The immunomodulatory composition of claim 26, further comprising an adjuvant.

30. The immunomodulatory composition of claim 26, further comprising a pharmaceutically acceptable carrier.

31. The immunomodulatory composition of claim 10, wherein the immunomodulatory oligonucleotide and the antigen are adsorbed onto an organic particle.

32. The immunomodulatory composition of claim 31, wherein the particle is about 0.1 $\mu$m or less.

33. The immunomodulatory composition of claim 31, further comprising an adjuvant.

34. The immunomodulatory composition of claim 31, further comprising a pharmaceutically acceptable carrier.

35. An immunomodulatory composition comprising a polynucleotide comprising the sequence of SEQ ID NO:2, an antigen and an encapsulating agent, wherein the polynucleotide and the antigen are not conjugated to each other, and wherein the polynucleotide and the antigen are encapsulated within the encapsulating agent.

36. The immunomodulatory composition of claim 35, wherein the encapsulation is within liposomes.

37. The immunomodulatory composition of claim 35, further comprising an adjuvant.

38. The composition according to claim 35, further comprising a pharmaceutically acceptable carrier.

39. The immunomodulatory composition according to claim 35, wherein the polynucleotide is single-stranded.

40. The immunomodulatory composition according to claim 35, wherein the polynucleotide is double-standed.

41. The immunomodulatory composition according to claim 35, wherein the polynucleotide comprises a phosphate backbone modification.

42. The immunomodulatory composition according to claim 41, wherein the polynucleotide comprises a phosphorothioate bond.

43. An immunomodulatory composition comprising (a) a polynucleotide comprising the sequence of SEQ ID NO:2; (b) an antigen; and (c) an adjuvant other than alum, wherein the polynucleotide and antigen are not conjugated to each other.

44. A composition according to claim 43, further comprising a pharmaceutically acceptable carrier.

45. An immunomodulatory composition according to claim 43, wherein the polynucleotide is single-stranded.

46. The immunomodulatory composition according to claim 43, wherein the polynucleotide is double-standed.

47. The immunomodulatory composition according to claim 43, wherein the polynucleotide comprises a phosphate backbone modification.

48. The immunomodulatory composition according to claim 47, wherein the polynucleotide comprises a phosphorothioate bond.

49. The immunomodulatory composition according to claim 43, wherein the antigen comprises hepatitis B surface antigen (HBsAg).

50. The immunomodulatory composition according to claim 43, wherein the antigen is an allergen.

* * * * *